US009822063B2

(12) United States Patent
Padovan et al.

(10) Patent No.: US 9,822,063 B2
(45) Date of Patent: Nov. 21, 2017

(54) STABLE SOLID FORMS OF ENCLOMIPHENE AND ENCLOMIPHENE CITRATE

(71) Applicant: F.I.S.-Fabbrica Italiana Sintetici S.P.A., Montecchio Maggiore (IT)

(72) Inventors: Pierluigi Padovan, Montecchio Maggiore (IT); Lorenzo Caruana, Montecchio Maggiore (IT); Nicolas Tesson, L'Hospitalet de Llobregat (ES)

(73) Assignee: F.I.S.—FABBRICA ITALIANA SINTETICI S.P.A, Montecchio Maggiore (VI) (IT)

( * ) Notice: Subject to any disclaimer, the term of this patent is extended or adjusted under 35 U.S.C. 154(b) by 0 days.

(21) Appl. No.: 15/115,133

(22) PCT Filed: Oct. 26, 2015

(86) PCT No.: PCT/EP2015/074746

§ 371 (c)(1),
(2) Date: Jul. 28, 2016

(87) PCT Pub. No.: WO2016/066584

PCT Pub. Date: May 6, 2016

(65) Prior Publication Data

US 2016/0347705 A1 Dec. 1, 2016

(30) Foreign Application Priority Data

Oct. 28, 2014 (EP) .................................... 14190738

(51) Int. Cl.

| | |
|---|---|
| ***C07C 217/54*** | (2006.01) |
| ***C07C 59/265*** | (2006.01) |
| ***C07C 217/18*** | (2006.01) |
| ***C07C 51/41*** | (2006.01) |
| ***C07C 53/10*** | (2006.01) |
| ***C07C 213/08*** | (2006.01) |

(52) U.S. Cl.

CPC .......... *C07C 217/54* (2013.01); *C07C 51/412* (2013.01); *C07C 53/10* (2013.01); *C07C 59/265* (2013.01); *C07C 213/08* (2013.01); *C07C 217/18* (2013.01); *C07B 2200/13* (2013.01)

(58) Field of Classification Search

CPC combination set(s) only.
See application file for complete search history.

(56) References Cited

U.S. PATENT DOCUMENTS

| | | | | |
|---|---|---|---|---|
| 2,914,563 | A | | 11/1959 | Allen et al. |
| 3,848,030 | A | * | 11/1974 | Viterbo et al. ...... C07F 9/65744 546/347 |

FOREIGN PATENT DOCUMENTS

| | | | |
|---|---|---|---|
| DE | 1155436 | B | 10/1963 |
| DE | 2224240 | A1 | 12/1972 |
| GB | 879792 | A | 10/1961 |
| WO | 2014/031177 | A1 | 2/2014 |

OTHER PUBLICATIONS

International Search Report issued in PCT Application No. PCT/EP2015/074746, (dated Apr. 6, 2016) (6 pages).

E.M. Dolginova et al., "Synthesis and Biological Study of the cis- and trans-Isomers of Clomiphene Citrate and Some Intermediates of its Synthesis", Pharmaceutical Chemistry Journal, 1984, vol. 18, No. 11, pp. 758-764.

F P Palopoli et al., "Substituted Aminoalkoxytriarylhaloethylenes", Journal of Medicinal Chemistry, 1967, vol. 10, pp. 84-86.

P. Narasimha Rao et al., "Synthesis of carbon-14 labeled clomiphene", Journal of Labelled Compounds and Radiopharmaceuticals, 1985, vol. 22, No. 3, pp. 245-255.

M J McLeish., "Clomiphene Citrate", Analytical Profiles of Drug Substances and Excipients, 1998, vol. 25, pp. 85-120.

A. Richardson et al., "Stereochemistries of geometric isomers of 4-(2-bromo-1, 2-diphenylvinyl) phenol, 4-(2-bromo-1, 2-diphenylvinyl) anisole, and 2-[p-(2-bromo-1,2-diphenylvinyl) phenoxy] triethylamine: Corrections of the literature", Journal of Pharmaceutical Sciences, 1976, vol. 65, No. 10, pp. 1545-1547.

S. Ernst et al., (E)-1-[p-(Diethylaminoethoxy) phenyl]-1,2-diphenyl-2-chloroethylene Hydrochloride (Clomiphene Hydrochloride), ACTA CRYST, 1976, pp. 291-293.

* cited by examiner

*Primary Examiner* — Michael Barker
*Assistant Examiner* — Amanda L Aguirre
(74) *Attorney, Agent, or Firm* — Lucas & Mercanti, LLP

(57) ABSTRACT

The present invention refers to new solid forms of Enclomiphene citrate and Enclomiphene base, processes for preparing thereof and uses.

7 Claims, 31 Drawing Sheets

Fig. 7-B
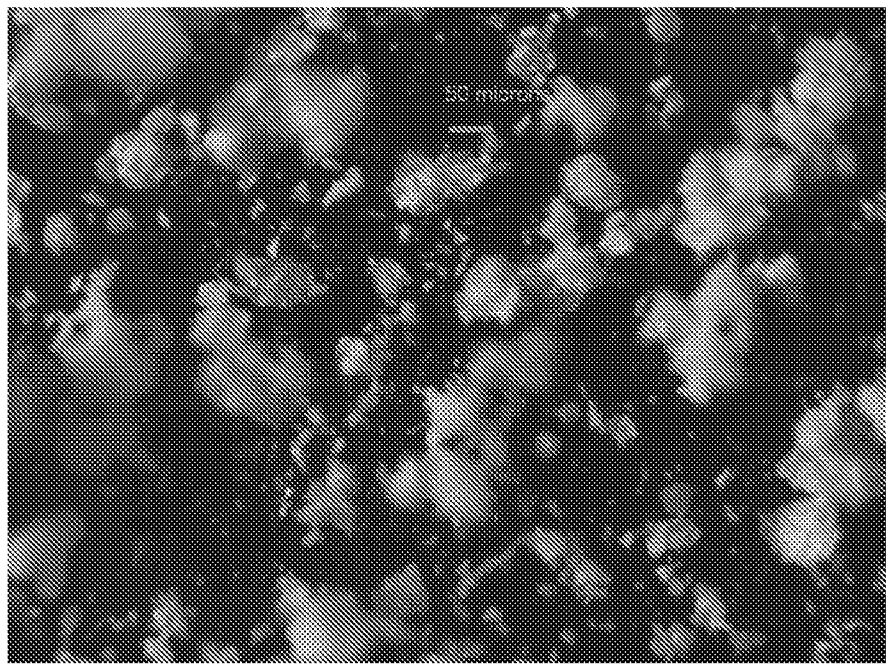
Fig. 8-B
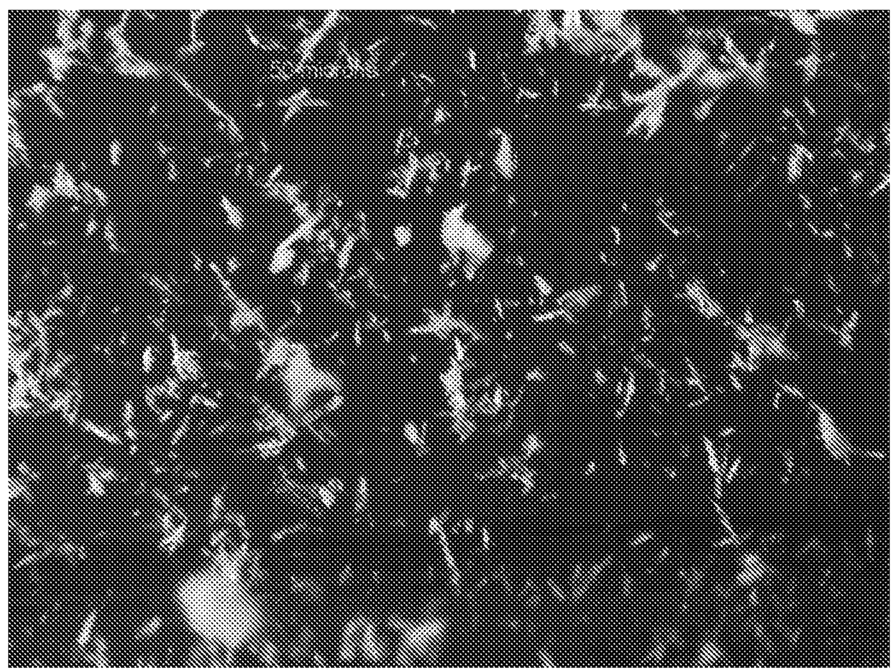

Fig. 11-B
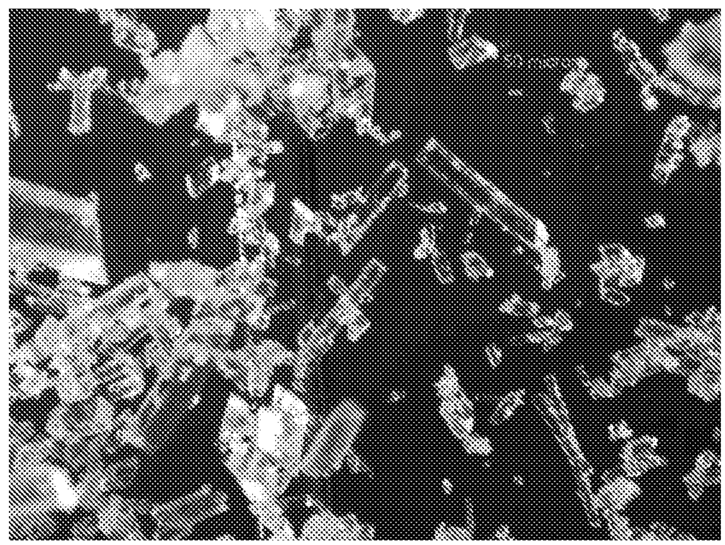
Fig. 12-B

Fig. 20 – continuation

E39-724__13 Oct 2015_01.$ls

| Channel Diameter (Lower) µm | Diff. Volume % | Cum. < Volume % |
|---|---|---|
| 0.03999 | 0.000206657 | 0 |
| 0.0439996 | 0.000266436 | 0.000206657 |
| 0.0481915 | 0.000417753 | 0.000473093 |
| 0.0529029 | 0.000838473 | 0.000890846 |
| 0.0580749 | 0.00176369 | 0.00172932 |
| 0.0637526 | 0.00327323 | 0.003493 |
| 0.0699854 | 0.00494351 | 0.00676624 |
| 0.0768275 | 0.00646364 | 0.0117097 |
| 0.0843365 | 0.00791046 | 0.0181734 |
| 0.0925838 | 0.00942589 | 0.0260838 |
| 0.101635 | 0.0109328 | 0.0355097 |
| 0.111572 | 0.0123247 | 0.0464425 |
| 0.122479 | 0.0137232 | 0.0587672 |
| 0.134454 | 0.0150257 | 0.0724904 |
| 0.147598 | 0.0161694 | 0.0875161 |
| 0.162028 | 0.0172107 | 0.103686 |
| 0.177869 | 0.018331 | 0.120896 |
| 0.195258 | 0.0194549 | 0.139227 |
| 0.214348 | 0.0205007 | 0.158682 |
| 0.235303 | 0.0214654 | 0.179183 |
| 0.258308 | 0.0224374 | 0.200648 |
| 0.283561 | 0.0233172 | 0.223085 |
| 0.311283 | 0.0240723 | 0.246402 |
| 0.341716 | 0.0247081 | 0.270474 |
| 0.375124 | 0.0253055 | 0.295182 |
| 0.411798 | 0.0258666 | 0.320488 |
| 0.452057 | 0.0263374 | 0.346354 |
| 0.496252 | 0.0267195 | 0.372691 |
| 0.544768 | 0.027019 | 0.39941 |
| 0.598027 | 0.0273354 | 0.426429 |
| 0.656493 | 0.0275974 | 0.453765 |
| 0.720673 | 0.0278181 | 0.481362 |
| 0.791132 | 0.0279554 | 0.50918 |
| 0.868477 | 0.028171 | 0.537136 |
| 0.953383 | 0.0284214 | 0.565307 |
| 1.04659 | 0.0287358 | 0.593728 |
| 1.14891 | 0.0290678 | 0.622464 |
| 1.26123 | 0.0295556 | 0.651531 |
| 1.38454 | 0.0302484 | 0.681087 |
| 1.5199 | 0.0310746 | 0.711335 |
| 1.66849 | 0.0320694 | 0.7424 |
| 1.83161 | 0.0332875 | 0.774479 |
| 2.01068 | 0.0347553 | 0.807767 |
| 2.20725 | 0.0365033 | 0.842522 |
| 2.42304 | 0.0384911 | 0.879025 |
| 2.65993 | 0.0407181 | 0.917516 |
| 2.91998 | 0.0432233 | 0.958234 |
| 3.20546 | 0.0460012 | 1.00146 |
| 3.51883 | 0.0490633 | 1.04746 |
| 3.86284 | 0.052353 | 1.09652 |
| 4.24049 | 0.0559002 | 1.14887 |
| 4.65506 | 0.0596736 | 1.20478 |
| 5.11017 | 0.0637309 | 1.26444 |
| 5.60976 | 0.0680472 | 1.32817 |
| 6.1582 | 0.0725967 | 1.39621 |
| 6.76026 | 0.0774281 | 1.46881 |
| 7.42117 | 0.0825723 | 1.54624 |
| 8.14669 | 0.0881813 | 1.62881 |
| 8.94315 | 0.0942461 | 1.71699 |
| 9.81748 | 0.10098 | 1.81124 |
| 10.7773 | 0.108405 | 1.9122 |
| 11.8309 | 0.11692 | 2.0206 |
| 12.9876 | 0.126607 | 2.13752 |
| 14.2573 | 0.137753 | 2.26413 |
| 15.6512 | 0.150555 | 2.40188 |
| 17.1813 | 0.165385 | 2.55244 |
| 18.861 | 0.182538 | 2.7178 |
| 20.705 | 0.202123 | 2.90034 |
| 22.7292 | 0.224118 | 3.10246 |
| 24.9513 | 0.248090 | 3.32658 |
| 27.3906 | 0.273917 | 3.57466 |
| 30.0685 | 0.301748 | 3.84857 |
| 33.0081 | 0.332296 | 4.15031 |
| 36.2352 | 0.366779 | 4.48261 |
| 39.7777 | 0.408817 | 4.84939 |
| 43.6665 | 0.45452 | 5.2582 |
| 47.9356 | 0.512456 | 5.71272 |
| 52.622 | 0.582035 | 6.22518 |
| 57.7666 | 0.673706 | 6.80721 |
| 63.4141 | 0.766597 | 7.48092 |
| 69.6136 | 0.947506 | 8.24752 |
| 76.4186 | 1.09882 | 9.19503 |
| 83.8907 | 1.29886 | 10.2939 |
| 92.0923 | 1.52033 | 11.5928 |
| 101.096 | 1.75285 | 13.1131 |
| 110.979 | 1.98673 | 14.866 |
| 121.829 | 2.21729 | 16.8527 |
| 133.74 | 2.44651 | 19.07 |
| 146.815 | 2.68157 | 21.5168 |
| 161.168 | 2.93055 | 24.1984 |
| 176.926 | 3.1967 | 27.129 |
| 194.222 | 3.47873 | 30.3257 |
| 213.21 | 3.76983 | 33.8044 |
| 234.054 | 4.05888 | 37.5742 |
| 256.936 | 4.33025 | 41.6331 |
| 282.056 | 4.5636 | 45.9634 |
| 309.631 | 4.73358 | 50.527 |
| 339.902 | 4.81479 | 55.2606 |
| 373.132 | 4.78537 | 60.0754 |
| 409.611 | 4.63777 | 64.8608 |
| 449.657 | 4.39462 | 69.4988 |
| 493.617 | 4.04782 | 73.8936 |
| 541.876 | 3.69772 | 77.9414 |
| 594.852 | 3.33947 | 81.6391 |
| 653.008 | 2.99714 | 84.9786 |
| 716.849 | 2.66277 | 87.9757 |
| 786.932 | 2.31389 | 90.6385 |
| 863.866 | 1.94421 | 92.9524 |
| 948.322 | 1.57554 | 94.8966 |
| 1041.03 | 1.22699 | 96.4721 |
| 1142.81 | 0.921693 | 97.6991 |
| 1254.54 | 0.678428 | 98.6208 |
| 1377.19 | 0.422598 | 99.2992 |
| 1511.83 | 0.199601 | 99.7218 |
| 1659.63 | 0.0699723 | 99.9214 |
| 1821.88 | 0.00858294 | 99.9914 |
| 2000 | | 100 |

Fig. 21 – continuation 639-725__13 Oct 2015_04.$ls

| Channel Diameter (Lower) μm | Diff. Volume % | Cum. < Volume % | Channel Diameter (Lower) μm | Diff. Volume % | Cum. < Volume % |
|---|---|---|---|---|---|
| 0.03999 | 0.00213468 | 0 | 18.861 | 3.74117 | 38.4667 |
| 0.0438596 | 0.00291671 | 0.00213468 | 20.708 | 3.8362 | 42.2078 |
| 0.0481915 | 0.0049542 | 0.00505139 | 22.7282 | 3.93451 | 46.045 |
| 0.0529029 | 0.0102357 | 0.00990558 | 24.9513 | 3.98882 | 49.9785 |
| 0.0580749 | 0.0213082 | 0.0201413 | 27.3906 | 3.93762 | 53.9666 |
| 0.0637526 | 0.0379893 | 0.0414495 | 30.0685 | 3.73725 | 57.9071 |
| 0.0699654 | 0.054369 | 0.0794428 | 33.0081 | 3.40367 | 61.6443 |
| 0.0768275 | 0.0692598 | 0.133639 | 36.2353 | 3.0111 | 65.048 |
| 0.0843305 | 0.0837298 | 0.203067 | 39.7777 | 2.65769 | 68.0591 |
| 0.0925638 | 0.0991553 | 0.286617 | 43.6666 | 2.41955 | 70.7168 |
| 0.101636 | 0.113862 | 0.385972 | 47.9356 | 2.32499 | 73.1363 |
| 0.111572 | 0.127089 | 0.499834 | 52.622 | 2.34745 | 75.461 |
| 0.122479 | 0.140593 | 0.626904 | 57.7666 | 2.43078 | 77.8085 |
| 0.134454 | 0.152443 | 0.767497 | 63.4141 | 2.5159 | 80.2392 |
| 0.147598 | 0.163164 | 0.919939 | 69.6138 | 2.5691 | 82.7551 |
| 0.162028 | 0.172754 | 1.0831 | 76.4186 | 2.58275 | 85.3242 |
| 0.177869 | 0.183147 | 1.25586 | 83.8907 | 2.59548 | 87.907 |
| 0.195258 | 0.192718 | 1.439 | 92.0923 | 2.54572 | 90.5124 |
| 0.214348 | 0.201237 | 1.63172 | 101.096 | 2.37512 | 93.0582 |
| 0.235303 | 0.208653 | 1.83296 | 110.979 | 2.01087 | 95.4333 |
| 0.258308 | 0.215594 | 2.04161 | 121.829 | 1.44457 | 97.444 |
| 0.283561 | 0.221963 | 2.25721 | 133.74 | 0.781136 | 98.8886 |
| 0.311283 | 0.227091 | 2.47917 | 146.815 | 0.277904 | 99.6698 |
| 0.341716 | 0.230966 | 2.70626 | 161.168 | 0.0491309 | 99.9477 |
| 0.375124 | 0.23342 | 2.93725 | 176.925 | 0.00321025 | 99.9968 |
| 0.411796 | 0.235523 | 3.17067 | 194.222 | 0 | 100 |
| 0.452057 | 0.236427 | 3.40619 | 213.21 | 0 | 100 |
| 0.496252 | 0.236136 | 3.64262 | 234.054 | 0 | 100 |
| 0.544769 | 0.233971 | 3.87876 | 256.936 | 0 | 100 |
| 0.598027 | 0.231189 | 4.11262 | 282.056 | 0 | 100 |
| 0.656493 | 0.227419 | 4.34381 | 309.631 | 0 | 100 |
| 0.720675 | 0.222606 | 4.57123 | 339.902 | 0 | 100 |
| 0.791132 | 0.215996 | 4.79384 | 373.132 | 0 | 100 |
| 0.868477 | 0.209602 | 5.00983 | 409.611 | 0 | 100 |
| 0.953383 | 0.200916 | 5.21664 | 449.657 | 0 | 100 |
| 1.04659 | 0.1926 | 5.41955 | 493.617 | 0 | 100 |
| 1.14891 | 0.183421 | 5.61206 | 541.876 | 0 | 100 |
| 1.26123 | 0.174283 | 5.79547 | 594.852 | 0 | 100 |
| 1.38454 | 0.165607 | 5.96976 | 653.008 | 0 | 100 |
| 1.5199 | 0.15779 | 6.13536 | 716.849 | 0 | 100 |
| 1.66849 | 0.151451 | 6.29315 | 786.932 | 0 | 100 |
| 1.83161 | 0.146263 | 6.4446 | 863.866 | 0 | 100 |
| 2.01068 | 0.145193 | 6.59156 | 948.322 | 0 | 100 |
| 2.20725 | 0.147165 | 6.73675 | 1041.03 | 0 | 100 |
| 2.42304 | 0.154418 | 6.88392 | 1142.81 | 0 | 100 |
| 2.65993 | 0.168355 | 7.03834 | 1254.54 | 0 | 100 |
| 2.91998 | 0.190536 | 7.20669 | 1377.19 | 0 | 100 |
| 3.20545 | 0.222906 | 7.39723 | 1511.83 | 0 | 100 |
| 3.51883 | 0.267301 | 7.62019 | 1659.63 | 0 | 100 |
| 3.86284 | 0.326039 | 7.88749 | 1821.88 | 0 | 100 |
| 4.24049 | 0.401104 | 8.21353 | 2000 | | 100 |
| 4.65505 | 0.494373 | 8.61463 | | | |
| 5.11017 | 0.607348 | 9.109 | | | |
| 5.60976 | 0.74207 | 9.71635 | | | |
| 6.1582 | 0.901443 | 10.4584 | | | |
| 6.76025 | 1.08842 | 11.3599 | | | |
| 7.42117 | 1.30508 | 12.4483 | | | |
| 8.14669 | 1.55663 | 13.7543 | | | |
| 8.94315 | 1.84278 | 15.3109 | | | |
| 9.81746 | 2.16355 | 17.1537 | | | |
| 10.7773 | 2.5092 | 19.3172 | | | |
| 11.8309 | 2.85548 | 21.8264 | | | |
| 12.9876 | 3.16464 | 24.6819 | | | |
| 14.2573 | 3.40311 | 27.8465 | | | |
| 15.6512 | 3.56603 | 31.2497 | | | |
| 17.1813 | 3.65697 | 34.8097 | | | |

Fig. 22 - continuation

E39-725___13 Oct 2015_01.$ls

| Channel Diameter (Lower) μm | Diff. Volume % | Cum. < Volume % | Channel Diameter (Lower) μm | Diff. Volume % | Cum. < Volume % |
|---|---|---|---|---|---|
| 0.03999 | 0.0874623 | 0 | 18.861 | 0 | 100 |
| 0.0439098 | 0.115644 | 0.0874623 | 20.705 | 0 | 100 |
| 0.0481915 | 0.205171 | 0.203106 | 22.7293 | 0 | 100 |
| 0.0529029 | 0.365433 | 0.408278 | 24.9513 | 0 | 100 |
| 0.0580749 | 0.620978 | 0.773711 | 27.3908 | 0 | 100 |
| 0.0637526 | 1.00308 | 1.39469 | 30.0685 | 0 | 100 |
| 0.0699854 | 1.45668 | 2.39776 | 33.0081 | 0 | 100 |
| 0.0768275 | 1.89048 | 3.85444 | 36.2353 | 0 | 100 |
| 0.0843385 | 2.24167 | 5.74492 | 39.7777 | 0 | 100 |
| 0.0925838 | 2.55932 | 7.98659 | 43.6668 | 0 | 100 |
| 0.101635 | 2.87152 | 10.5459 | 47.9358 | 0 | 100 |
| 0.111572 | 3.1761 | 13.4174 | 52.622 | 0 | 100 |
| 0.122479 | 3.41299 | 16.5935 | 57.7668 | 0 | 100 |
| 0.134454 | 3.58782 | 20.0065 | 63.4141 | 0 | 100 |
| 0.147598 | 3.74668 | 23.5943 | 69.6138 | 0 | 100 |
| 0.162028 | 3.87768 | 27.341 | 76.4196 | 0 | 100 |
| 0.177869 | 3.86267 | 31.2186 | 83.8907 | 0 | 100 |
| 0.195258 | 3.82718 | 35.0813 | 92.0923 | 0 | 100 |
| 0.214348 | 3.77871 | 38.9085 | 101.098 | 0 | 100 |
| 0.235303 | 3.70446 | 42.6872 | 110.978 | 0 | 100 |
| 0.258308 | 3.52945 | 46.3917 | 121.828 | 0 | 100 |
| 0.283561 | 3.22461 | 49.9211 | 133.74 | 0 | 100 |
| 0.311283 | 2.93476 | 53.1457 | 146.815 | 0 | 100 |
| 0.341718 | 2.67117 | 56.0805 | 161.168 | 0 | 100 |
| 0.375124 | 2.37487 | 58.7517 | 176.925 | 0 | 100 |
| 0.411798 | 1.87332 | 61.1266 | 194.222 | 0 | 100 |
| 0.452057 | 1.44338 | 62.9999 | 213.21 | 0 | 100 |
| 0.496252 | 1.00073 | 64.4432 | 234.054 | 0 | 100 |
| 0.544768 | 0.935318 | 65.443 | 256.938 | 0 | 100 |
| 0.598027 | 0.59488 | 66.3783 | 282.056 | 0 | 100 |
| 0.656493 | 0.412149 | 66.9732 | 309.631 | 0 | 100 |
| 0.720675 | 0.318413 | 67.3853 | 339.902 | 0 | 100 |
| 0.791132 | 0.329049 | 67.7037 | 373.132 | 0 | 100 |
| 0.868477 | 0.381511 | 68.0328 | 409.611 | 0 | 100 |
| 0.953383 | 0.563529 | 68.4143 | 449.657 | 0 | 100 |
| 1.04659 | 0.870082 | 68.9778 | 493.617 | 0 | 100 |
| 1.14891 | 1.42678 | 69.8479 | 541.876 | 0 | 100 |
| 1.26123 | 2.35292 | 71.2747 | 594.852 | 0 | 100 |
| 1.38454 | 3.32766 | 73.6276 | 653.008 | 0 | 100 |
| 1.5199 | 4.35425 | 76.9553 | 716.849 | 0 | 100 |
| 1.66848 | 5.50375 | 81.3095 | 786.933 | 0 | 100 |
| 1.83161 | 5.17728 | 86.8133 | 863.866 | 0 | 100 |
| 2.01068 | 4.07267 | 91.9905 | 948.323 | 0 | 100 |
| 2.20725 | 2.5717 | 96.0632 | 1041.03 | 0 | 100 |
| 2.42304 | 1.01916 | 98.6349 | 1142.81 | 0 | 100 |
| 2.65993 | 0.300153 | 99.6541 | 1254.54 | 0 | 100 |
| 2.91998 | 0.0457606 | 99.9542 | 1377.19 | 0 | 100 |
| 3.20545 | 0 | 100 | 1511.83 | 0 | 100 |
| 3.51883 | 0 | 100 | 1659.63 | 0 | 100 |
| 3.86284 | 0 | 100 | 1821.88 | 0 | 100 |
| 4.24049 | 0 | 100 | 2000 | | 100 |
| 4.65508 | 0 | 100 | | | |
| 5.11017 | 0 | 100 | | | |
| 5.60978 | 0 | 100 | | | |
| 6.1582 | 0 | 100 | | | |
| 6.76025 | 0 | 100 | | | |
| 7.42117 | 0 | 100 | | | |
| 8.14669 | 0 | 100 | | | |
| 8.94315 | 0 | 100 | | | |
| 9.81748 | 0 | 100 | | | |
| 10.7773 | 0 | 100 | | | |
| 11.8309 | 0 | 100 | | | |
| 12.9876 | 0 | 100 | | | |
| 14.2573 | 0 | 100 | | | |
| 15.6512 | 0 | 100 | | | |
| 17.1813 | 0 | 100 | | | |

Fig. 25 – B2
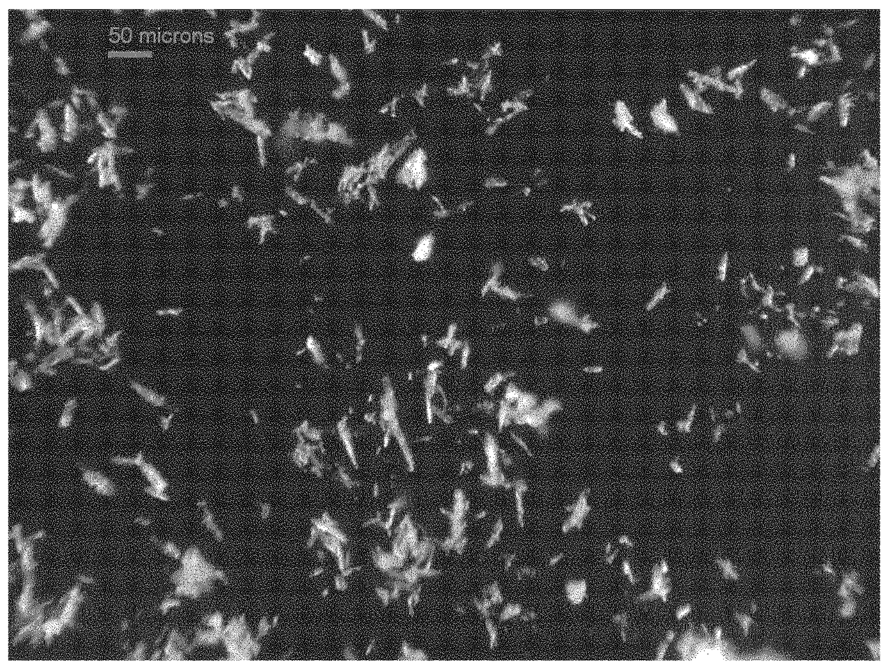
Fig. 25 – C
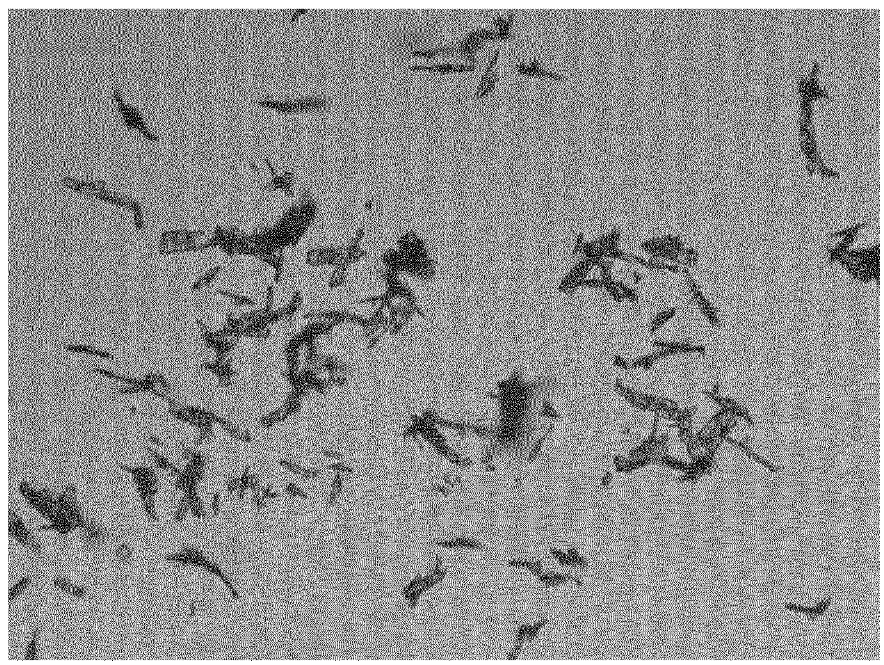

Fig. 25 – D
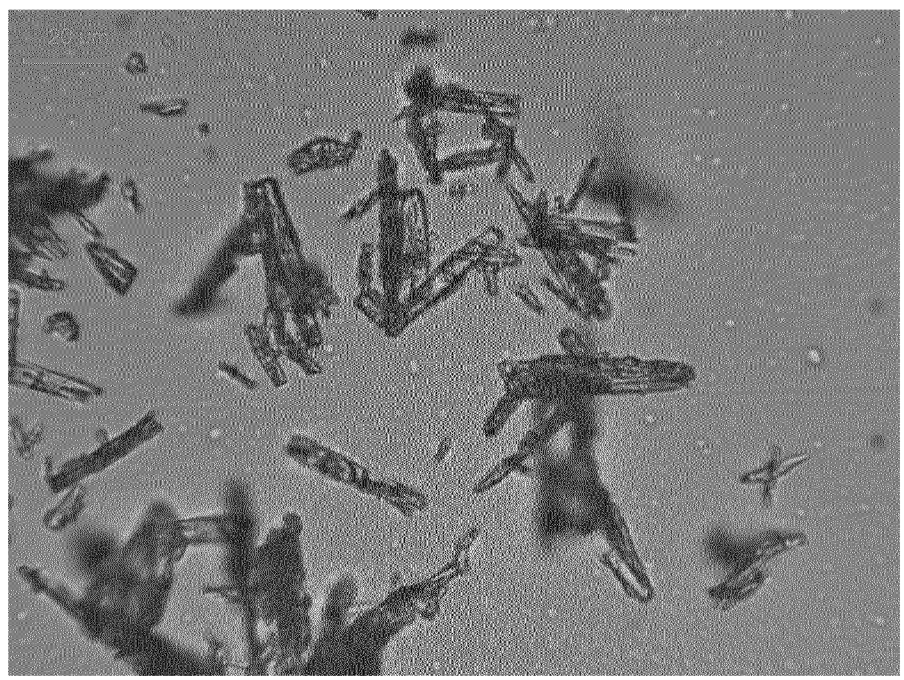

STABLE SOLID FORMS OF ENCLOMIPHENE AND ENCLOMIPHENE CITRATE

CROSS-REFERENCE TO RELATED APPLICATIONS

This application is a 371 of PCT/EP2015/074746 filed Oct. 26, 2015, which claims the benefit of European Patent Application No. 14190738.6, filed Oct. 28, 2014.

TECHNICAL FIELD

The present invention refers to processes for the preparation the active pharmaceutical ingredient named Clomiphene and, in particular, trans-Clomiphene, i.e. Enclomiphene.

Moreover, the invention refers to new solid forms of trans-Clomiphene and trans-Clomiphene citrate and processes for preparing thereof.

BACKGROUND ART

Clomiphene is an active pharmaceutical ingredient used as ovulatory stimulant to treat ovulatory dysfunction and polycystic ovary syndrome.

Clomiphene has chemical name Ethanamine, 2-[4-(2-chloro-1,2-diphenylethenyl)phenoxy]-N,N-diethyl and it is a mixture of the geometric isomers trans-Clomiphene of chemical formula (I) and cis-Clomiphene of chemical formula (II):

(I)

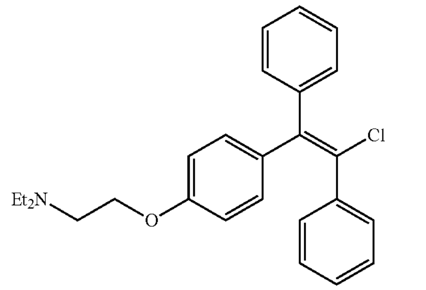

(II)

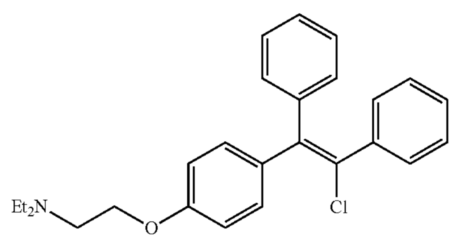

The pharmaceutical products currently on the market containing Clomiphene, typically as monocitrate salt, comprise Clomiphene having the following composition: from 50% to 70% of trans-clomiphene and from 30% to 50% of cis-Clomiphene.

Trans-Clomiphene of chemical formula (I), also named Enclomiphene or E-Clomiphene, as monocitrate salt, i.e. trans-Clomiphene monocitrate or Enclomiphene citrate which is Enclomiphene citrate (1:1), having formula (III):

(III)

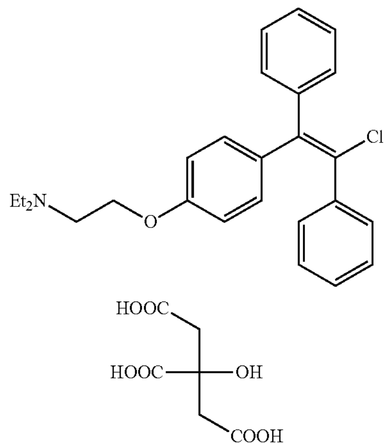

is currently under evaluation in clinical phase III for the treatment of secondary hypergonadism. Moreover, it is also said that trans-Clomiphene, i.e. Enclomiphene, could be potentially used for an adjuvant therapy in hypogonadal men with Type 2 diabetes.

The U.S. Pat. No. 3,848,030, in examples 31 and 32, discloses a process for the resolution of the geometric isomers of Clomiphene through the preparation of salts with racemic binaphthyl-phosphoric acid.

In the later publication Acta Cryst. (1976), B32, pag. 291-293, the geometric isomery has been definitely established by single crystal X-Ray diffraction.

Finally, in the publication "Analytical profiles of drug substances and excipients", vol. 25, (1998), pag. 85-121, in particular at pag. 99, it is stated that prior to 1976 the cis stereochemistry was wrongly assigned to the trans-isomer of Clomiphene (E-Chlomiphene or Enclomiphene), and only after the above publication on Acta Cryst. the correct geometric isomery has been definitively assigned.

These observations in the prior art have been confirmed by our experimentation. In particular, repeating the experiment 31 of U.S. Pat. No. 3,848,030, the trans-Clomiphene salt with racemic binaphthyl-phosphoric acid was isolated and not the salt with cis-Clomiphene as stated in said patent, as confirmed by 2D H-NMR analysis (NOESY experiment). Thus, Example 31 of U.S. Pat. No. 3,848,030, provides, at the end, Enclomiphene citrate, crystallized from a mixture of ethyl ether and ethanol, having a m.p. of 133-135° C. Example 32, instead provided Cis-Clomiphene citrate, crystallized from a mixture of ethyl ether and ethanol, having a m.p. of 120-126° C.

Thus, with the aim of preparing Enclomiphene citrate, whole experiment 31 of U.S. Pat. No. 3,848,030 has been reworked also carrying out the crystallization of the product form a mixture of ethyl ether and ethanol, hence providing a not crystalline solid with two DSC peaks respectively at 114° C. and 188° C., although the starting material used for the reworking example was quite a pure substance (see notes below related to the salt of trans-Clomiphene salt with racemic binaphthyl-phosphoric acid), and having a substantially the same chemical purity of that used in the prior art experiment.

The U.S. Pat. No. 2,914,563, in example 3, and the recent PCT application WO2014/031177, in example 1, disclose a process for the preparation of trans-Clomiphene citrate, containing from 30% to 50% of cis-Clomiphene, as citrate, by reaction of 1-p-(β-diethylaminoethoxy)phenyl]-1,2-diphenylethylene hydrochloride with N-chlorosuccinimmide in dry chloroform under reflux.

*Khimiko-Farmatsevticheskii Zhurnal* (1984), 18(11), 1318-24 English translation in the review *Pharmaceutical Chemistry Journal November* 1984, Volume 18, Issue 11, pag. 758-764 (Title: Synthesis and biological study of the cis- and trans-isomers of Clomiphene citrate and some intermediates of its synthesis) discloses the trans-isomer of Clomiphene citrate, i.e. Enclomiphene citrate, characterized by:

$^1$H-NMR (MeOD) d 7.4-6.7 (m, 14H); 4.27 (t, 2H, —$OCH_2$); 3.51 (t, 2H, $CH_2$—N); 3.28 (q, 4H, 2xN-$CH_2$)); 2.73 (2H); 2.78 (2H); 1.31 (t, 6H, 2xN—C—$CH_3$)) Melting point: 138-139° C. (98% purity by GLC);

IR spectrum, v $cm^{-1}$ (suspension in mineral oil): 3640, 3430, 1720, 1710 (citrate), 1600-1555 (broad band, stilbene system); 750.

UV spectrum: $\lambda$ max=243 nm, $\epsilon$ 21,800 and $\lambda$ max 300 nm, $\epsilon$ 11,400.

According to our experimental studies, these prior art methods for the preparation of Clomiphene and, in particular, of trans-Clomiphene, suffer from drawbacks related to unknown impurities which can contaminate the final product Clomiphene.

Moreover, Enclomiphene citrate was described in literature with different melting points, in particular, 133-135° C. and 138-139° C. Said solid forms of Enclomiphene citrate fail to comply with stabilities studies and furthermore show relatively poor solubility in water either in neutral or acid pH.

Example 31 of U.S. Pat. No. 3,848,030 does not disclose any solid form of Enclomiphene base, i.e. as free base, as well as example 32 does not disclose any form of cis-Clomiphene base.

A crystalline form of Enclomiphene base appears to be described in only one article: Khimiko-Farmatsevticheskii Zhurnal (1984), 18(11), 1318-24 English translation in the review Pharmaceutical Chemistry Journal November 1984, Volume 18, Issue 11, pag. 758-764 (Title: Synthesis and biological study of the cis- and trans-isomers of clomiphene citrate and some intermediates of its synthesis).

In this article the cis-isomer was isolated by fractional crystallization in petroleum ether. The evaporation of the mother liquors gave the trans-isomer with a purity of 86% (by GC). Repeated recrystallizations from hexane afforded analytic samples with a purity of 99%. This product was characterized by:

$^1$H-NMR ($C_6D_6$) d 7.55-6.85 (m, 12H); 6.52 (m, 2H); 3.66 (t, 2H, —$OCH_2$); 2.61 (t, 2H, $CH_2$—N); 2.36 (q, 4H, 2xN-$CH_2$)); 0.88 (t, 6H, 2xN—C—$CH_3$)); Melting point 73-75° C., UV spectrum: $\lambda$ max=242 nm, $\epsilon$ 21,600 and $\lambda$ max 297 nm, $\epsilon$ 11,200.

Said known solid form of Enclomiphene base has the drawback that shows bad flowability, thus showing difficulties for passing through funnels (see example 22+19+FIG. 16). Said difficulties are magnified using and processing said material for the industrial manufacturing of:

Enclomiphene citrate using said Enclomiphene base as a chemical synthetic intermediate and/or pharmaceutical products comprising said Enclomiphene.

Moreover, the suspensions of said known solid form of Enclomiphene does not filter very well, i.e. for large productions, the filtering time can be very long and the product shows consequently a lower chemical purity, especially for the content of the Cis-Clomiphene impurity.

SUMMARY OF INVENTION

The problem addressed by the present invention is therefore that of providing an improved solid form of Enclomiphene citrate which:

is thermodynamically more stable, complies with the stabilities studies under thermal/humidity conditions, is more soluble in water neutral or at acid pH values.

This problem is solved by a solid form of Enclomiphene citrate as outlined in the annexed claims, whose definitions are integral part of the present description.

As a further aspect, the problem is that of providing an improved solid form of Enclomiphene base with higher flowability, thus suitable for the industrial manufacturing form Enclomiphene citrate using said Enclomiphene base as a chemical synthetic intermediate and/or for the industrial manufacturing pharmaceutical products comprising said Enclomiphene. Moreover, another problem to be solved is the provision of a better solid form of Enclomiphene base, suspension of the which filters more quickly, thus, consequently, providing Enclomiphene (base) and then Enclomiphene citrate or Enclomiphene citrate having needle shaped crystal habit, all three of them with higher chemical purity, especially for the content of Cis-Clomiphene impurity.

Further features and advantages of the solid forms and processes according to the invention will result from the description hereafter reported of examples of realization of the invention, provided as an indication of the invention.

DESCRIPTION OF THE FIGURES

FIG. 7-B shows microscopy analysis, i.e. a picture with scale 50 μm (size of 50 μm in the upper side of the picture), of the crystals of Enclomiphene citrate crystallized from acetone, having non-needle shaped crystal habit.

FIG. 8-B shows microscopy analysis, i.e. a picture with scale 50 μm (size of 50 μm in the upper side of the picture), of the crystals of Enclomiphene citrate crystallized from ethanol, having needle shaped crystal habit.

FIG. 11-B shows microscopy analysis, i.e. a pictures with scale 50 μm (size of 50 μm in the up side of the picture), of the crystals of Enclomiphene (base) having prismatic crystal habit.

FIG. 12-B shows microscopy analysis, i.e. a picture with scale 50 μm (size of 50 μm in the up side of the picture), of the crystals of Enclomiphene (base) having non-prismatic crystal habit.

Figure 25:
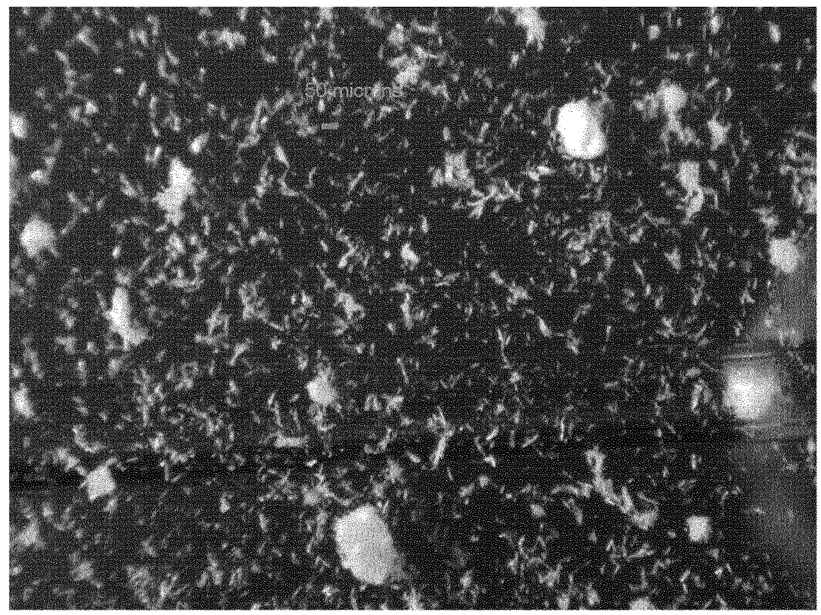
FIG. 25, shows the crystal habit of Enclomiphene citrate having needle crystal habit, as prepared in example 29. In particular, the pictures have been acquired using the following enlargements and having scale.
Figure 25:
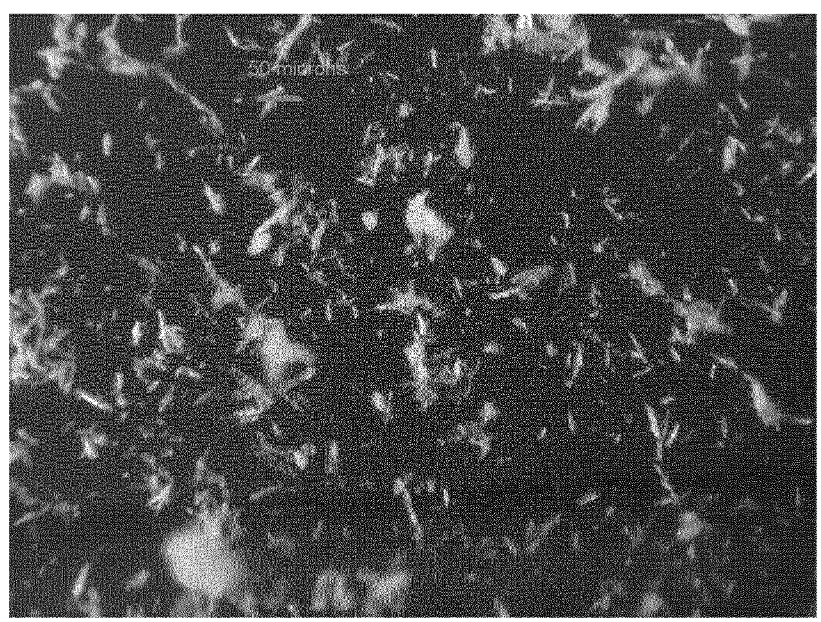

| | | |
|---|---|---|
| FIG. 25-A | enlargement: 4x | scale: 50 μm |
| FIG. 25-B1 | enlargement: 10x | scale: 50 μm |
| FIG. 25-B2 | enlargement: 10x | scale: 50 μm |
| FIG. 25-C | enlargement: 20x | scale: 50 μm |
| FIG. 25-D | enlargement: 50x | scale: 20 μm. |

Figure 26:
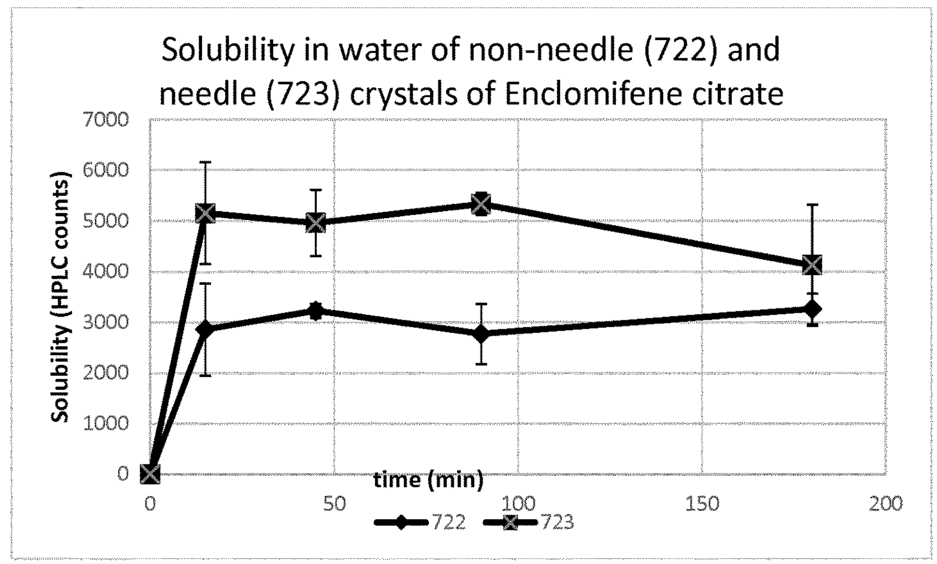

FIG. 26 shows the solubility in water of non-needle (722) and needle (723) crystals of Enclomifene citrate.

Figure 27:
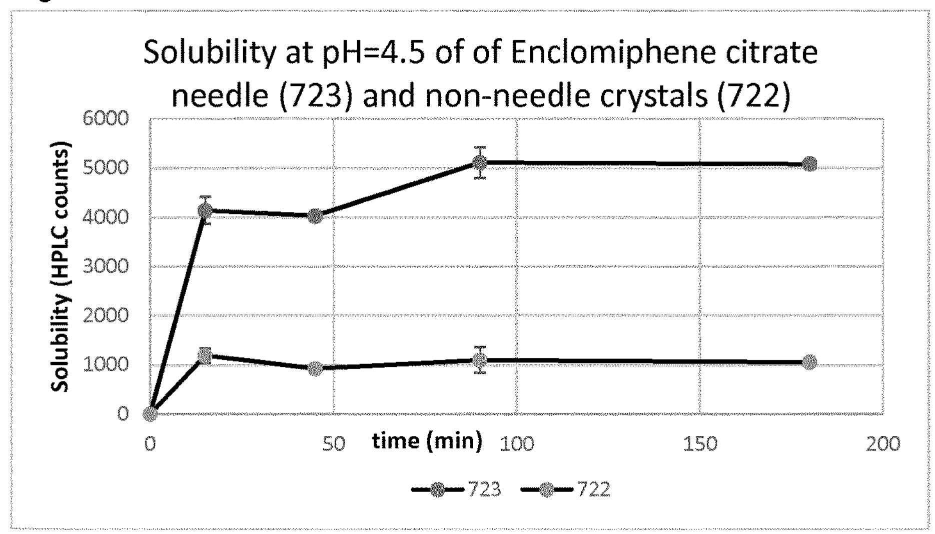

FIG. 27 shows the solubility at pH=4.5 of of Enclomiphene citrate needle (723) and nonneedle crystals (722).

Figure 28:
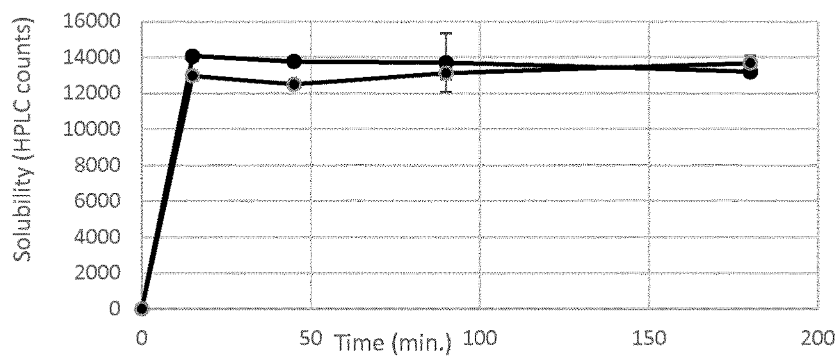

FIG. 28 shows solubility of Enclomiphene acetate at pH=4,5.

DESCRIPTION OF EMBODIMENTS

Here is described a process for the preparation of Clomiphene and salts thereof comprising the reaction of the mixture of geometric isomers of formula (V-E) and (V-Z) or salts thereof:

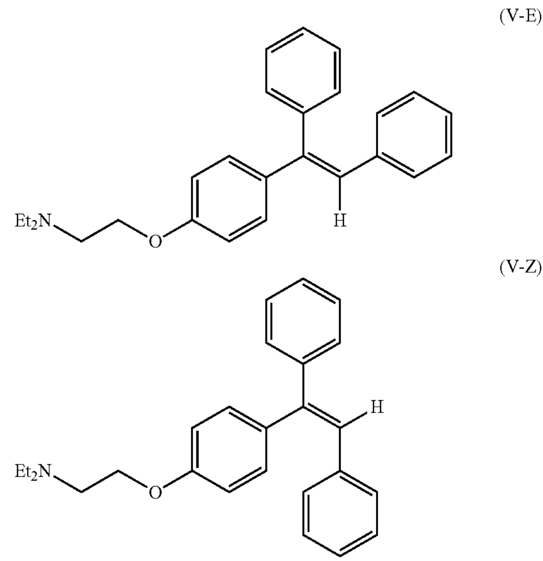

in an organic solvent with a chlorinating agent, characterized in that the reaction is performed in presence of acetic acid or trifluoroacetic acid.

It has been indeed surprisingly found that the prior art methods for the preparation of Clomiphene provide product containing two impurities, the first being trans-des-ethyl Chlomiphene, as monocitrate salt, having the following structure:

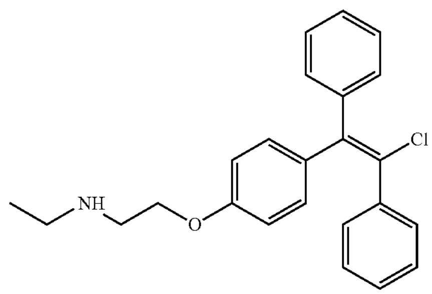 [SMILES: CCNCCOc1ccc(/C(=C(/Cl)c2ccccc2)c2ccccc2)cc1]

and the second being cis-des-ethyl Chlomiphene, as monocitrate salt, having the following structure:

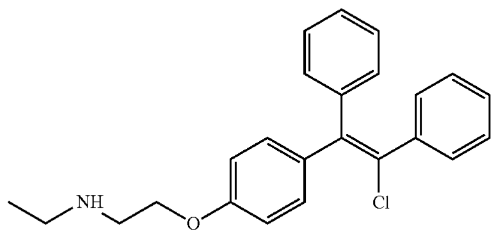 [SMILES: CCNCCOc1ccc(/C(=C(\Cl)c2ccccc2)c2ccccc2)cc1]

These impurities have relative retention times of 0.93 and 0.94 according to our analytical method (see example 10). According such analytical method these impurities have been found in amounts higher than 0.10%.

Moreover, it has been surprisingly found that both the impurities des-ethyl Clomiphene are generated during the chlorination reaction of the mixture of geometric isomers of formula (V-E) and (V-Z) or salts thereof:

(V-E)

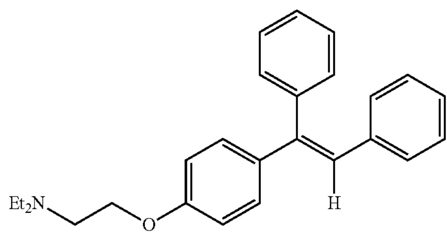

(V-Z)

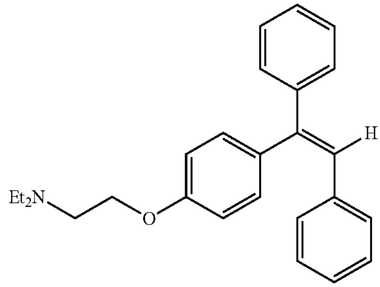

with a chlorinating agent and, surprisingly, the formation of said impurities can be inhibited by the presence of acetic acid or trifluoroacetic acid in the reaction mixture.

The main effect provided by the presence of acetic acid or trifluoroacetic acid in the chlorination reaction mixture of the compounds of formula (V-E) and (V-Z) is thus to limit or to avoid the formation of the impurities cis and trans des-ethyl Clomiphene, thus allowing the preparation of Clomiphene with an amount of such impurities lower than 0.10%.

The analytical method described in Example 10 allows the identification and quantification of the impurities cis and trans des-ethyl Clomiphene into Chlomiphene.

Moreover, as additional effect, the presence of acetic acid or trifluoroacetic acid during the chlorination reaction of the compounds of formula (V-E) and (V-Z) shifts the ratio trans-Clomiphene/cis-Clomiphene from a range of 60-70:40-30 to 75-85:25-15, thus favouring the preparation of trans-Clomiphene.

Furthermore, the presence of acetic acid or trifluoroacetic acid during the chlorination reaction of the compounds of formula (V-E) and (V-Z) provides the further effect of inhibiting the formation of chlorinated impurities such as the impurities named G and H of the European pharmacopeia being the two geometric isomers of the compound 2-[2-chloro-4-(2-chloro-1,2-diphenylethenyl)phenoxy]-N,N-diethylethanamine having the following structure:

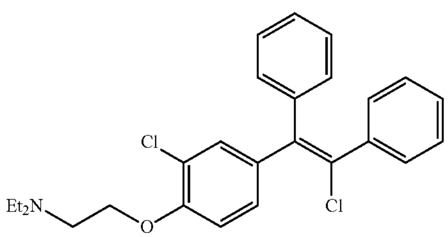

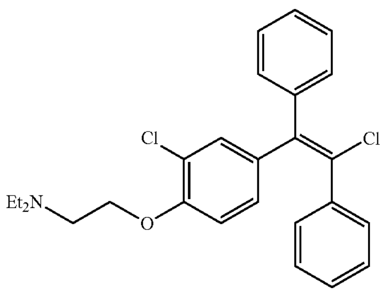

wherein the impurity G is the isomer having the higher-melting point while the impurity H is the isomer with lower-melting point.

The Clomiphene and salts prepared according to the process of the present invention is thus a mixture of trans-Clomiphene and cis-Clomiphene in ratio respectively from 75:25 to 99:1 and typically from 75:25 to 97:3.

The Clomiphene and salts prepared according to the process of the present invention is Clomiphene monocitrate, i.e. Clomiphene citrate (1:1), also simply named Clomiphene citrate, preferably Clomiphene in ratio trans-Clomiphene monocitrate/cis-Clomiphene monocitrate from 75:25 to 99:1.

The salts of the mixture of geometric isomers of formula (V-E) and (V-Z) can be salts with hydrochloric acid, hydrobromic acid, sulphuric acid, etc.

The preferred salt of the geometric isomers of formula (V-E) and (V-Z) is the hydrochloride salt.

The organic solvent of the process of the present invention can be an hydrocarbon solvent, a chlorinated solvent, acetate solvent, nitriles, etc.

An example of hydrocarbon solvent is Toluene, while examples of chlorinated solvents are chloroform, dichloromethane, chlorobenzene, etc. and examples of acetates are isopropyl acetate or ethyl acetate, while an example of nitrile solvent is acetonitrile.

The chlorinating agent of the process of the present invention is a typical chlorinated solvent used in the organic chlorination reaction, such as, for example, dichlorodimethylhydantoin, N-Chlorosuccinimmide, trichloroisocianuric acid, etc.

According to a preferred embodiment, the process of the present invention is carried out with an amount of acetic acid or trifluoroacetic acid which is comprised between 1 and 3 volumes, more preferably about 2 volumes.

1 Volume means, for example, 1 mL per 1 gram or 1 liter per 1 Kilogram.

According to a preferred embodiment of the process of the present invention, the amount of organic solvent is comprised between 5 and 11 volumes, more preferably about 8 volumes.

According to a more preferred embodiment, the process of the present invention is carried out with an amount of acetic acid or trifluoroacetic acid which is comprised between 1 and 3 volumes and the amount of organic solvent is comprised between 5 and 11 volumes, again more preferably, an amount of acetic acid or trifluoroacetic acid is about 2 volumes and the amount of organic solvent is about 8 volumes.

According to a preferred embodiment, the process of the present invention is carried out using methylene chloride as organic solvent.

It has been indeed found that, methylene chloride provides an higher ratio trans-Clomiphene:cis-Clomiphene, increasing the ratio, so that at the end of the chlorination reaction the ratio is comprised from 80:20 to 85:15.

Moreover, methylene chloride allows to perform the chlorination reaction at lower temperatures, for example at 25° C., while toluene for example requires 60° C. Performing the reaction at lower temperatures avoids the need to use a large excess of chlorination agent, which is indeed partially degraded operating at high temperatures. Thus, using methylene chloride as organic solvent to perform the chlorination reaction, it is achieved the advantage of reducing the amount of chlorination agent employed.

Moreover, it has been noticed that when the chlorination reaction of the compounds of formula (V-E) and (V-Z) is carried out in the mixture of dichloromethane and acetic acid or trifluoroacetic acid, the highest ratio of trans-Clomiphene: cis-Clomiphene is achieved, so that such process can be seen as a process for the preparation of trans-Clomiphene.

According to a preferred embodiment of the process of the present invention, the amount of methylene chloride is comprised between 5 and 11 volumes, more preferably about 8 volumes.

According to a preferred embodiment of the process of the present invention, the amount of acetic acid or trifluoroacetic acid is comprised between 1 and 3 volumes and the amount of methylene chloride is comprised between 5 and 11 volumes, more preferably is about 8 volumes.

According to a preferred embodiment of the process of the present invention, the amount of acetic acid or trifluoroacetic acid is about 2 volumes and the amount of methylene chloride is about 8 volumes.

According to a preferred embodiment of the process of the present invention, the reaction is performed at a temperature between 0° C. and 80° C., more preferably between 20° C. and 40° C., or at about 25° C. When the reaction is carried out at about 25° C. it is not required a large excess of chlorination reagent to complete the reaction.

According to a preferred embodiment of the process of the present invention, the amount of chlorinating agent is comprised in the range from 0.45 to 0.60 molecular equivalents, preferably from 0.48 to 0.52 mol. equivalents, again more preferably, about 0.51 mol. equivalents.

According to a preferred embodiment of the process of the present invention, the chlorinating agent is dichlorodimethylhydantoin since it is the chlorination agent that provides the best impurity profile.

According to a preferred embodiment of the process of the present invention, the reaction is carried out under anhydrous conditions. It has been indeed found that the presence of moisture or water is detrimental for the chlorination reaction since the presence of water provide the products containing the Impurity C of the European Pharmacopea having the following structure:

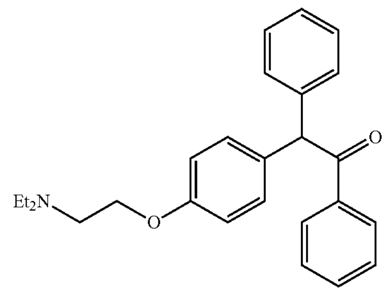

and the chloridrine impurity, as a mixture of two isomers, having the following structure:

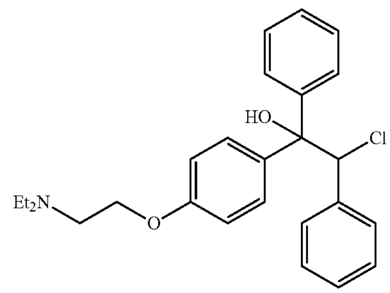

According to a preferred embodiment of the process of the present invention the amount of water should be lower than 500 ppm in the chlorination reaction mixture to guarantee that the amount both impurity C and chloridrine impurities are each lower than 0.10% in the final product Clomiphene.

According to a more preferred embodiment of the process of the present invention the amount of water should be lower than 250 ppm in the chlorination reaction mixture.

The molar yield of the process according to the present invention is comprised between 92% and 96%, being typically about 94%.

The product Clomiphene prepared according to the process of the present invention contains less than 0.06% of each impurity des-ethyl Chlomiphene and less than 0.06% of impurities G and H according to the European Pharmacopoeia.

The process of the present invention, optionally, further comprises the step of preparation of the compound of formula (VI):

(VI)

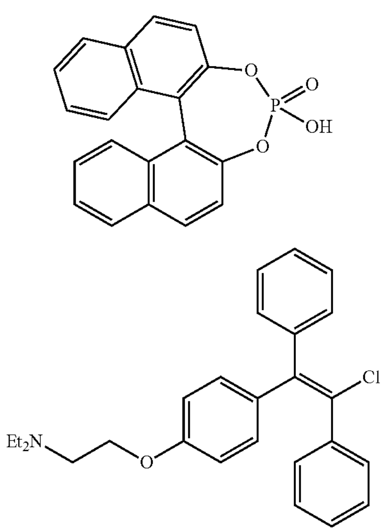

by addition of racemic binaphthyl-phosphoric acid to the reaction mixture at the end of the chlorination reaction.

In particular, at the end of the chlorination reaction, racemic binaphthyl-phosphoric acid, i.e. the (±)-1,1'-Binaphthyl-2,2'-diyl hydrogenphosphate, can be added to the reaction mixture thus carrying out the whole process one-pot.

Also single enantiomer of the binaphthyl-phosphoric acid, i.e. the (+)-1,1'-Binaphthyl-2,2'-diyl hydrogenphosphate or (+1,1'-Binaphthyl-2,2'-diyl hydrogenphosphate can be added at the end of the chlorination reaction achieving substantially the same results obtained using the racemic form, which is the one economically more advantageous.

The addition of racemic binaphthyl-phosphoric acid to the reaction mixture causes the precipitation of the salt of trans-clomiphene with racemic binaphthyl-phosphoric acid. Such salt shows a ratio trans-clomiphene/cis-clomiphene from 90:10 to 98:2 (see examples 3a-3d).

The salt of trans-clomiphene with racemic binaphthyl-phosphoric acid can be optionally further purified by preparation of the trans-clomiphene base and re-precipitating the salt of trans-clomiphene with racemic binaphthyl-phosphoric acid by addition of racemic binaphthyl-phosphoric acid to the trans-clomiphene base in an organic solvent. Such salt of trans-Clomiphene contains less than 0.15% (HPLC A % of the Cis-Clomiphene) (see examples 4a-4c).

Figure 5:
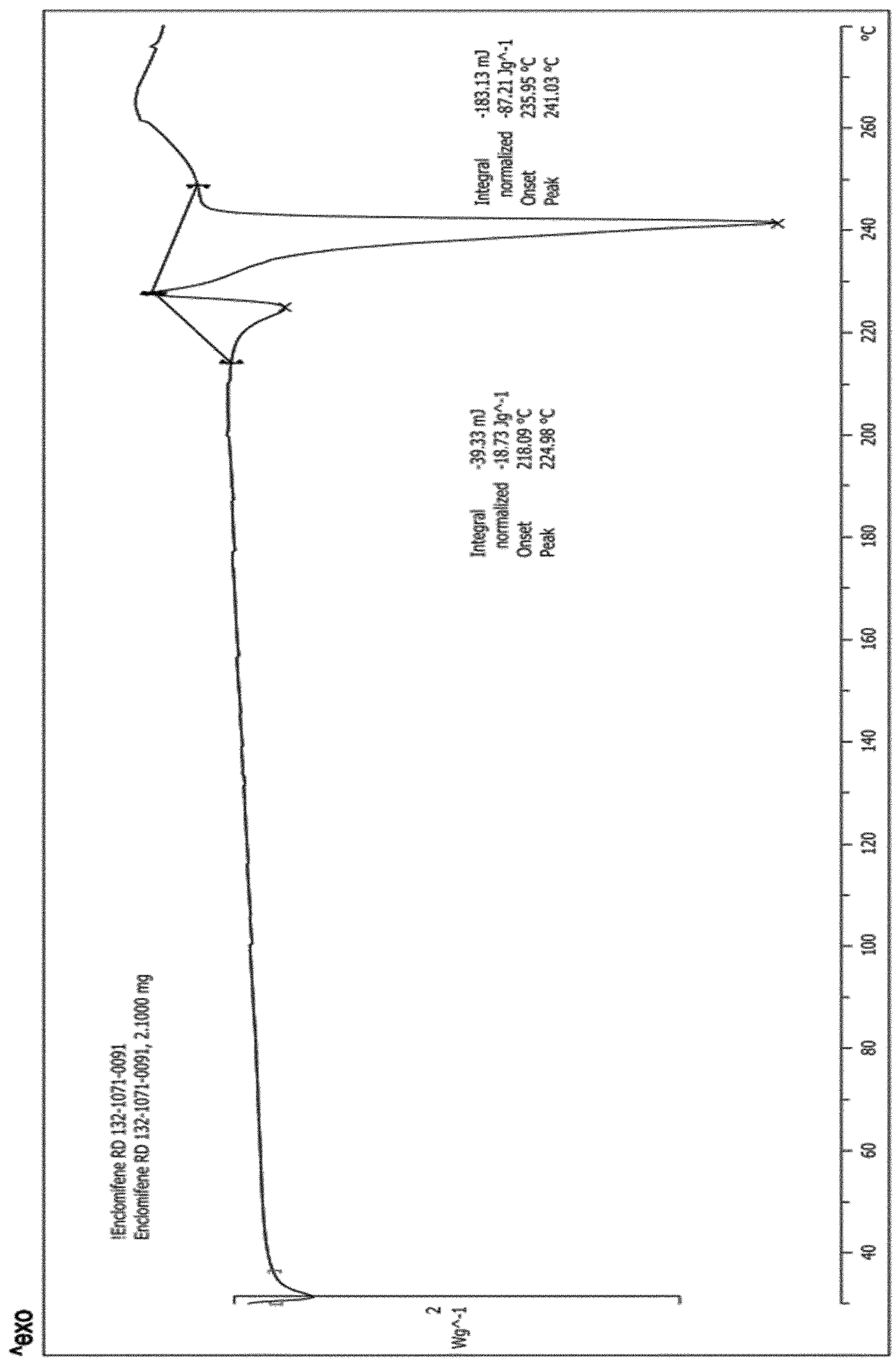
FIG. 5 shows the DSC curve of trans-Clomiphene salt with racemic binaphthyl-phosphoric acid of formula (VI).

The salt of trans-clomiphene with racemic binaphthyl-phosphoric acid shows a melting point of 218° C. as determined by DSC on set point (see example 5 and FIG. 5), and has the following HPLC analysis (A/A %): 98.95% E-Chlomiphene, 0.10% Z-Clomiphene (not considering in the integration the peak of binaphthyl-phosphoric acid). The trans configuration has been confirmed by 2D-NMR analysis. This experimental melting point is substantially the same of that disclosed in Example 31 of U.S. Pat. No. 3,848,030 (220-222° C.), thus confirming the wrong assignation of the geometric isomerism in said document and also confirming that the salt of trans-Clomiphene with racemic binaphthyl-phosphoric acid is already known since 70's, including the polymorphic solid form isolated from methanol having m.p. 220-222° C. Moreover, by comparison of the melting points 218° C. (with HPLC purity 98.95%) versus 220-222° C., it appears that the salt of trans-clomiphene with racemic binaphthyl-phosphoric acid disclosed in U.S. Pat. No. 3,848,030 was a solid having a relatively high chemical purity (likely around 99%).

The salt of trans-clomiphene with racemic binaphthyl-phosphoric acid, optionally purified or not, according to the teaching of the previous paragraph, can be converted in the trans-Clomiphene free base according to the teaching of U.S. Pat. No. 3,848,030, second part of example 31, and then converted to the trans-Clomiphene monocitrate salt by addition of citric acid in acetone. The trans-Clomiphene monocitrate salt thus prepared contains less than 0.4% of Cis-Clomiphene (HPLC A/A %) (see examples 6a-6c, 7), in particular from 0.40% to 0.04% of cis-Clomiphene.

The process of the present invention can further comprise the step of preparation of the mixture of geometric isomers of formula (V-E) and (V-Z) or salts thereof:

(V-E)

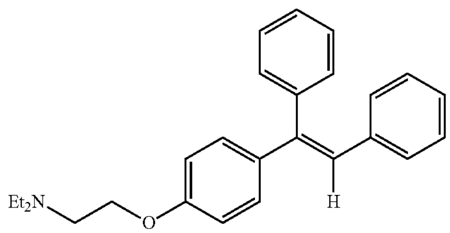

(V-Z)

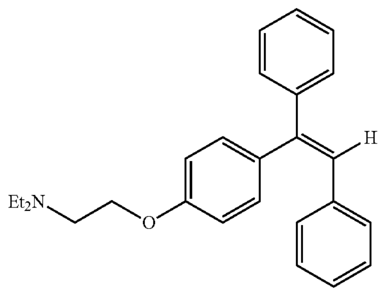

by dehydration reaction of the compound of formula (VII):

(VII)

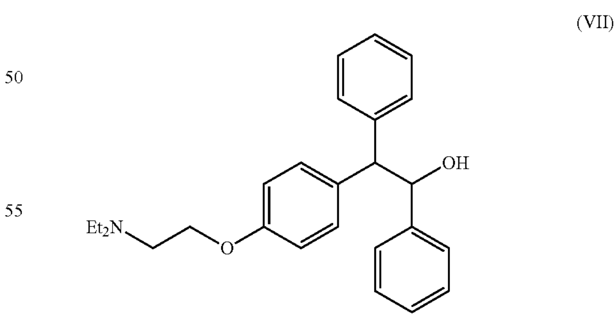

The dehydration reaction of the compound of formula (VII) is typically carried out in an organic solvent in presence of an acid.

The dehydration reaction is preferably carried out with hydrochloric acid in toluene. Therefore, the compounds of formula (V-E) and (V-Z) of the present invention are typically in form of hydrochloride salts.

Since the process of the present invention provides Clomiphene having a ratio of trans-Clomiphene and cis-Clomiphene well in favour of the trans-Clomiphene, the process of the present invention can be seen as a process for the preparation of trans-Clomiphene.

Thus, the present invention also relates to a process for the preparation of trans-Clomiphene and salts thereof comprising the reaction of the mixture of geometric isomers of formula (V-E) and (V-Z) or salts thereof:

(V-E)

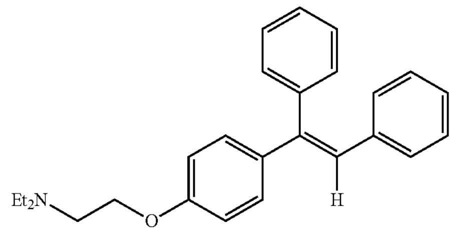

(V-Z)

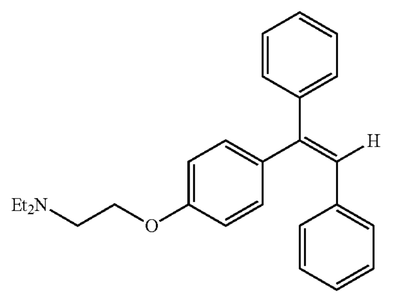

in an organic solvent with a chlorinating agent, characterized in that the organic solvent is methylene chloride and the reaction is performed in presence of acetic acid or trifluoroacetic acid.

The combination of methylene chloride as solvent and the presence of acetic acid or trifluoroacetic acid in the chlorination reaction of the mixture of geometric isomers of formula (V-E) and (V-Z) or salts thereof, indeed, provides the higher ratio trans-Clomiphene versus cis-Clomiphene, so that this combination of features is well suitable for a process for the preparation of trans-Clomiphene.

The process according to the present invention provides preferably Clomiphene as a mixture of trans-Clomiphene and cis-Clomiphene in ratio from 75:25 to 99:1.

Acetic acid or trifluoroacetic acid can therefore be conveniently used to carry out the chlorination reaction with a chlorinating agent of the mixture of geometric isomers of formula (V-E) and (V-Z) or salts thereof:

(V-E)

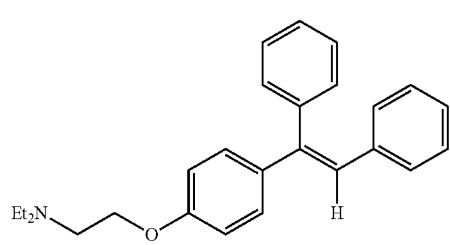

-continued (V-Z)

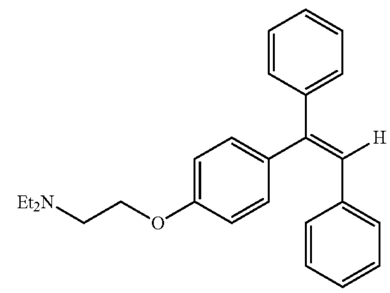

to provide Clomiphene and salts thereof.

The process of the present invention can be carried out with anyone of the combinations of preferred embodiments above described.

During the development of the process for the preparation of trans-Clomiphene it has been surprisingly discovered a stable solid form of trans-Clomiphene monocitrate.

The term monocitrate means 1 mole of citric acid for 1 mole of trans-Clomiphene. Thus, trans-Clomiphene monocitrate can also be named trans-Clomiphene citrate or trans-Clomiphene citrate (1:1) or Enclomifene citrate (1:1) which is also named simply Enclomiphene citrate.

In particular, it has been found a process for the preparation of a solid form of trans-Clomiphene monocitrate of formula:

(III)

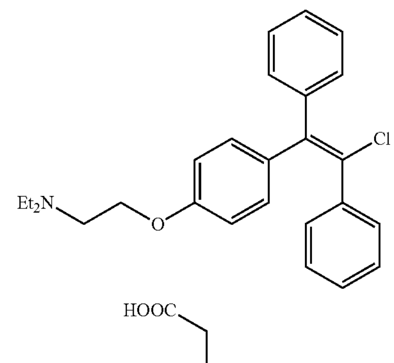

by treatment of trans-Clomiphene in an organic solvent with citric acid monohydrate.

The following scheme shows the process for the preparation of a solid form of Trans-Clomiphene monocitrate:

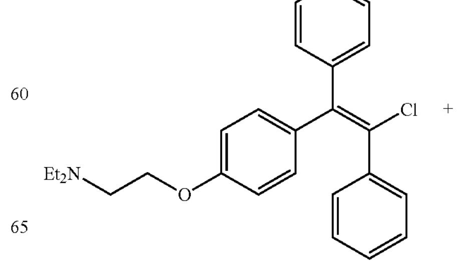

-continued

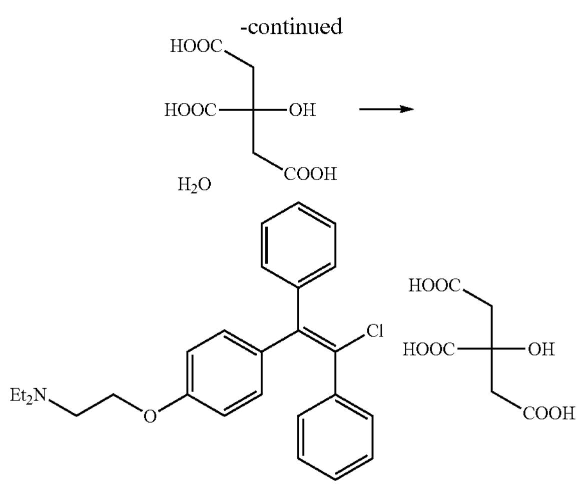

The organic solvent to carry out such a process is a ketone solvent such as for example acetone or methylethylketone or an acetate solvent such as ethylacetate or isopropyalcetate, acetone being preferred.

Figure 2:
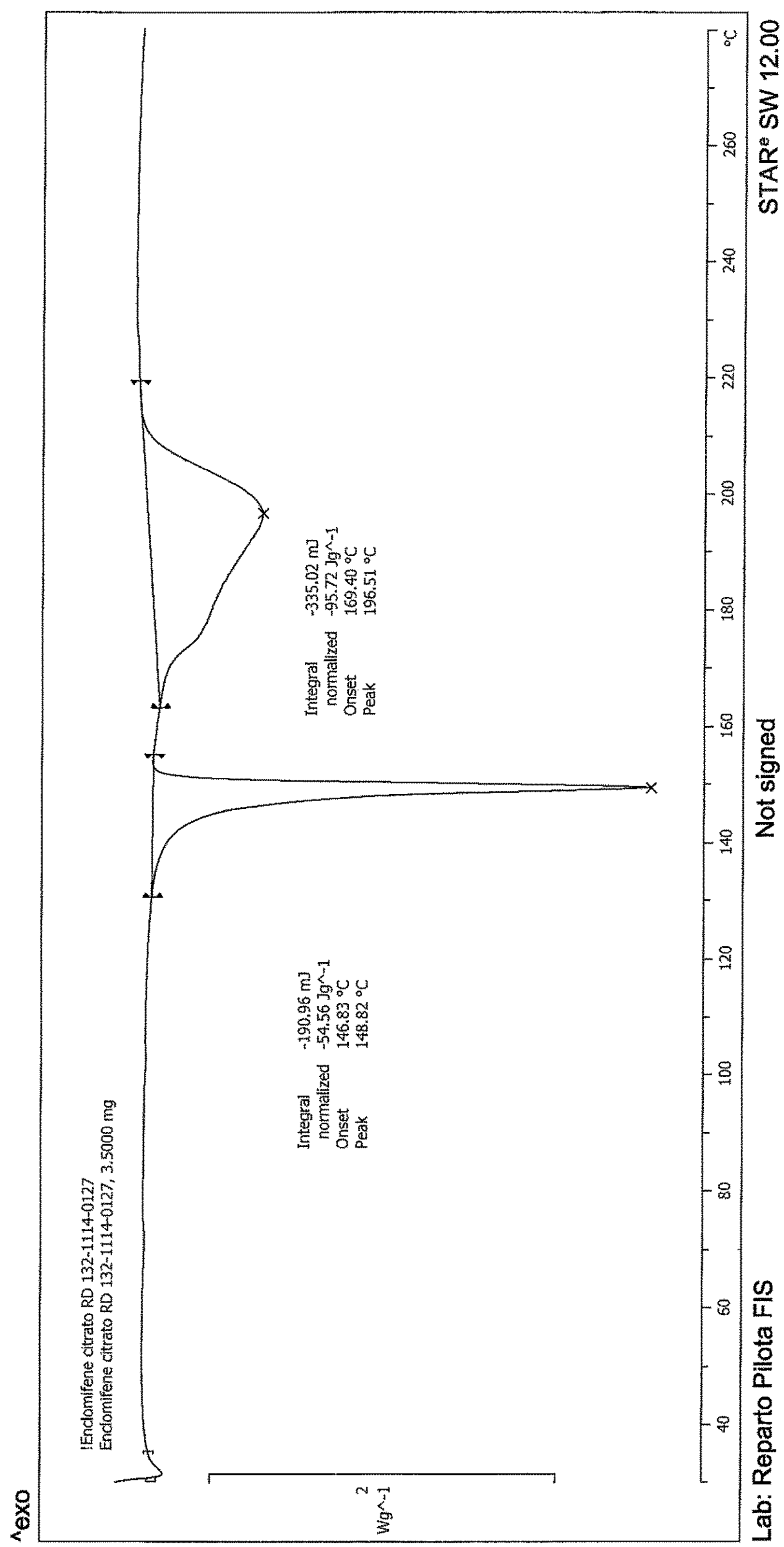
FIG. 2 shows the DSC curve of the solid form of trans-Clomiphene monocitrate crystallized from acetone.

The solid form of trans-Clomiphene monocitrate obtained by such process has a melting point of about 147° C., measured by DSC (onset) (See FIG. 2).

Moreover, the solid form of trans-Clomiphene monocitrate obtained by such process shows a peak at about 149° C., as measured by DSC (See FIG. 2).

The solid form of trans-Clomiphene monocitrate obtained by such process exhibits a characteristic X-ray powder diffraction pattern with characteristic peaks expressed in 2-Theta values (2θ): 5.69 (s), 9.64 (s), 10.86 (m), 11.45 (s), 12.64 (vs), 14.75 (m), 16.35 (m), 17.02 (m), 18.69 (m), 20.51 (m), 21.68 (m), 23.58 (m), 24.82 (m), 31.2 (w); wherein (vs)=very strong intensity; (m)=medium intensity; (w)=weak intensity.

The solid form of trans-Clomiphene monocitrate exhibits a characteristic X-ray powder diffraction pattern with stronger characteristic peaks expressed in 2-Theta values (2θ) at: 5.69 (s), 9.64 (s), 11.45 (s), 12.64 (vs).

The solid form of trans-Clomiphene monocitrate obtained by such process is a crystalline solid.

The solid form of trans-Clomiphene monocitrate obtained by such process has non-needle-shaped crystal.

The solid form of trans-Clomiphene monocitrate obtained by such process has a melting point of about 147° C. Said melting point is well different from that disclosed in literature for the trans-Clomiphene monocitrate obtained using anhydrous citric acid in Ethanol and diethyl ether and as disclosed in example 31 of U.S. Pat. No. 3,848,030, being 133-135° C.

By comparison of the melting points it appears that the solid form of trans-Clomiphene monocitrate of the present invention prepared using citric acid monohydrate is different from the known solid form of anhydrous trans-Clomiphene prepared using anhydrous citric acid, and, it appears that the solid form of the invention is thermodynamically more stable than the known form since it has higher melting point.

It has been found that reacting trans-Clomiphene with citric acid monohydrate in an organic solvent, a new solid form of Trans-Clomiphene monocitrate, maybe an hydrate form, (for example an hydrate having stoichiometry ratio of Trans-Clomiphene/citric acid/water of 3:3:2), is obtained by such process and said form appears to be stable toward the humidity.

The solid form of trans-Clomiphene monocitrate obtained by such process shows a Karl Fischer (K.F.) value of about 2.0%.

The solid form of trans-Clomiphene monocitrate of the invention can be prepared dissolving trans-Clomiphene in an organic solvent and adding citric acid monohydrate.

When trans-Clomiphene is dissolved in an organic solvent and anhydrous citric acid is added, then trans-Clomiphene monocitrate as anhydrous form is prepared (see example 7).

According to a preferred embodiment, the organic solvent for the preparation of the solid form of trans-Clomiphene monocitrate is acetone.

According to a preferred embodiment, the process for the preparation of the solid form of trans-Clomiphene monocitrate is carried out at temperature comprised between 20° C. and 100° C., preferably between 40° C. and 60° C., more preferably at about 50° C.

According to a preferred embodiment, the process for the preparation of the solid form of trans-Clomiphene monocitrate is carried out adding citric acid monohydrate, as solid or in solution of an organic solvent, to a solution of trans-Clomiphene in an organic solvent.

According to a preferred embodiment of the process for the preparation of the solid form of trans-Clomiphene monocitrate, the amount of citric acid monohydrate used is comprised between 1.1 and 1.3 mol. equivalents.

According to a preferred embodiment of the process for the preparation of the solid form of trans-Clomiphene citrate, the starting material trans-Clomiphene comprises less than 5% (HPLC A %) of cis-Clomiphene, preferably less than 2% cis-Clomiphene.

The process of the present invention for the preparation of the solid form of trans-Clomiphene monocitrate can be carried out with anyone of the combinations of preferred embodiments above described.

Thus, citric acid monohydrate can be used for the preparation of the solid form of trans-Clomiphene monocitrate according to the process of the present invention.

Pharmaceutical compositions comprising the solid form of trans-Clomiphene monocitrate according to the present invention can be prepared according to the teaching of example 3 of WO2014/031177A1.

Therefore, the solid form of trans-Clomiphene monocitrate of the present invention can be used in medicine, in particular, can be used for the treatment ovulatory dysfunction or polycystic ovary syndrome.

During further experimental work for developing an efficient process for the preparation of Enclomiphene citrate, mainly with the aim of increasing the molar yield and purity of the final step of crystallization of the product, instead to crystallize the product Enclomiphene citrate from an acetate solvent or from a ketone solvent, in particular from acetone, it has been accidentally carried out the crystallization of the Enclomiphene citrate from ethanol, i.e. ethanol without other solvents. Such an experiment has unexpectedly provided a solid having a different appearance and improved stability and solubility properties in comparison with Enclomiphene citrate obtained from the crystallization using acetone, already above described, or with Enclomiphene citrate solid form discloses in prior art.

In particular, crystallizing or recrystallizing Enclomiphene citrate from ethanol, without other solvents, it is possible to prepare Enclomifene citrate having needle crystals, while Enclomiphene citrate obtained from the crystallization using acetone, as said above, has non-needle-shaped crystals.

Thus, an object of the present invention is Enclomiphene citrate of formula (III):

(III)

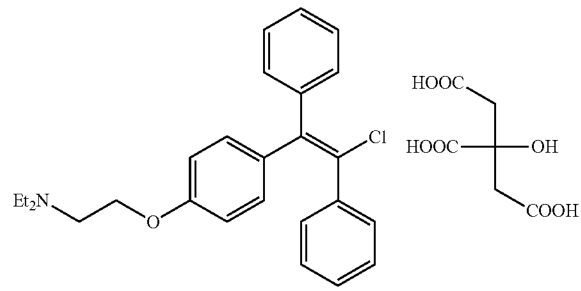

having needle shaped crystal habit.

A crystal having needle shape is a thin, cylindrical crystal, often, but not necessarily, with a sharp point on the end.

The different crystal habit of the two solid forms, one obtained crystallizing from acetone (non-needle crystals) and the other from only ethanol (needle crystals) was well evident by microscopy analysis.

Figure 7:
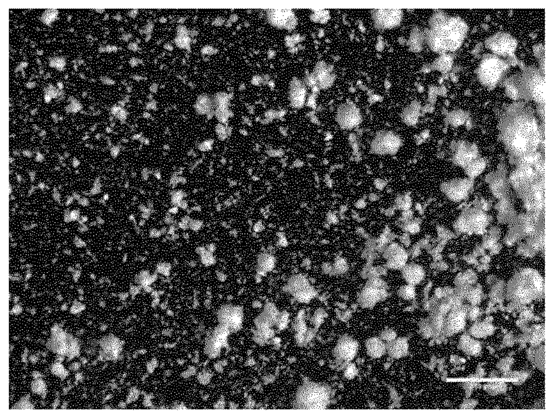
FIG. 7 shows microscopy analysis, i.e. a picture with scale 500 μm (size of 500 μm in the bottom and right side of the picture), of crystals of Enclomiphene citrate having non-needle crystal habit, crystallized from acetone.
Figure 8:
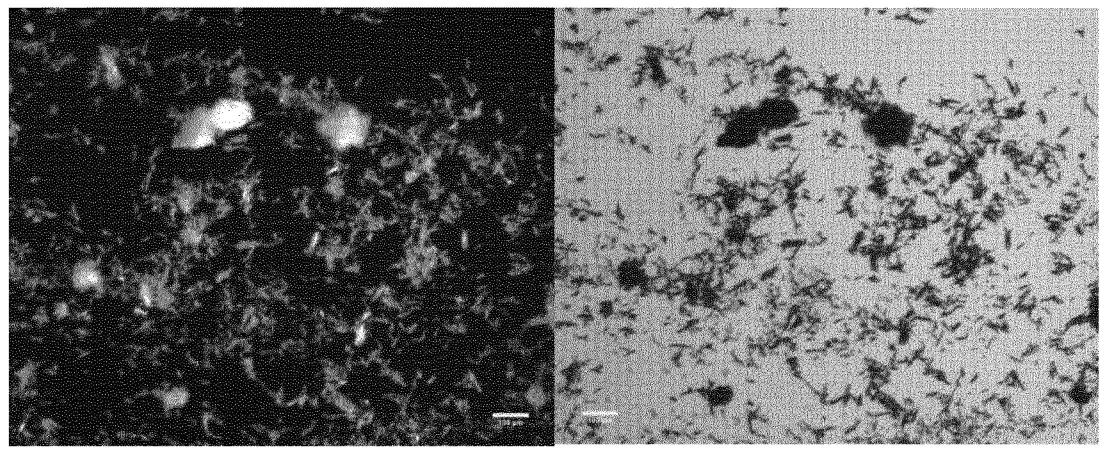
FIG. 8 shows microscopy analysis, i.e. a pictures with scale 100 μm (size of 100 μm in the bottom of the picture), of the crystals of Enclomiphene citrate having needle crystals, crystallized from ethanol. Picture on the left side is acquired with reflected light (left) while picture on the right side is acquired with transmitted light.

Indeed, the microscopy analysis, and in particular, the comparison of pictures in FIGS. 7 and 8 and FIGS. 7-BIS and 8-BIS acquired by microscopy analysis provides a better further evidence of the different crystal habit of the two forms (see example 13 and FIG. 7, 8, 7-BIS, 8-BIS).

Moreover, FIG. 25 clearly shows the crystal habit of Enclomiphene citrate having needle shaped crystal habit.

From the XPRD analysis (see example 15 and FIGS. 9 and 10) it appears that the solid form of Enclomiphene citrate prepared form ethanol appears to be or resembles to the same polymorph solid form of Enclomiphene citrate prepared form acetone or it is similar polymorph, since the position of the XPRD peaks is substantially the same, although some peak intensities are different, but the two solid forms shows two well different crystal habit forms, one being respectively needle crystals and the second being non-needle crystals.

Thus, although it is not clear if the two solid forms are two different polymorphs or not, it is however clear that the two solid forms are two different crystal forms since they show a well different crystal habit.

In particular, Enclomiphene citrate having needle shaped crystals habit has a characteristic X-ray powder diffraction pattern with characteristic peaks expressed in 2-Theta values (2θ) at: 5.8 (vs), 11.5 (vs); wherein (vs)=very strong intensity.

More in particular, Enclomiphene citrate having needle shaped crystals habit has a characteristic X-ray powder diffraction pattern with characteristic peaks expressed in 2-Theta values (2θ) at: 5.8 (vs), 11.5 (vs), 12.7 (s), 14.9 (s) and 24.9 (s); wherein (vs)=very strong intensity; (s)=strong intensity.

Again more particularly, Enclomiphene citrate having needle shaped crystals habit has a characteristic X-ray powder diffraction pattern with characteristic peaks expressed in 2-Theta values (2θ) at: 5.8 (vs), 9.7 (m), 10.9 (m), 11.5 (vs), 12.7 (s), 14.9 (s), 17.1 (m), 20.6 (m), 21.8 (m), 23.6 (m), 23.7 (m) and 24.9 (s); wherein (vs)=very strong intensity, (s)=strong intensity, (m)=medium intensity.

The meanings given above for (vs)=very strong intensity, (s)=strong intensity, (m)=medium intensity refer to the following relative intensities percentages:

(vs)=very strong intensity means Rel. Int [%] in the range 81-100, (s)=strong intensity means Rel. Int [%] in the range 80-40, (m)=medium intensity means Rel. Int [%] in the range 39-20.

The K.F. analysis of Enclomiphene citrate having needle crystals provides a values of about 2%.

Figure 6:
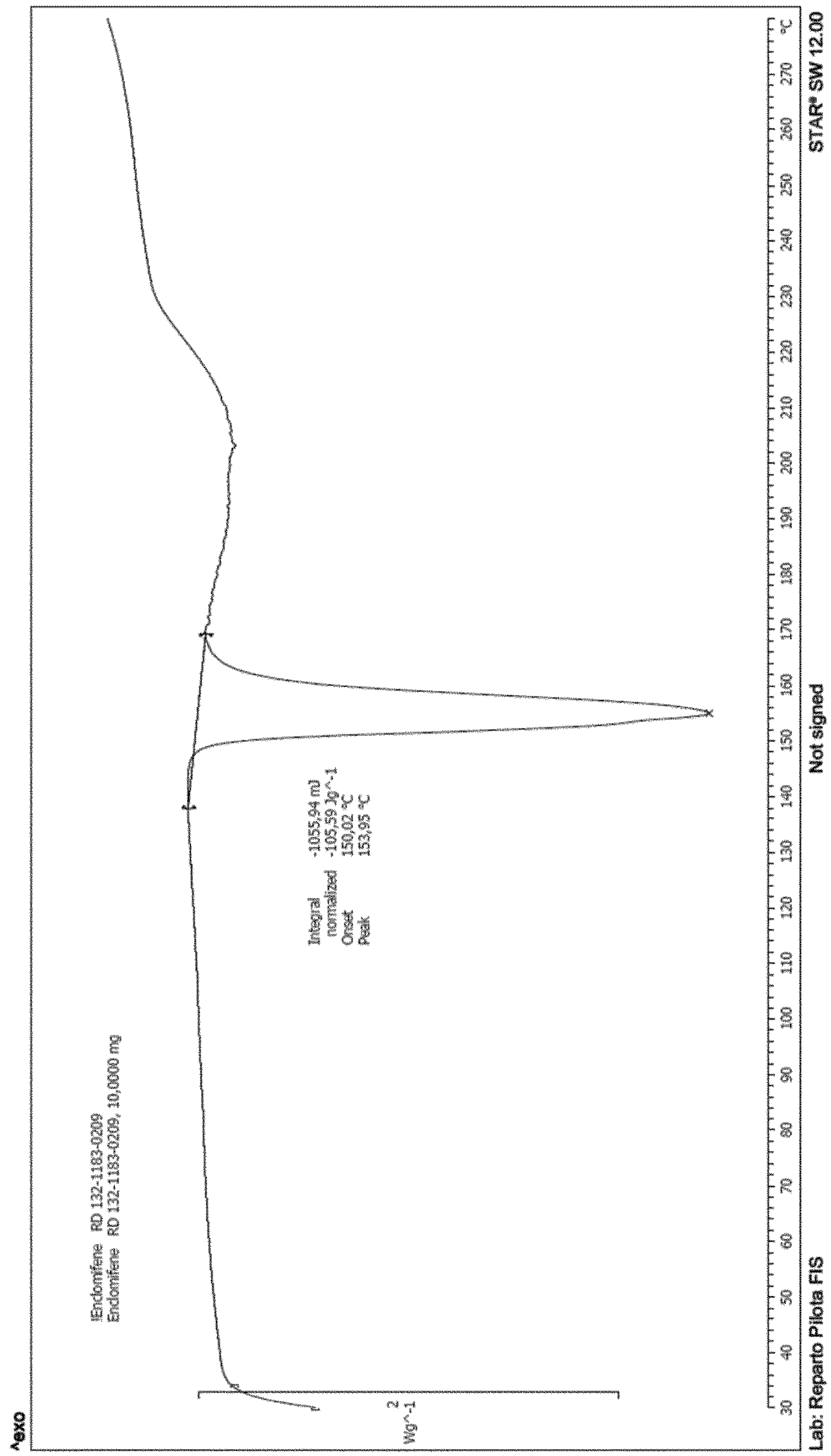
FIG. 6 shows the DSC curve of the solid form of Enclomiphene citrate having needle crystals, crystallized from ethanol.

The comparison of the DSC curves of FIG. 2 and FIG. 6 provides a clear evidence of the different thermal behavior of the two solid forms of Enclomiphene citrate having two different crystal habits, respectively non-needle and needle crystals, maybe of the same polymorphic form.

The solid form of trans-Clomiphene monocitrate, i.e. Enclomiphene citrate having needle shaped crystal habit, obtained crystallizing the product from ethanol, has a melting point of 150° C. as measured by DSC (onset) (See FIG. 6).

Moreover, the solid form of Enclomiphene citrate having needle shaped crystal habit, obtained crystallizing the product from ethanol, shows a peak at 154° C. as measured by DSC (See FIG. 6).

Thus, Enclomiphene citrate having needle shaped crystal habit has a melting point of 150° C. as measured by DSC (onset).

Moreover, Enclomiphene citrate having needle shaped crystal habit shows a peak at 154° C. as measured by DSC.

Thus, Enclomiphene citrate having needle shaped crystal habit has a melting point of 150° C. which is higher of that of Enclomiphene citrate having non-needle shaped crystal habit, being 147° C., both measured by DSC (onset) (See respectively FIG. 6 and FIG. 2).

Such a different thermal behavior is also confirmed by the different peak in the DSC analysis: Enclomiphene citrate having needle shaped crystal habit shows a peak at 154° C., an higher temperature compared with the peak at 149° C. of Enclomiphene citrate having non-needle shaped crystal habit.

The above said DSC comparative study give thus evidence that the crystalline habit of Enclomiphene citrate being needle shaped crystals is thermodynamically more stable of the crystal habit being non-needle shaped crystals, since the melting point of the first is higher than that of the latter (150° C. versus 147° C.), and both the forms having higher melting points compared with those disclosed in literature of 133-135° C. and 138-139° C. for Enclomiphene citrate.

It should further noticed that, as discussed above, the polymorph having crystalline habit non-needle and m.p. of 147° C., was already identified to be the thermodynamically more stable polymorphic form of Enclomiphene citrate. Thus, Enclomiphene citrate having needle crystals is the solid form having an highest thermal stability. This is confirmed by the highest melting point shown by Enclomiphene citrate having needle crystals.

The higher thermal stability of Enclomiphene citrate having needle crystals was indeed confirmed by comparative stability studies, indeed such a crystal form remains thermodynamically stabile while the solid having crystalline habit non-needle and m.p. of 147° C., after 17 days at room temperature and 95% RH fails the stability studies. In particular, after 17 and 30 days at room temperature and 95% RH the intensities of the peaks of the XPRD diffractograms have a very significant drop, respectively to about 50% of the initial intensity and, after 30 days, about 30% of the initial intensity. Said analysis allows to hypothesize an amorphization of a part of the crystal. Such a behavior is in line also with the hygroscopicity study and behavior exemplified in FIG. 18, wherein Enclomiphene having non-needle crystals absorbs relevant amounts of water when exposed at values of humidity higher than 65% RH.

Considering the regulatory requirements to be complied, it is clear that the enhanced thermal stability of Enclomiphene citrate having needle crystals is the key solid form for supplying a product complying with the pharmaceutical requirements related to the stability, including the hygroscopicity behavior.

Enclomiphene citrate having needle crystalline habit, being the thermodynamically more stable solid form, exhibits therefore better storage stability and can be more easily formulated into pharmaceutical compositions of medicaments.

The higher thermal stability of Enclomiphene citrate having needle shape crystal habit is not the only one advantageous property of such product.

Indeed, Enclomiphene citrate having needle shaped crystal habit, i.e. Enclomiphene citrate needle crystals, crystallized from ethanol and having m.p. of 150° C. (by DSC (onset)), shows a much higher solubility in water, especially in water at pH 4.5, in comparison to Enclomiphene citrate non-needle shaped crystal habit, i.e. Enclomiphene citrate crystallized from acetone.

In particular, example 17 provides a clear evidence that Enclomiphene citrate having needle shaped crystal habit shows a solubility in water almost double compared with Enclomiphene citrate having non-needle shaped crystal habit, and the solubility at pH 4.5 is four times higher compared with the non-needle shaped crystal habit.

Such solubility study gives the indication that Enclomiphene citrate having needle shaped crystal habit has higher bioavailability compared with Enclomiphene citrate non-needle shaped crystal habit.

Thus, Enclomiphene citrate having needle shaped crystal habit of the present invention is also suitable for fast-release pharmaceutical composition of Enclomifene citrate.

Figure 18:
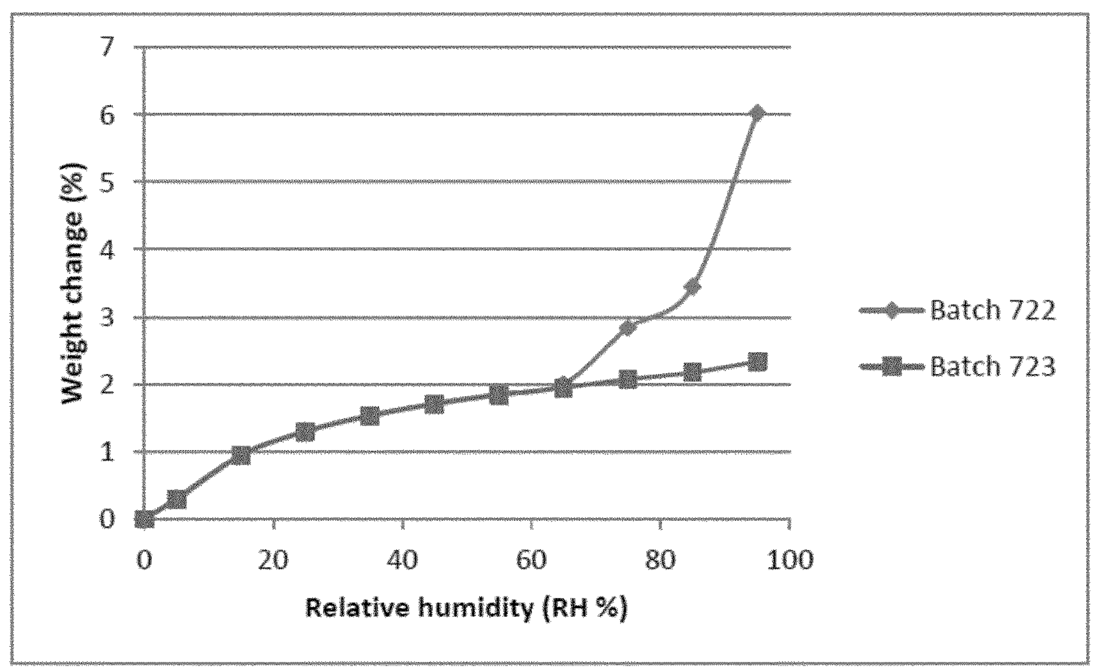
FIG. 18 shows the sorption isotherm comparison of batch 722, i.e. Enclomiphene citrate having non-needle crystals, as crystallized from acetone, m.p. 148° C. (DSC (onset) and batch 723, i.e. Enclomiphene citrate having needle crystals, crystallized from ethanol, m.p. 153° C. (DSC (onset).

Moreover, Enclomiphene citrate having needle shaped crystal habit, i.e. Enclomiphene citrate crystallized from ethanol shows much better hygroscopicity behavior, especially in comparison to Enclomiphene citrate having non-needle shaped crystal habit obtained by crystallization form acetone (see example 24 and FIG. 18).

Another object of the present invention is thus a process for the preparation of Enclomifene citrate of formula (III):

(III)

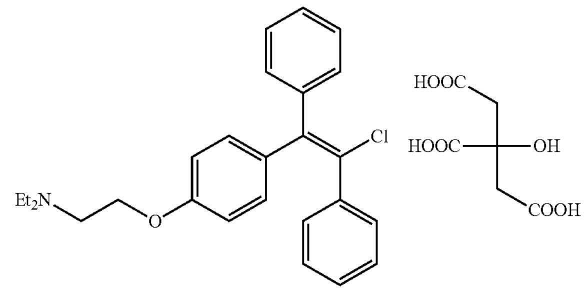

having needle shaped crystal habit as described above, by addition of citric acid to a solution of Enclomiphene in an organic solvent, wherein said organic solvent consist in only ethanol.

The addition of citric acid can be carried out by addition of solid citric acid or, alternatively and preferably, by addition of a solution of citric acid in ethanol to a solution of Enclomiphene in ethanol.

The solution of citric acid in ethanol can be made by dissolving said compounds in a volume from 5 to 20 volume of ethanol.

The solution of Enclomiphene in an organic solvent, consist in only ethanol and Enclomiphene.

Ethanol can be pure ethanol or absolute ethanol, absolute ethanol being the preferred one.

The solution of Enclomiphene in ethanol can be realized by solubilization of Enclomiphene in a volume of ethanol comprised between 2 and 30 volumes, preferably between 5 and 20 volumes, more preferably 10 volumes.

The addition of citric acid can be preferably carried out at a temperature comprised between 0° C. and 25° C.

According to a preferred embodiment of said process for the preparation of Enclomiphene citrate having needle shaped crystal habit, the Enclomiphene to be converted into Enclomiphene citrate is prepared starting from E-Clomiphene BPA salt, i.e. from Enclomiphene salt with racemic binaphthyl-phosphoric acid of formula (VI). Example 14 exemplify such an embodiment.

Another object of the present in invention are pharmaceutical compositions comprising Enclomiphene citrate having needle shaped crystal habit and one or more pharmaceutical acceptable excipients.

Examples of suitable pharmaceutical compositions comprising Enclomiphene citrate having needle shaped crystal habit are those disclosed in WO2006102232A2, WO2010054248A1, WO2013020017A1, WO2013123218A1, WO2013130832A1, example 3 of WO2014031177A1 or WO2014070523A1 with the difference that Enclomiphene citrate having needle shaped crystal habit is used instead of the disclosed Enclomiphene having non-needle shaped crystal habit.

Another object of the present in invention are fast-release pharmaceutical compositions comprising Enclomiphene citrate having needle shaped crystal habit and one or more pharmaceutical acceptable excipients.

Enclomiphene citrate having needle shaped crystal habit can be used in medicine.

In particular, Enclomiphene citrate having needle shaped crystal habit can be used in the treatment ovulatory dysfunction or polycystic ovary syndrome.

An alternative process for the preparation of Enclomiphene citrate of formula (III):

(III)

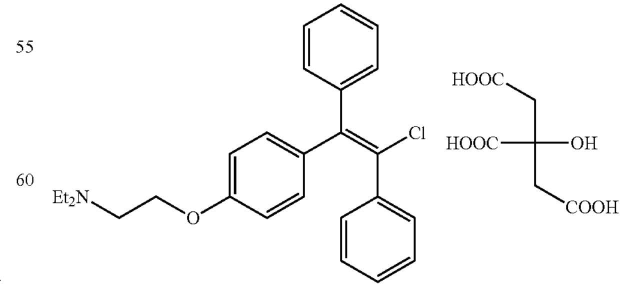

having needle shaped crystal habit, comprises the following steps:

a) preparation of Enclomiphene having prismatic shaped crystal habit and/or having median value (D50) of the particle size distribution comprised in the range from 100 μm to 500 μm, by crystallization of the Enclomiphene from ethanol, b) conversion of Enclomiphene of the step a) to Enclomiphene citrate having prismatic shaped crystal habit according to the process above described, i.e., by addition of citric acid to a solution of Enclomiphene in an organic solvent, wherein said organic solvent consist in only ethanol.

Said process is a very preferred process for the preparation of Enclomiphene citrate having needle shaped crystal habit since provides product with high chemical purity, using only one solvent for both the steps, passing through an intermediate with excellent properties.

Examples of said process are those of example 28 and 29, plus the FIG. 25 which shows the needle crystal habit of the product Enclomiphene citrate obtained by said process.

In the step b) the addition of citric acid can be carried out by addition of solid citric acid or, alternatively and preferably, by addition of a solution of citric acid in ethanol.

In the steps b), the solution of Enclomiphene in ethanol can be realized by solubilization of Enclomiphene in a volume of ethanol comprised between 2 and 30 volumes, preferably between 5 and 20 volumes, more preferably 10 volumes.

According to a preferred embodiment of said process for the preparation of Enclomiphene citrate having needle shaped crystal habit, the Enclomiphene to be crystallized of the step a) is prepared starting from E-Clomiphene BPA salt, i.e. from Enclomiphene salt with racemic binaphthyl-phosphoric acid of formula (VI). Example 28 exemplify such an embodiment.

It can be appreciated as the process for the preparation of Enclomiphene citrate having needle shaped crystal habit can be carried out employing in both the steps a) and step b) the same solvent being ethanol, only.

Moreover, said improved process for the preparation of Enclomiphene citrate having needle shaped crystal allows the preparation of Enclomiphene citrate having high chemical purity, i.e. more than 99.90% by HPLC A/A % with a content of residual cis-Clomiphene impurity lower than 0.10% by HPLC A/A % (see example 29).

Indeed, during the development of the process for the preparation of the improved Enclomiphene citrate having needle shaped crystal habit, it was tried to isolate and crystallize Enclomiphene free base, also named Enclomiphene (base) or Enclomiphene base or Enclomiphene.

In particular, it has been surprisingly found that Enclomiphene (base) crystallized from ethanol, i.e. pure or absolute ethanol, and in absence of other solvents (step a) as in the step a) of the above process, presents large and well defined single prismatic crystals having well advantageous properties, as below described.

The visual aspect and therefore the crystal habit of the crystals of Enclomiphene crystallized form ethanol is transparent macrocrystals having prismatic shape.

Enclomiphene crystallized form ethanol has crystals being prisms with a lenght comprised in the range of 0.08 to 2.0 millimeters. In particular, the longer crystals have a length comprised in the range of 1.0 to 2.0 millimeters.

Moreover, such Enclomiphene having prismatic shaped crystal habit is composed by prism shaped crystals of different sizes.

Figure 11:
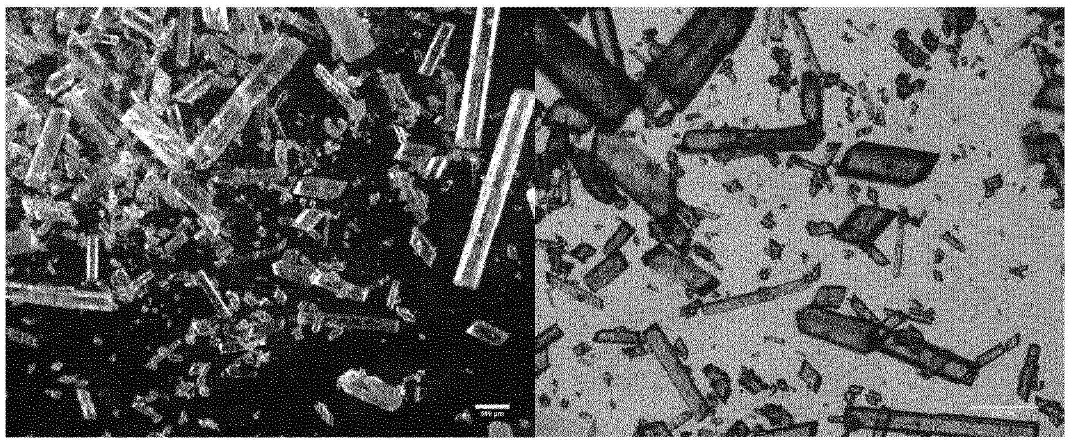
FIG. 11 shows microscopy analysis, i.e. a pictures with scale 500 μm (size of 500 μm in the bottom of the picture), of the crystals of Enclomiphene (base) having prismatic crystal habit, as crystallized from ethanol. Picture on the left side is acquired with reflected light (left) while picture on the right side is acquired with transmitted light.

Indeed, the general crystal form of the specimens seen in the FIG. 11 is called a prism, prism being defined by the four lateral faces that are parallel to the elongation direction. As the smaller faces that close the parallepipedic prisms (base and top), are not perpendicular to the elongation direction, they are oblique prisms (faces do not form right angles between them; the faces are oblique parallelograms: they are rhomboids, not rhombuses, not rectangles, not squares).

On the other hand, as the faces have different relative growth, some prisms are longer than others, having columnar habit (if the relation length/width would increase they will have acicular habit (needles) and, at the end, fibrous habit). On the contrary, the shorter prism can be called short prisms (and, going to the other end of the relation, having tabular (platy) and lamellar habit).

Figure 19:
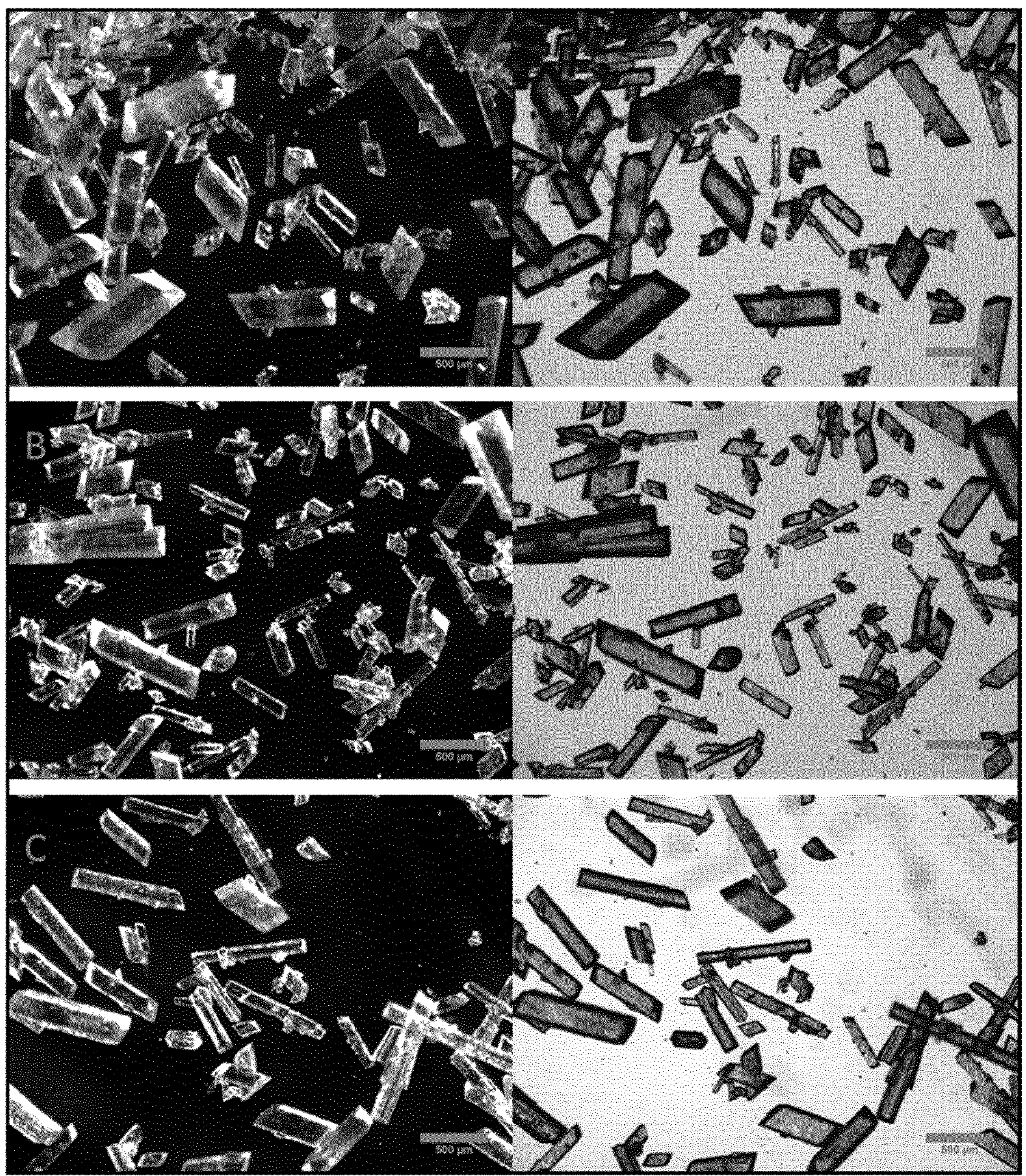
FIG. 19 shows the microscopy analysis of Enclomiphene (base) having prismatic shaped crystal habit after 30 days respectively at 60% RH (A), 75% RH-40° C. (B), and 95% RH (C), with reflected light (left) and transmitted light (right) (scale 500 μm).

In the present case, the shortest prisms seen in FIG. 11 or FIG. 11-BIS or FIG. 19, as they are oblique prisms, remind the regular form called rhombohedron, but they can not be properly called with this name as the six faces are not rhombuses (i.e., the angles formed by each pair of faces are not exactly the same).

Therefore, strictly speaking, the rhombohedrical adjective must be reserved to prisms whose faces are rhombuses (six equal rhombuses) as a result of the symmetry elements determined by the internal structure of the crystal. Of course, this is not the case in the crystals depicted in FIG. 11 or 11-BIS or FIG. 19 (picture 19 was taken after 30 days of stabilty testing).

The name of the crystals in the FIG. 11, 11-BIS or 19 must thus be "prisms", "short prisms", "long prisms" or "oblique prisms", "short oblique prisms", "long oblique prisms" and so on, depending on his length. It could be said that when prisms are short some of them resemble a rhombohedron or that are rhombohedral-like shaped. Nevertheless, although the shortest prisms shown in the image remind the regular form called rhombohedron, said term cannot be used to describe the crystals of the invention since said term implies a crystal symmetry that is obviously not the one of this crystalline structure.

Thus, Enclomiphene crystallized form ethanol can be named as Enclomiphene having prismatic shaped crystal habit or Enclomiphene having prismatic crystals or Enclomiphene having prism crystals.

This solid form of Enclomiphene of formula (I):

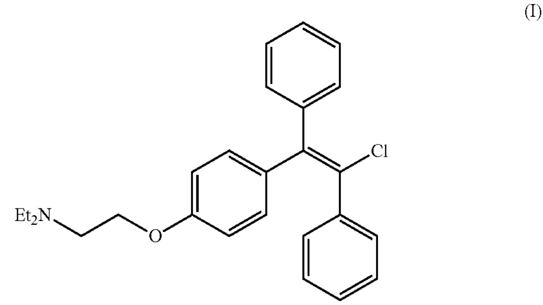

has prismatic shaped crystal habit and/or has median value (D50) of the particle size distribution comprised in the range from 100 μm to 500 μm.

In Enclomiphene having prismatic shaped crystal habit, the prismatic shaped crystal habit corresponds to crystals having the shape of prisms and/or short prisms and/or long prisms and/or oblique prisms and/or short oblique prisms and/or long oblique prisms.

Vice-versa, Enclomiphene obtained for example by crystallization from ethanol denatured toluene presents polycrystalline aggregates formed by small needles. The different morphology of Enclomiphene crystals prepared by crystallization in pure or absolute ethanol and for example that obtained by crystallization in ethanol denatured toluene is well evident also by visual observation.

Figure 12:
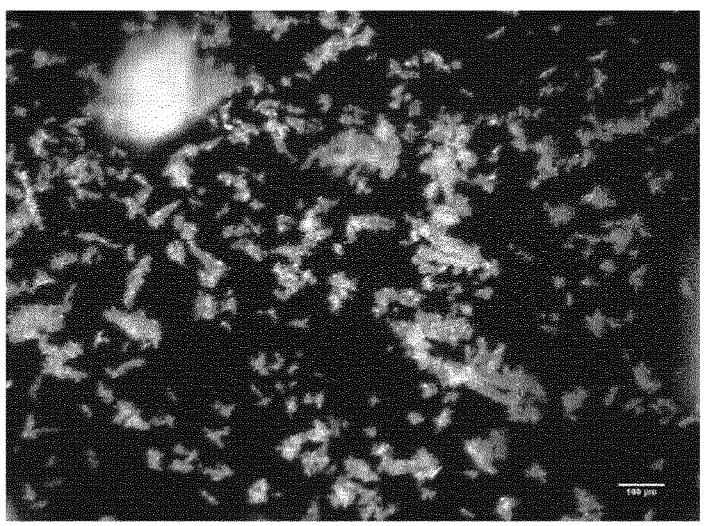
FIG. 12 shows microscopy analysis, i.e. a picture with scale 100 μm (size of 100 μm in the bottom and right side of the picture), of the crystals of Enclomiphene (base) having non-prismatic crystal habit.

Microscopy analysis showed different crystal shapes for each batch, in particular:

Enclomiphene crystallized form ethanol denatured toluene (see example 19) shows polycrystalline aggregates of small needles (see FIG. 12).

Enclomiphene crystallized form pure ethanol (see example 18) shows large transparent monocrystalline prisms (see FIG. 11).

In Enclomiphene having prismatic shaped crystal habit, the crystals are prisms having a length comprised in the range from 0.08 to 2.0 millimeters.

In particular, Enclomiphene having prismatic shaped crystal habit has a distribution of particles with a relatively big size: from 80 μm (D10) to 770 μm (D90), more particularly, 50% of the particles (expressed as Volume %) have a diameter comprised between 200 μm and 600 μm. See FIG. 20.

Moreover, Enclomiphene having prismatic shaped crystal habit has a median value (D50) of the particle size distribution comprised in the range from 100 μm to 500 μm, in particular, is comprised in the range from 200 μm to 400 μm, more particularly is comprised in the range of 250 μm to 350 μm.

Moreover, Enclomiphene having prismatic shaped crystal habit has a mean value of the particle size distribution comprised in the range from 100 μm to 500 μm, in particular, is comprised in the range from 250 μm to 450 μm, more particularly is comprised in the range from 350 μm to 400 μm.

Furthermore, Enclomiphene having prismatic shaped crystal habit has a median value (D50) of the particle size distribution comprised in the range from 100 μm to 500 μm, in particular, is comprised in the range from 200 μm to 400 μm, more particularly is comprised in the range from 250 μm to 350 μm and has a mean value of the particle size distribution comprised in the range from 100 μm to 500 μm, in particular, is comprised in the range from 250 μm to 450 μm, more particularly is comprised in the range from 350 μm to 400 μm.

According to an embodiment, Enclomiphene having prismatic shaped crystal habit has median value (D50) of the particle size distribution comprised in the range from 100 μm to 500 μm and the mean value of the particle size distribution comprised in the range from 100 μm to 500 μm.

According to a preferred embodiment, Enclomiphene having prismatic shaped crystal habit has median value (D50) of the particle size distribution comprised in the range from 200 μm to 400 μm and the mean value of the particle size distribution comprised in the range from 250 μm to 450 μm.

According to a more preferred embodiment, Enclomiphene having prismatic shaped crystal habit has median value (D50) of the particle size distribution comprised in the range from 250 μm to 350 μm and the mean value of the particle size distribution comprised in the range from 350 μm to 400 μm.

Figure 21:
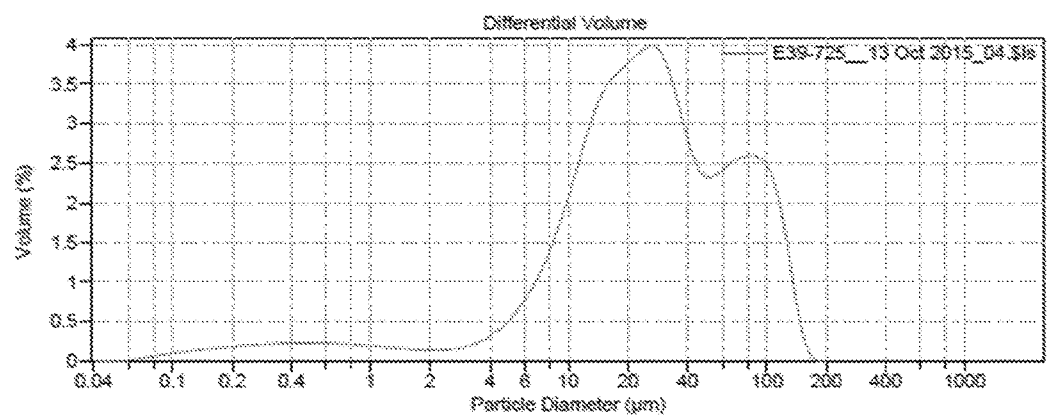
FIG. 21 shows PSD analysis of Enclomiphene base having non-prismatic crystal habit, not sonicated.

Enclomiphene not having prismatic shaped crystal habit has instead median value (D50) and the mean value both comprised between 10 and 50 μm (See FIG. 21).

Thus, Enclomiphene having prismatic shaped crystal habit and/or has median value (D50) of the particle size distribution comprised in the range from 100 μm to 500 μm can also be named as Macro Enclomiphene or Enclomiphene having macrocrystal habit.

Thus, it is another object of the present invention, Enclomiphene having has median value (D50) of the particle size distribution comprised in the range from 100 μm to 500 μm or having the other values of particle size distribution above said for Enclomiphene having prismatic shaped crystal habit.

The process of crystallization of Enclomiphene base from ethanol, without other solvents, thus provides Enclomiphene having has median value (D50) of the particle size distribution comprised in the range from 100 μm to 500 μm, also named Macro Enclomiphene or Enclomiphene having macrocrystal habit.

Enclomiphene having prismatic shaped crystal habit is not hygroscopic as determinated by DSV (dynamic Vapour Sorption) with a Q5000 TA instrument, at 25° C. over the whole range 0-95% RH.

Enclomiphene having prismatic shaped crystal habit is prepared by a process of crystallization of the Enclomiphene from ethanol, without other solvents.

Thus, it is object of the present invention also a process for the preparation of Enclomiphene having prismatic shaped crystal habit, by crystallization of the Enclomiphene from ethanol.

Ethanol can be pure ethanol or absolute ethanol.

The term crystallization used in the various embodiments of the present invention, means the simple crystallization or precipitation or, alternatively, also include the re-crystallization.

In particular, Enclomiphene having prismatic shaped crystal habit is prepared by a process of crystallization of the Enclomiphene in a volume from 2 to 10 volumes of ethanol for weight unit of Enclomiphene base, wherein from 3 to 6 volumes of ethanol provided the better results, about 5 volumes being the best volume of ethanol.

In particular, Enclomiphene having prismatic shaped crystal habit is prepared by a process of crystallization of the Enclomiphene from ethanol at a temperature comprised between 0° C. and 25° C.

Examples 18 and 28 provide a procedure to carry out the preparation of Enclomiphene having prismatic shaped crystal habit.

As said above, Enclomiphene having prismatic shaped crystal habit shows many advantages, especially for using it as process intermediate for the preparation of Enclomiphene citrate and Enclomiphene citrate having needle shaped crystal habit.

Enclomiphene having prismatic shaped crystal habit is indeed very well filterable, since, for example, the filtration (on paper over a Buckner) of 40 mL of suspensions containing of said solid in ethanol takes only 10 seconds.

Since Enclomiphene having prismatic shaped crystal habit has higher filterability (also compared with the filterability of Enclomiphene obtained by crystallization from denatured ethanol), such Enclomiphene shows higher chemical purity, especially in terms of residual cis-Clomiphene impurity.

Enclomiphene having prismatic shaped crystal habit is a better solid form of Enclomiphene base, suspension of the which filter more quickly, thus consequently, allowing the improvement of the chemical purity of Enclomiphene (base) and then Enclomiphene citrate and Enclomiphene citrate having needle shaped crystal habit.

Examples 28 and 29 provide indeed evidence of the effect provided by the preparation and isolation of Enclomiphene having prismatic shaped crystal habit and its conversion to Enclomiphene citrate having needle shaped crystal habit, which shows a chemical purity of 99.92% (HPLC A/A %) with a residual Cis-Clomiphene impurity of only 0.03% (HPLC A/A %), wherein the removal of the Cis-Clomiphene impurity has actually occurred during the isolation of Enclomiphene having prismatic shaped crystal habit.

The preparation and isolation of Enclomiphene base having prismatic shaped crystal habit in the processes for the preparation of Enclomiphene citrate or Enclomiphene citrate having needle shaped crystal habit indeed provides also the effect of providing product with high chemical purity, especially with reference to the content of cis-Clomiphene impurity, since the isolation of said intermediate Enclomiphene solid form allows the removal of the most part of the amount of said impurity.

Moreover, Enclomiphene having prismatic shaped crystal habit is an improved solid form of Enclomiphene base since it shows higher flowability, thus suitable for the industrial manufacturing form Enclomiphene citrate, using said Enclomiphene base as a chemical synthetic intermediate and/or for the industrial manufacturing pharmaceutical products comprising said Enclomiphene.

Microscopy analysis of Enclomiphene base having prismatic shaped crystal habit exposed to three stability conditions for 30 days showed the same colorless transparent prism as the starting product. See FIG. 19. Therefore the Enclomiphene having prismatic shaped crystal habit remains stable at least one month under the three stability conditions.

Therefore, considering the above discussed properties, Enclomiphene having prismatic shaped crystal habit is well suitable as an excellent synthetic intermediate for the preparation of Enclomiphene citrate (see process described hereafter) and Enclomiphene citrate having needle shaped crystal habit (see process described above), especially on large scale manufacturing.

Thus, another object of the present invention is a process for the preparation of Enclomiphene citrate comprising the following steps:

a) preparation of Enclomiphene having prismatic shaped crystal habit and/or having median value (D50) of the particle size distribution comprised in the range from 100 μm to 500 μm, by crystallization of the Enclomiphene from ethanol, b) conversion of Enclomiphene of the step a) to Enclomiphene citrate by addition of citric acid or citric acid monohydrate to a solution of Enclomiphene in an organic solvent.

The step b) can be carried out by addition of citric acid or citric acid monohydrate to a solution of Enclomiphene having prismatic shaped crystal habit solubilized in ethanol, methanol or acetone.

The step b) can be carried out by addition of solid citric acid or solid citric acid monohydrate to a solution of Enclomiphene having prismatic shaped crystal habit solubilized in ethanol, methanol or acetone.

Alternatively and preferably, the step b) can be carried out by addition of a solution of citric acid or solid citric acid monohydrate in methanol, ethanol or acetone to a solution or suspension of Enclomiphene having prismatic shaped crystal habit solubilized respectively in ethanol, methanol or acetone.

More preferably, the step b) can be carried out by addition of a solution of citric acid or solid citric acid monohydrate in ethanol to a solution of Enclomiphene having prismatic shaped crystal habit solubilized in ethanol. The step b) can be carried out at a temperature comprised between 0° C. and 78° C., preferably at a temperature comprised between 0° C. and 25° C.

It can be thus appreciated as the Enclomiphene having prismatic shaped crystal habit, a solid whose suspension is very well filterable and a solid having excellent flowability, bulk density, tapped density, compressibility index (see example 23) and chemical purity (see e.g. the low content of cis-Chlomiphene in example 28), is an excellent process intermediate, that can be very advantageously used for the preparation of Enclomiphene citrate or, preferably, for the preparation of Enclomiphene citrate having needle shaped crystal habit, according to the two processes above described.

It can thus appreciated as Enclomiphene of formula (I) having prismatic shaped crystal habit can be therefore advantageously used for the preparation of Enclomiphene citrate.

Figure 16:
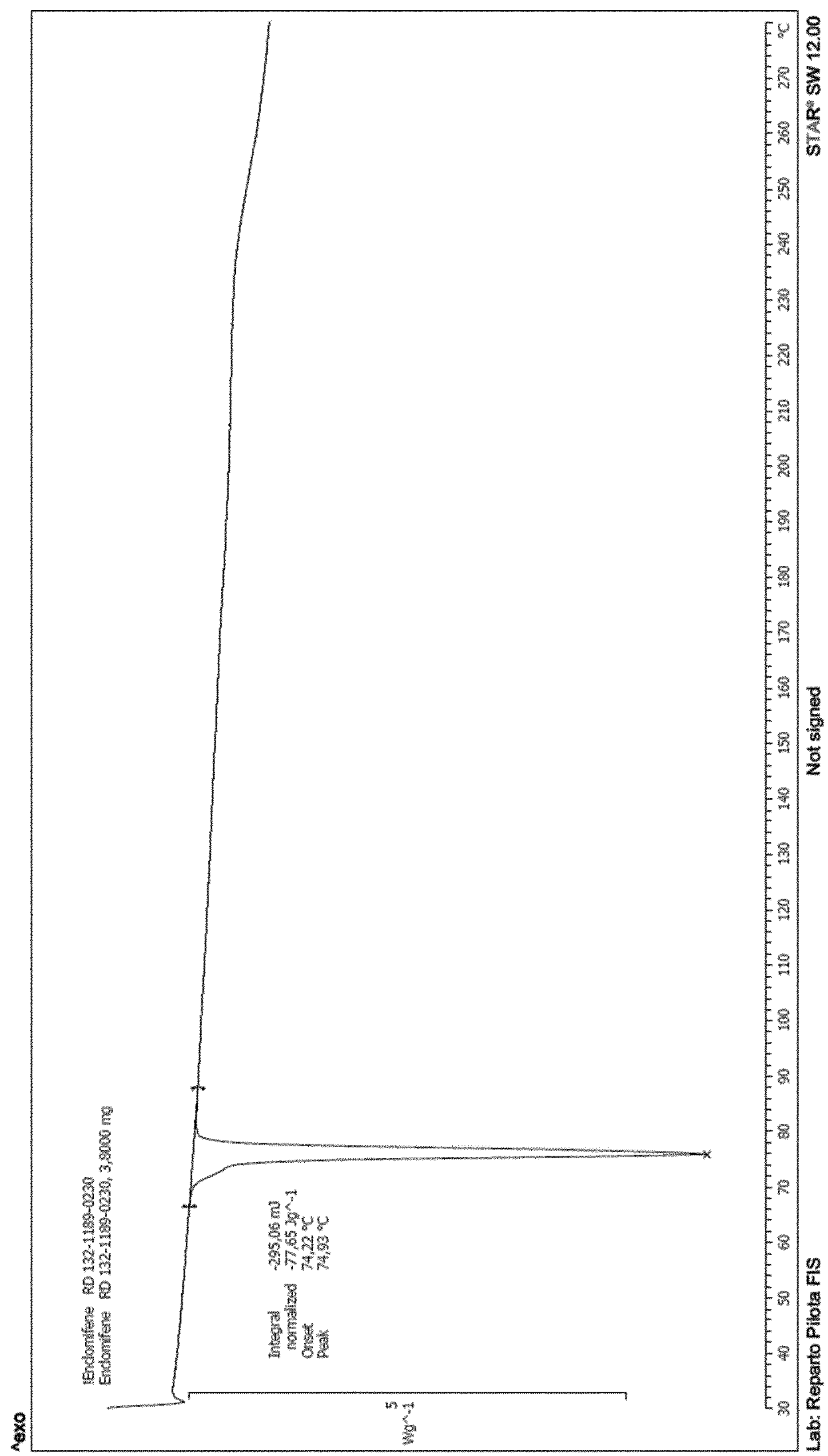
FIG. 16 shows the DSC curve of Enclomiphene (base) having non-prismatic crystal habit.
Figure 17:
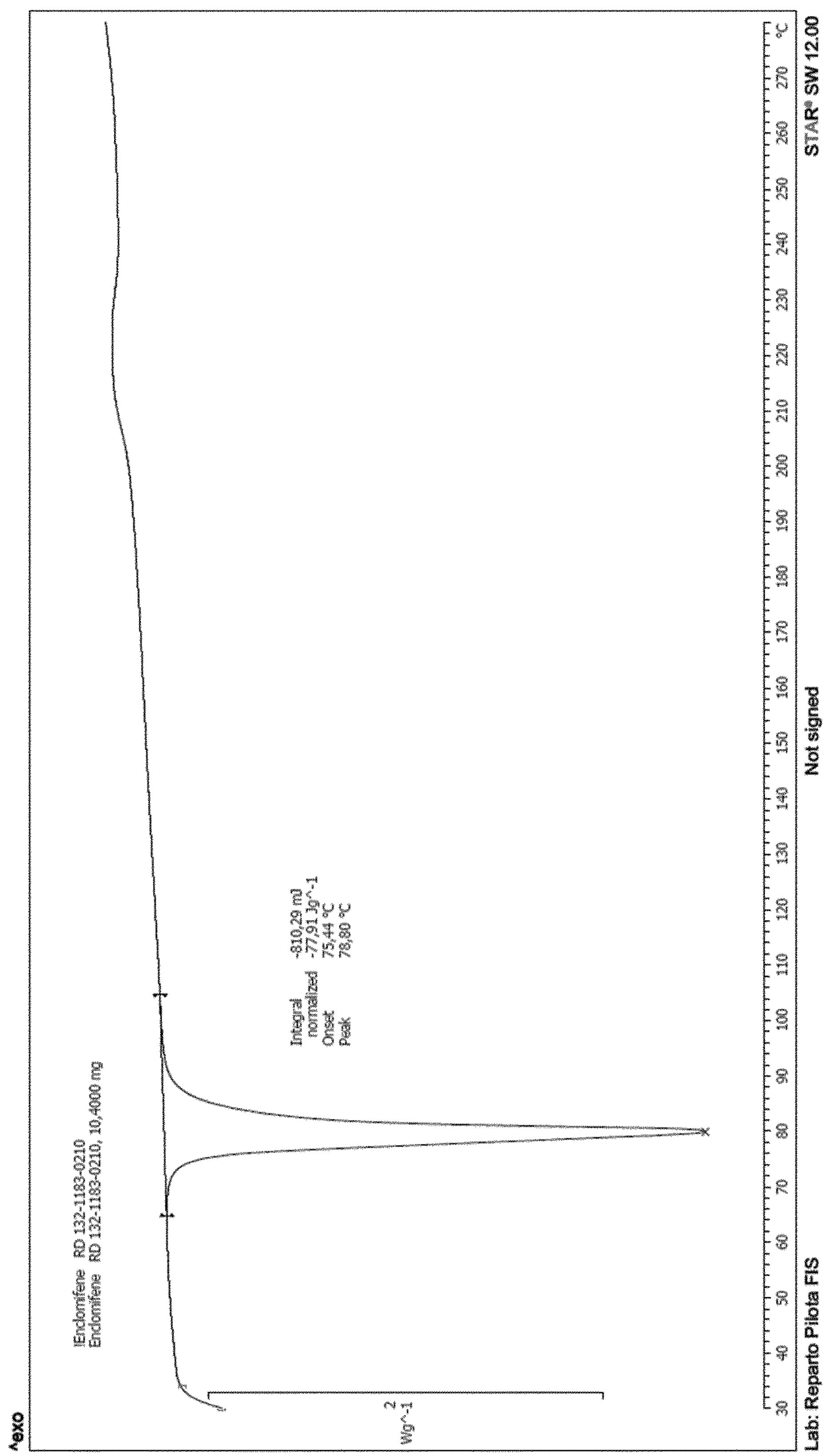
FIG. 17 shows the DSC curve of Enclomiphene (base), having prismatic crystal habit.

Enclomiphene having prismatic shaped crystal habit has a melting point of 79° C. as measured by DSC (peak) (see FIG. 17), while Enclomiphene crystallized from ethanol denatured toluene has a melting point of 75° C. measured by DSC (peak) (See FIG. 16). The latter melting point being the same as that described in literature for Enclomiphene base.

It is thus evident that Enclomiphene having prismatic shaped crystal habit is a thermodynamically more stable solid form in comparison with Enclomiphene solid forms having lower melting point such as, for example, that obtained by crystallization with ethanol denatured with toluene.

Having higher thermal stability, Enclomiphene having prismatic shaped crystal habit provides better storage stability (useful for the storage of said intermediate in the warehouse) and easier manufacturing of the pharmaceutical composition comprising Enclomiphene.

Figure 15:
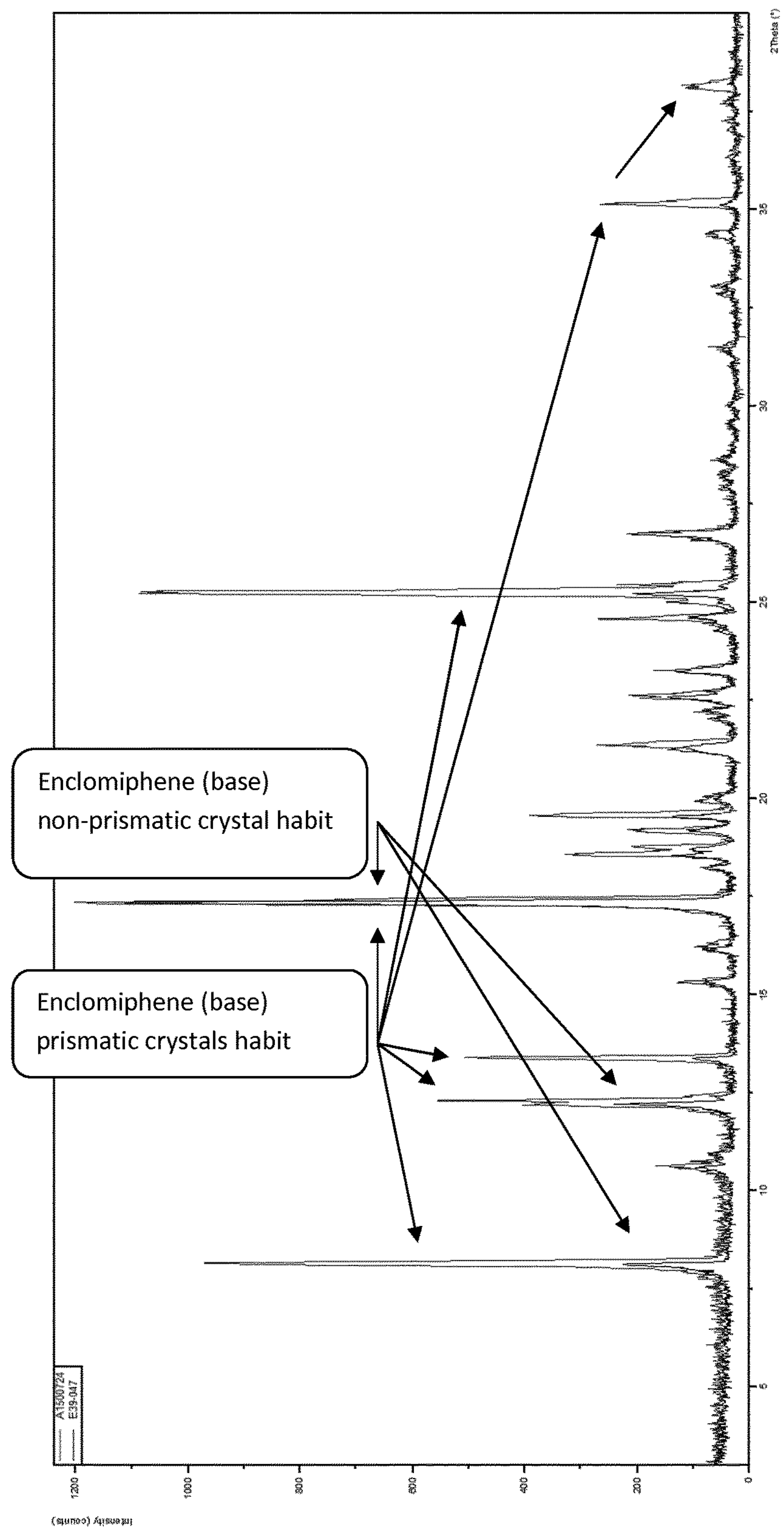
FIG. 15 shows a comparison of XRPD diffractograms of samples of Enclomifene (base) having prismatic crystal habit and Enclomiphene (base) having non-prismatic crystal habit.

The comparison of XPRD diffractograms of samples of Enclomiphene having prismatic shaped crystal habit and Enclomiphene having non-prismatic shaped crystal habit (see FIG. 15) shows very different relative peak intensity for some of the peaks, such as those at 2-Theta values (2θ): 8.1°, 12.3°, 13.4°, 21.3°, 25.2°. The intensity of these peaks is much lower in the case of Enclomiphene having non-prismatic shaped crystal habit, while other peaks have similar intensity (such as 15.3°, 17.3°, 18.2° and 23.2° 28). The different crystal habit or different crystal form observed for both batches, i.e. large prisms for Enclomiphene having prismatic shaped crystal habit (crystallized from ethanol) and very little needles for Enclomiphene having non-prismatic shaped crystal habit crystallized explains these differences in the XPRD diffractograms.

Moreover, considering the XPRD intensities described in table of example 21, Enclomiphene having prismatic shaped crystal habit has a characteristic X-ray powder diffraction pattern with characteristic peak expressed in 2-Theta values (2θ) at 25.3 (vs) wherein (vs)=very strong intensity.

Thus, again considering the XPRD intensities, Enclomiphene having prismatic shaped crystal habit has a characteristic X-ray powder diffraction pattern with characteristic peaks expressed in 2-Theta values (2θ) at: 8.1 (s), 17.3 (vs), 25.2 (vs), 25.3 (vs); wherein (vs)=very strong intensity, (s)=strong intensity.

Enclomiphene having prismatic shaped crystal habit has a characteristic X-ray powder diffraction pattern with characteristic peaks expressed in 2-Theta values (2θ) at: 8.1 (s), 12.3 (m), 13.4 (m), 17.3 (vs), 17.5 (m), 19.5 (m), 25.2 (vs), 25.3 (vs); wherein (vs)=very strong intensity; (s)=strong intensity; (m)=medium intensity.

Enclomiphene having prismatic shaped crystal habit has a characteristic X-ray powder diffraction pattern with characteristic peaks expressed in 2-Theta values (2θ) at: 8.1 (s), 12.2 (w), 12.3 (m), 13.4 (m), 17.3 (vs), 17.5 (m), 18.5 (w), 18.7 (w), 19.2 (w), 19.5 (m), 21.3 (w), 24.6 (w), 25.2 (vs), 25.3 (vs); 25.4 (w), 26.7 (w), wherein (vs)=very strong intensity; (s)=strong intensity; (m)=medium intensity, (w)=weak intensity.

Moreover, considering the comparison of the XPRD intensities described in table of example 21, Enclomiphene having prismatic shaped crystal habit has a characteristic X-ray powder diffraction pattern with characteristic peaks expressed in 2-Theta values (2θ) at: 12.3, 17.5, 25.3; in particular, also considering intensities, with peaks expressed in 2-Theta values (2θ) at: 12.3 (m), 17.5 (m), 25.3 (vs); wherein (vs)=very strong intensity; (s)=strong intensity; (m)=medium intensity, (w)=weak intensity.

Moreover, again considering the comparison of the XPRD intensities described in table of example 21, Enclomiphene having prismatic shaped crystal habit has a characteristic X-ray powder diffraction pattern with characteristic peaks expressed in 2-Theta values (2θ) at: 12.3, 17.5, 21.3, 25.3, 25.4; in particular, also considering intensities, with peaks expressed in 2-Theta values (2θ) at: 12.3 (m), 17.5 (m), 21.3 (w), 25.3 (vs), 25.4 (w); wherein (vs)=very strong intensity; (s)=strong intensity; (m)=medium intensity, (w)=weak intensity. All said peaks appears typical peaks of the solid form or crystalline form being Enclomiphene having prismatic shaped crystal habit since they are not present in the XPRD diffractogram of Enclomiphene with polycrystalline aggregates of short needles, having non-prismatic shaped crystal habit.

The meanings given above for (vs)=very strong intensity, (s)=strong intensity, (m)=medium intensity refer to the following relative intensities percentages:

(vs)=very strong intensity means Rel. Int [%] in the range 81-100, (s)=strong intensity means Rel. Int [%] in the range 60-80, (m)=medium intensity means Rel. Int [%] in the range 30-59.

(w)=weak intensity means Rel. Int [%] in the range 15-29.

Enclomiphene having prismatic shaped crystal habit, i.e. Enclomiphene composed by large single crystals of prism shape, provides much better flowability, bulk density and tapped density in comparison with Enclomiphene being polycrystalline aggregates of short needles as prepared by crystallization from ethanol denatured toluene, whose preparation is exemplified in example 19 (see examples 22 and 23).

The solid form being Enclomiphene having prismatic shaped crystal habit thus allows to save space in the warehouse and in the containers for transportation. Moreover, this form provides evident advantages in the processing for preparing pharmaceutical composition of Enclomiphene because of his improved flowability.

In other words, since Enclomiphene base having prismatic shaped crystal habit shows better flowability properties, said form allows an easier manufacturing of pharmaceutical compositions of Enclomiphene since it shows better processing properties.

It has been found a new solid form of Enclomifene, which is an Enclomiphene salt with higher solubility in aqueous medium.

In particular, it has been found that Enclomiphene acetate of formula (IV):

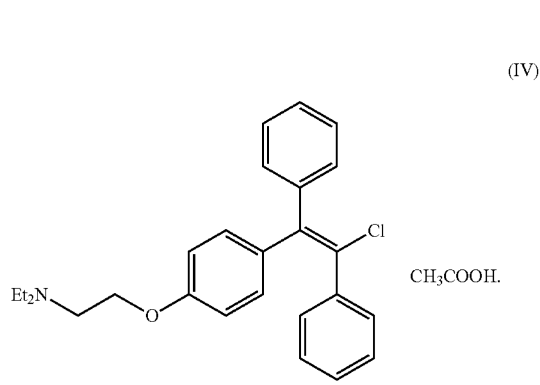

is much more soluble than Enclomiphene citrate in aqueous medium.

More in particular, Enclomiphene acetate is much more soluble at pH 4.5 than Enclomiphene citrate.

In particular, at pH 4.5, Enclomiphene acetate is about 15 times more soluble than Enclomiphene citrate having non-needle crystals (having a m.p. of 147° C. as measured by DSC (onset)).

In particular, at pH 4.5, Enclomiphene acetate is about 2.5 times more soluble than Enclomiphene citrate needle crystals (having a m.p. of 150° C. as measured by DSC (onset)).

Enclomiphene acetate can be conveniently formulated for giving pharmaceutical compositions comprising Enclomiphene acetate and one or more pharmaceutical acceptable excipients.

Examples of suitable pharmaceutical compositions comprising Enclomiphene acetate are those disclosed in WO2006102232A2, WO2010054248A1, WO2013020017A1, WO2013123218A1, WO2013130832A1, example 3 of WO2014031177A1 or WO2014070523A1 with the difference that Enclomiphene acetate is used instead of the disclosed Enclomiphene citrate.

Thus, Enclomiphene acetate and pharmaceutical compositions thereof can be used as medicament, in particular, for can be used in the treatment ovulatory dysfunction or polycystic ovary syndrome.

Moreover, Enclomiphene acetate is suitable for the preparation of very fast release pharmaceutical compositions comprising Enclomiphene acetate and one or more acceptable pharmaceutical excipients.

EXPERIMENTAL SECTION

The starting material 1-{4-[2-(Diethylamino)ethoxy]phenyl}-1,2-diphenylethanol can be prepared according to well known prior art methods or can be purchased on the market.

Example 1: Preparation of Clomiphene Citrate from 1-{4-[2-(Diethylamino)Ethoxy]Phenyl}-1,2-Diphenylethanol

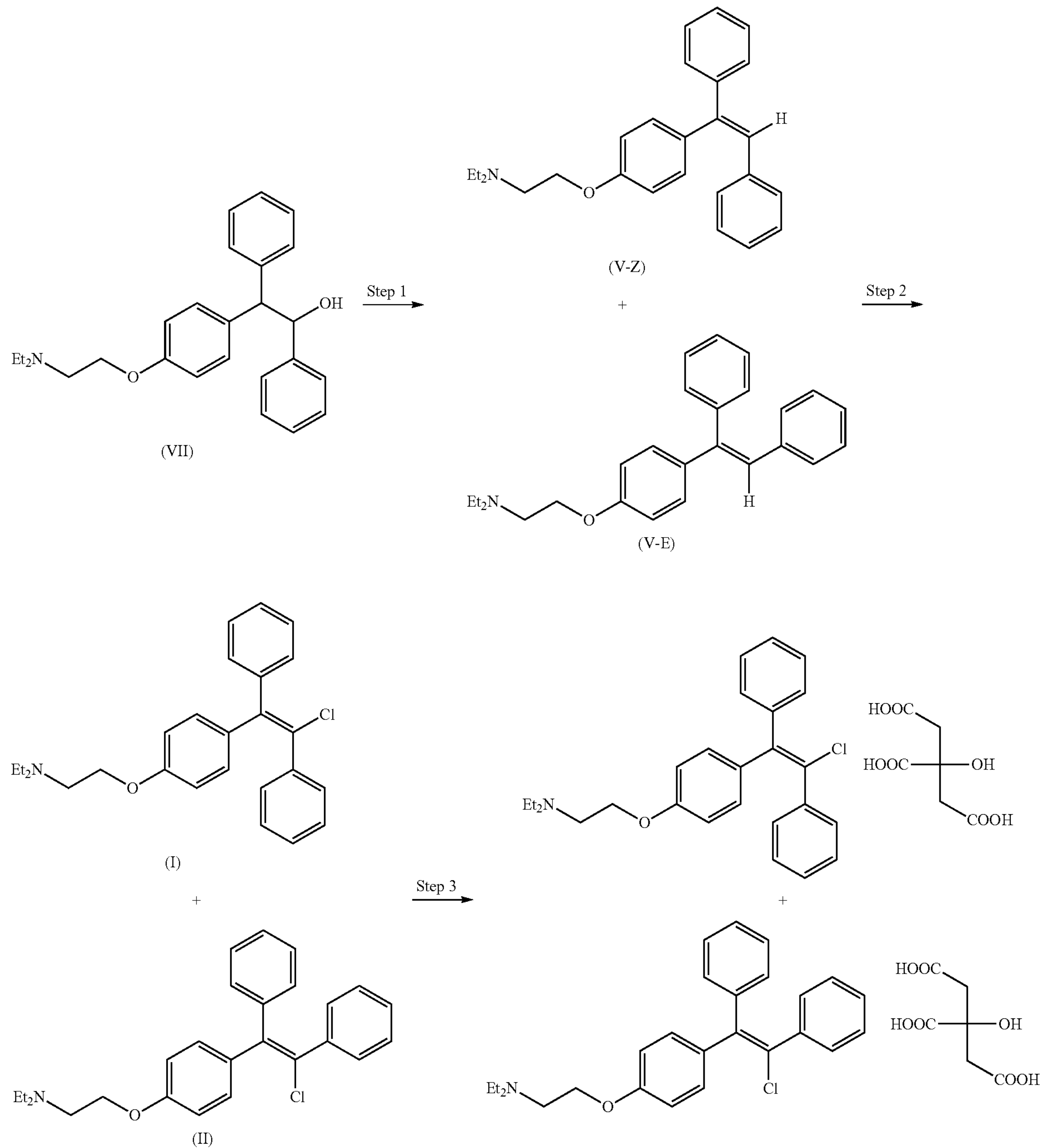

Step 1

A round bottomed flask fitted with distillation equipment was loaded with 250 g of 1-{4-[2-(Diethylamino)ethoxy] phenyl}-1,2-diphenylethanol and 1250 mL of toluene. To this mixture, 85 mL of HCl 32% w/w were added, the temperature was raised to the boiling point and all the water was azeotropically removed by means of a Dean-Stark apparatus, obtaining 2-{4-[(E/Z)-1,2-diphenylethenyl]phenoxy}-N,N-diethylethanamine hydrochloride, as mixture of geometric isomers of formula (V-Z) and (V-E).

Step 2

The reaction mixture was brought to 60° C. and, maintaining this temperature, 500 mL of acetic acid were added during 30'. The water content was checked below 500 ppm (Karl Fischer titration).

A warm solution (50-60° C.), prepared with 60 g of dichloro dimethyl hydantoin (1,3-dichloro-5,5-dimethyl hydantoin; abbreviated DCDMI) (0.474 mol. equiv.) in 600 mL of toluene, was slowly added to the reaction mixture during 90' maintaining the temperature at about 60° C. After checking the conversion by HPLC, a small addition of DCDMI solution was necessary in order to have the starting material below 0.5%. The reaction mixture was cooled to 15-20° C. and treated slowly with 750 mL of water and, up to pH 12, approximately 1000 mL of aqueous sodium hydroxide 30% w/w solution. After stirring for 30', the layers were separated and the organic phase was washed with 3×250 mL of water and concentrated by vacuum distillation thus obtaining 280 g of Clomiphene, as an oil containing some residual toluene of formula (I) and (II).

Step 3

The oil obtained in the previous step was taken up with 625 mL of acetone, the clear solution warmed to gentle boiling and a solution composed of 142.5 g of citric acid monohydrate and 1000 mL of acetone was slowly added during 30'. The reaction mixture was stirred while slowly cooling to 0° C. and then 4 hours at 0° C. The product was filtered, washed with acetone and dried under vacuum obtaining 361 g of Clomiphene citrate, the molar yield was 94.1%. HPLC purity >98% (A/A %).

Example 2a: Preparation of Salt of Trans-Clomiphene with Racemic Binaphthyl-Phosphoric Acid, Starting from Clomiphene Citrate A round bottom flask was charged 100 gr of Clomiphene Citrate (HPLC analysis (A/A %): 65.21% E-Clomiphene, 34.06% Z-Clomiphene) and 1000 mL of Methanol. The suspension was stirred at 30° C. up the complete dissolution. Then a solution of racemic binaphthyl-phosphoric acid (abbreviated BPA) 30 gr (0.515 eq) in 30 mL of DMF was added. At the end of addition the mixture was stirred for 1 h at 30° C. The obtained suspension was filtered and the solid was washed with 100 mL of Methanol.

50.4 gr of E-Clomiphene BPA salt were obtained.

HPLC Analysis (A/A %): 97.04% E-Chlomiphene, 2.5% Z-Clomiphene.

Example 2b: Preparation of Salt of Trans-Clomiphene with Racemic Binaphthyl-Phosphoric Acid, Starting from Clomiphene Citrate A round bottom flask was charged 50 gr of Clomiphene Citrate (the same as that used in example 2a) and 500 mL of

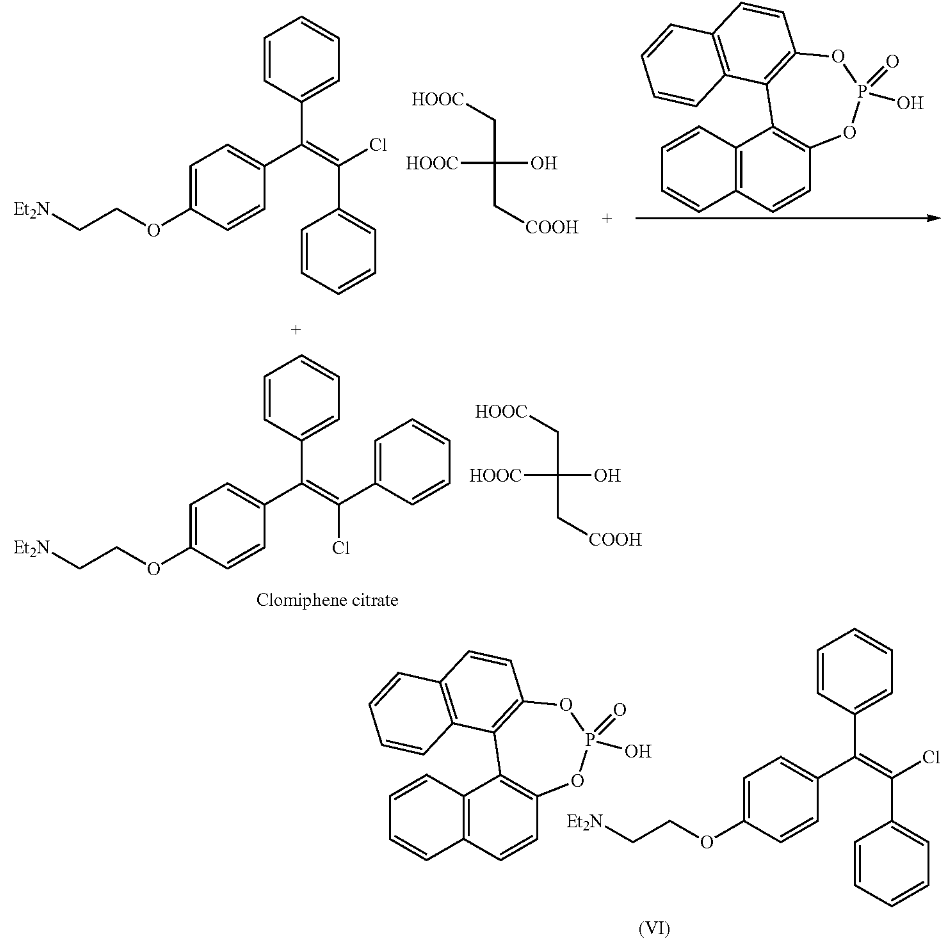

Methanol. The suspension was heated at 40-45° C. and stirred up to the complete dissolution. Then a solution of BPA 15 gr (0.515 eq) in 300 mL of methanol was added. At the end of addition the mixture was stirred for 1 h at 20° C. The obtained suspension was filtered and the solid was washed with 100 mL of Methanol.

24.1 gr of E-Clomiphene BPA salt were obtained.

HPLC Analysis (A/A %): 98.96% E-Chlomiphene, 0.69% Z-Clomiphene.

Example 2c: Preparation of Salt of Trans-Clomiphene with Racemic Binaphthyl-Phosphoric Acid, Starting from Clomiphene Citrate In a round bottom flask was charged 100 gr of Clomiphene Citrate (the same as that used in example 2a) and 1000 mL of Methanol. The suspension was heated at 40-45° C. and stirred up the complete dissolution. Then a solution of BPA 30 gr (0.515 eq) in 1000 mL of methanol was added. At the end of addition the mixture was stirred for 1 h at 20° C. the obtained suspension was filtered and the solid was wash with 100 mL of Methanol.

47.9 gr of E-Clomiphene BPA salt were obtained.

HPLC Analysis (A/A %): 98.81% E-Clomiphene, 0.79% Z-Clomiphene.

Example 2d: Preparation of Salt of Trans-Clomiphene with Racemic Binaphthyl-Phosphoric, Starting from Clomiphene Citrate In a round bottom flask was charged 150 gr of Clomiphene Citrate (the same as that used in example 2a) and 1500 mL of Methanol. The suspension was heater at 40-45° C. and stirred up the complete dissolution. Then a solution of BPA 45 gr (0.515 eq) in 900 mL of methanol was added. At the end of addition the mixture was stirred for 1 h at 20° C. the obtained suspension was filtered and the solid was wash with 100 mL of Methanol.

76.4 gr of E-Clomiphene BPA salt were obtained.

HPLC Analysis (A/A %): 98.82% E-Chlomiphene, 0.80% Z-Clomiphene.

Example 3a: Preparation of Salt of Trans-Clomiphene with Racemic Binaphthyl-Phosphoric Acid, Starting from 1-{4-[2-(Diethylamino)Ethoxy]Phenyl}-1,2-Diphenylethanol

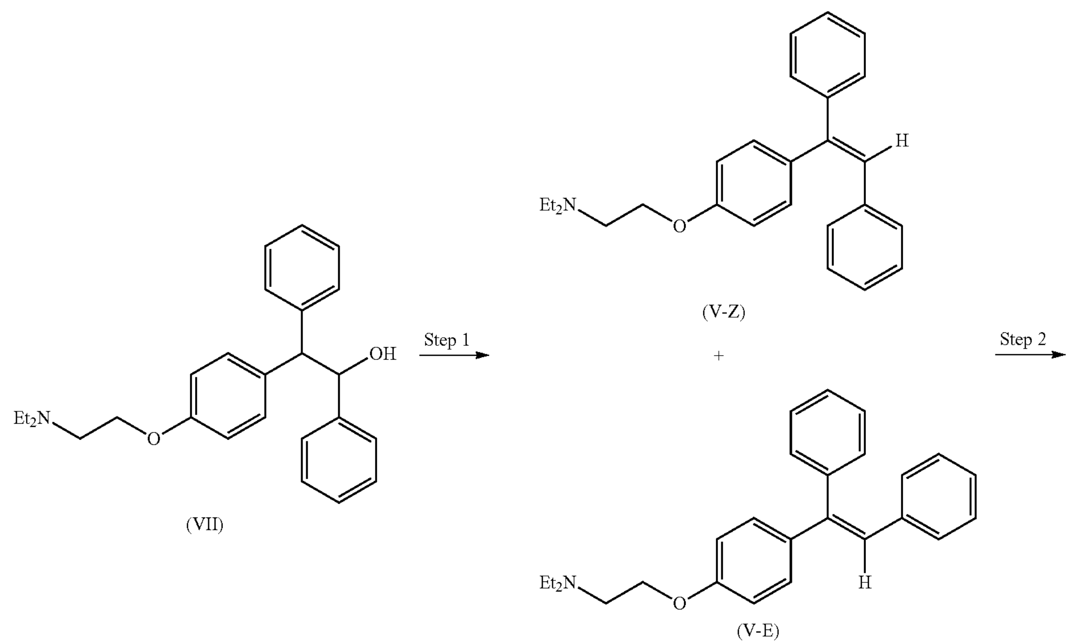

-continued

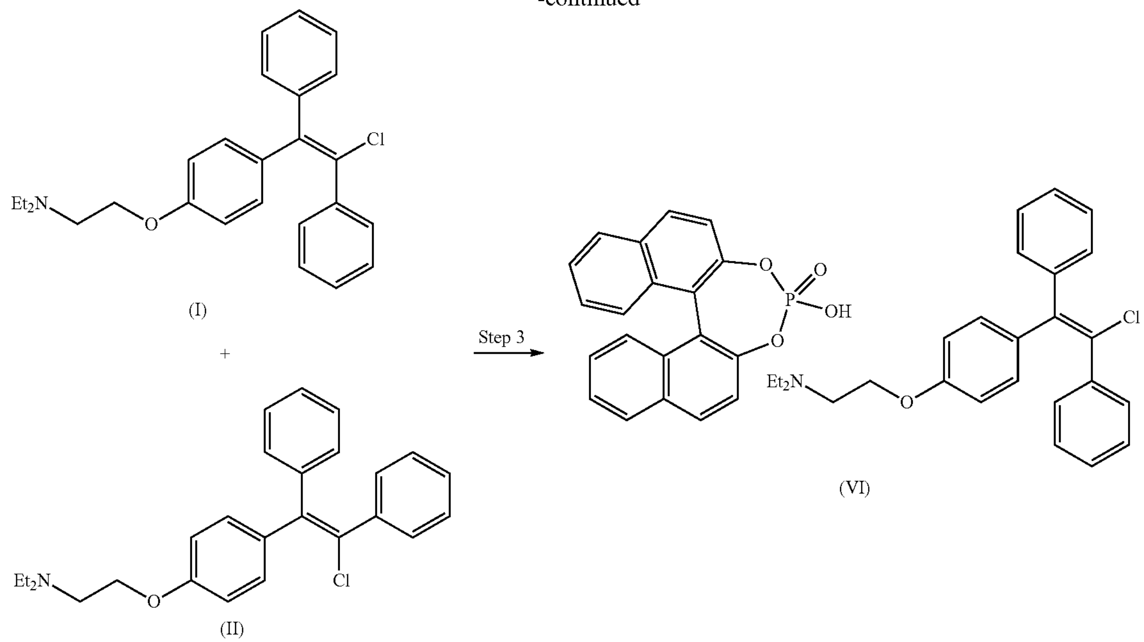

In a round bottom flask was charged 100 gr of 1-{4-[2-(Diethylamino)ethoxy]phenyl}-1,2-diphenylethanol of formula (VII), 300 mL of Toluene and 62 mL of HCl sol. 32%. The mixture was stirred at T=35-40° C. for 30 min. Then the solution was concentrated to residual and the residue was diluted with 300 mL of Toluene. The organic solution was concentrated to residual and the residue was diluted with 800 mL of Dichloromethane (abbreviated DCM). Acetic acid (200 mL) was added to the solution and a solution of DCDMI 26 gr in 250 mL of DCM was added in a period of 90 min. At the end of addition the mixture was stirred for 2 h at r.t. The obtained solution was added in a second round bottom flask containing a solution of 400 mL NaOH 30% and 300 mL of water. The mixture was stirred for 1 h then the phases was separated an the organic phase was washed five times with water (5×100 mL). The obtained organic phase was concentrated to residual and the residue was diluted with 500 mL of Methanol. A solution of racemic binaphthyl-phosphoric acid 45 gr in 1000 mL was added at T=30° C. The obtained solution was stirred at r.t. for 1 h. The suspension was filtered and the solid was wash with 100 mL of Methanol.

79.7 gr of E-Clomiphene salt with racemic binaphthyl-phosphoric acid were obtained.

HPLC Analysis (A/A %): 97.70% E-Clomiphene, 1.67% Z-Clomiphene.

Example 3b: Preparation of Salt of Trans-Clomiphene with Racemic Binaphthyl-Phosphoric Acid In a round bottom flask was charged 100 gr of 1-{4-[2-(Diethylamino)ethoxy]phenyl}-1,2-diphenylethanol of formula (VII), 300 mL of Toluene and 62 mL of HCl sol. 32%. The mixture was stirred at T=35-40° C. for 30 min. then the solution was concentrated to residual and the residue was diluted with 300 mL of Toluene. The organic solution was concentrated to residual and the residue was diluted with 800 mL of DCM. The organic solution was concentrated to residual and the residue was diluted with 300 mL of Toluene. The organic solution was concentrated to residual and the residue was diluted with 800 mL of DCM. Acetic acid (200 mL) was added to the solution and a solution of DCDMI 26 gr in 250 mL of DCM was added in a period of 90 min. At the end of addition the mixture was stirred for 2 h at r.t. The obtained solution was added in a second round bottom flask containing a solution of 400 mL NaOH 30% and 300 mL of water. The mixture was stirred for 1 h then the phase were separated and the organic phase was washed five times with water (5×100 mL). The obtained organic solution was concentrated to residual and the residue was diluted with 500 mL of Methanol. A solution of racemic binaphthyl-phosphoric acid (abbreviated BPA) 45 gr in 700 mL was added at T=30° C. The obtained solution was stirred at r.t. for 1 h. The suspension was filtered and the solid was washed with 100 mL of Methanol.

90 gr of E-Clomiphene BPA salt were obtained.

HPLC Analysis (A/A %): 94.49% E-Clomiphene, 4.15% Z-Clomiphene.

Example 3c: Preparation of Salt of Trans-Clomiphene with Racemic Binaphthyl-Phosphoric Acid In a round bottom flask was charged 100 gr of 1-{4-[2-(Diethylamino)ethoxy]phenyl}-1,2-diphenylethanol of formula (VII), 300 mL of Toluene and 62 mL of HCl sol. 32%. The mixture was stirred at T=35-40° C. for 30' then the solution was concentrated to residual and the residue was diluted with 300 mL of Toluene. The organic solution was concentrated to residual and the residue was diluted with 300 mL of Toluene. The organic solution was concentrated to residual and the residue was diluted with 800 mL of DCM. Acetic acid (200 mL) was added to the solution and a solution of DCDMI 26 gr in 250 mL of DCM was added in a period of 90'. At the end of addition the mixture was stirred for 2 h at r.t. The obtained solution was added in a second round bottom flask containing a solution of 400 mL NaOH 30% and 300 mL of water. The mixture was stirred pro 1 h then the phase was spitted an the organic phase was washed five times with water (5×100 mL). The obtained organic solution was concentrated to residual and the residue was diluted with 500 mL of Methanol. A solution of racemic binaphthyl-phosphoric acid (abbreviated BPA) 45 gr in 1000 mL was added at T=30° C. The obtained solution was stirred at r.t. for 1 h. The suspension was filtered and the solid was washed with 100 mL of Methanol.

78.3 gr of E-Clomiphene BPA salt were obtained.

HPLC Analysis (A/A %): 96.53% E-Clomiphene, 1.51% Z-Clomiphene.

Example 3d: Preparation of Salt of Trans-Clomiphene with Racemic Binaphthyl-Phosphoric Acid In a round bottom flask was charged 100 gr of 1-{4-[2-(Diethylamino)ethoxy]phenyl}-1,2-diphenylethanol of formula (VII), 300 mL of Toluene and 62 mL of HCl sol. 32%. The mixture was stirred at T=35-40° C. for 30' then the solution was concentrated to residual and the residue was diluted with 300 mL of Toluene. The organic solution was concentrated to residual and the residue was diluted with 300 mL of Toluene. The organic solution was concentrated to residual and the residue was diluted with 300 mL of Toluene. The organic solution was concentrated to residual and the residue was diluted with 800 mL of DCM. Acetic acid (200 mL) was added to the solution and a solution of DCDMI 26 gr in 250 mL of DCM was added in a period of 90'. At the end of addition the mixture was stirred for 2 h at r.t. The obtained solution was added in a second round bottom flask containing a solution of 400 mL NaOH 30% and 300 mL of water. The mixture was stirred for 1 h then the phase was spitted an the organic phase was washed five times with water (5×100 mL). The obtained organic solution was concentrated to residual and the residue was diluted with 1000 mL of Methanol. A solution of BPA 72 gr. in 1000 mL was added at T=30° C. The obtained solution was stirred at r.t. for 1 h. The suspension was filtered and the solid was washed with 100 mL of Methanol.

119.1 gr of E-Clomiphene BPA salt were obtained.

HPLC Analysis (A/A %): 95.97% E-Chlomiphene, 3.39% Z-Clomiphene.

Example 4a: Purification of the Trans-Clomiphene Salt with Racemic Binaphthyl-Phosphoric Acid of Formula (VI)

(VI)

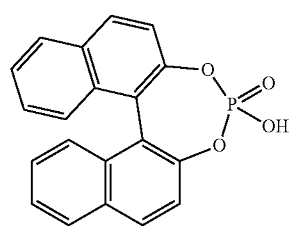

-continued

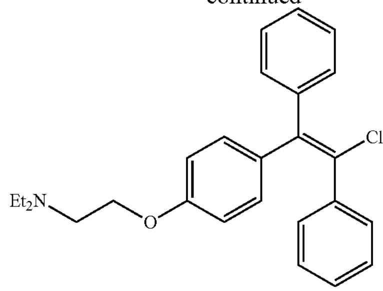

In a round bottom flask was charged 100 gr of E-Clomiphene BPA salt of formula (VI) (HPLC A/A %: 99.31% E-Clomiphene, 0.51% Z-Clomiphene) and 600 mL of Toluene. The suspension was stirred at r.t. and then 24 mL of NaOH 30% were added. Then the obtained suspension was filtered and the obtained solution was washed with 250 mL of water. The organic solution was concentrate to residual and the residue was diluted with 800 mL of Methanol. A solution of racemic binaphthyl-phosphoric acid (abbreviated BPA) 32 gr (0.515 eq) in 800 mL of Methanol was added. At the end of addition the mixture was stirred for 1 h at 30° C. the obtained suspension was filtered and the solid was wash with 100 mL of Methanol.

57.1 gr of E-Clomiphene BPA salt of formula (VI) were obtained.

HPLC Analysis (A/A %): 99.11% E-Chlomiphene, 0.03% Z-Clomiphene.

Example 4b: Purification of Trans-Clomiphene Salt with Racemic Binaphthyl-Phosphoric Acid of Formula (VI)

In a round bottom flask was charged 114 gr of E-Clomiphene BPA salt (HPLC A/A %: 99.43% E-Clomiphene, 0.35% Z-Clomiphene) and 790 mL of Toluene. The suspension was stirred at r.t. and then 28 mL of NaOH 30% were added. Then the obtained suspension was stirred for 2 h then was filtered and the obtained solution was washed with 290 mL of water. The organic solution was concentrate to residue and the residue was diluted with 920 mL of Methanol. A solution of BPA 37 gr (0.515 eq) in 920 mL of Methanol was added. At the end of addition the mixture was stirred for 1 h at 30° C. the obtained suspension was filtered and the solid was wash with 115 mL of Methanol.

58.1 gr of E-Clomiphene BPA salt were obtained.

HPLC Analysis (A/A %): 99.44% E-Chlomiphene, 0.00% Z-Clomiphene.

Example 4c: Purification of the Trans-Clomiphene Salt with Racemic Binaphthyl-Phosphoric Acid of Formula (VI)

In a round bottom flask was charged 76 gr of E-Clomiphene BPA salt (HPLC A/A %: 98.82% E-Clomiphene, 0.80% Z-Clomiphene), 500 mL of Toluene and 50 mL of water. The suspension was stirred at r.t. and then 20 mL of NaOH 30% were added. Then the obtained suspension was stirred for 2 h then was filtered and the obtained solution was washed with 190 mL of water. The organic solution was concentrate to residual and the residue was diluted with 600 mL of Methanol. A solution of BPA 28 gr (0.515 eq) in 600 mL of Methanol was added. At the end of addition the mixture was stirred for 1.5 h at 30° C. the obtained suspension was filtered and the solid was wash with 76 mL of Methanol.

53.9 gr of E-Clomiphene BPA salt were obtained.

HPLC Analysis (A/A %): 98.95% E-Chlomiphene, 0.10% Z-Clomiphene.

Example 5: Characterization of the Trans-Clomiphene Salt with Racemic Binaphthyl-Phosphoric Acid of Formula (VI)

Figure 4:
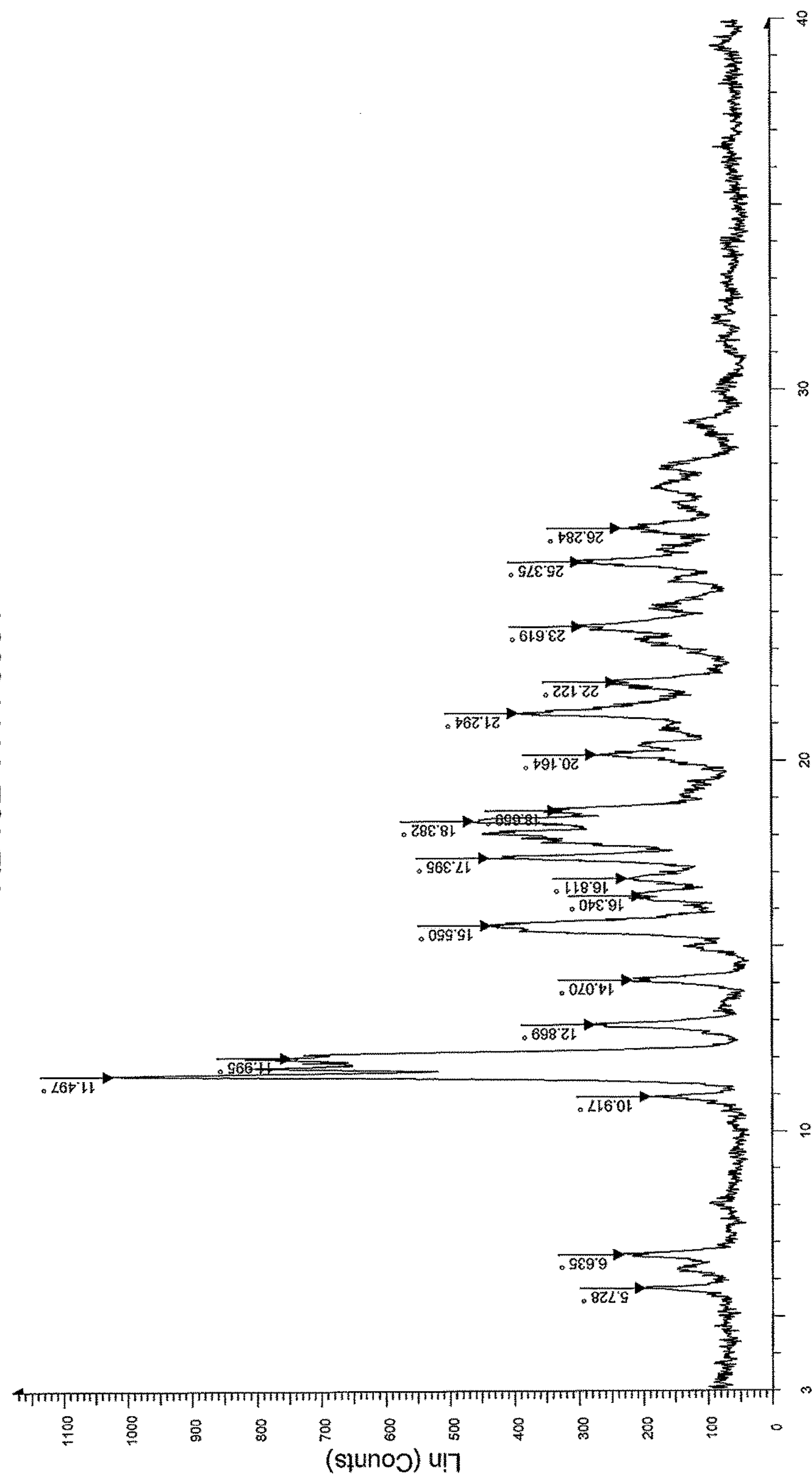
FIG. 4 shows the XPRD diffractogram of trans-Clomiphene salt with racemic binaphthyl-phosphoric acid of formula (VI).

XPRD diffractogram of the trans-Clomiphene salt with racemic binaphthyl-phosphoric acid of formula (VI) (prepared in example 4c) is shown in FIG. 4. Said crystal form is characterized by strong peaks at 2-theta values of 11.50 and 12.00.

The DSC analysis shows a melting point of 218.09° C. (onset) (see FIG. 5).

The trans configuration has been confirmed by 2D-H-NMR analysis.

Example 6a: Preparation of E-Clomiphene Citrate (1:1) from the Salt of Trans-Clomiphene with Racemic Binaphthyl-Phosphoric Acid of Formula (VI)

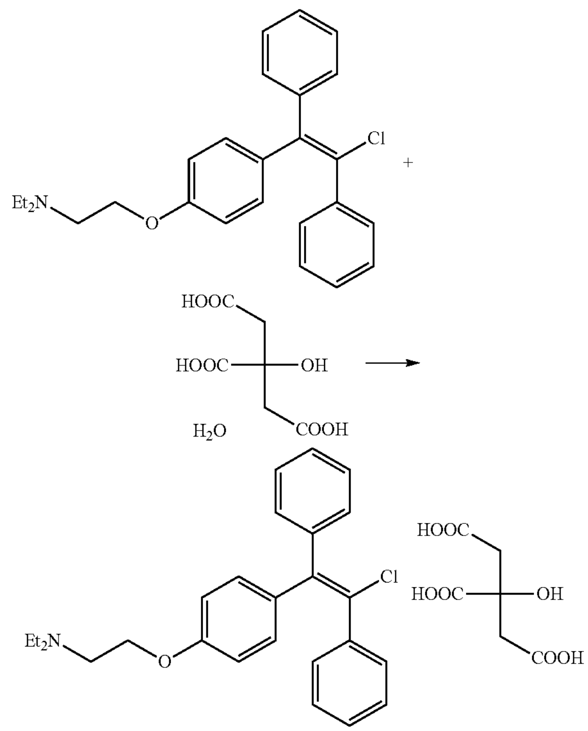

In a round bottom flask was charged 82 gr of E-Clomiphene BPA salt (HPLC A/A %: 99.40% E-Clomiphene, 0.34% Z-Clomiphene) and 500 mL of Toluene. The suspension was stirred at r.t. and then 20 mL of NaOH 30% and 50 mL of water were Methanol. Then the obtained suspension was stirred for 2 h then was filtered and the obtained solution was washed with 200 mL of water. The organic solution was concentrate to residual and the residue was diluted with 105 mL of Acetone. The solution was heated to 50° C. and a solution of citric acid monohydrate 27 gr in 166 mL of acetone was added. At the end of addition the mixture was stirred for 1 h at 0° C. The obtained suspension was filtered and the solid was washed with 50 mL of acetone.

63.3 gr of E-Clomiphene Citrate salt (1:1) were obtained.

HPLC Analysis (A/A %): 99.75% E-Chlomiphene, 0.25% Z-Clomiphene.

Example 6b: Preparation of E-Clomiphene Citrate (1:1) from Trans-Clomiphene Salt with Racemic Binaphthyl-Phosphoric Acid of Formula (VI)

In a round bottom flask was charged 125 gr of E-Clomiphene BPA salt of formula (VI) and 1050 mL of Toluene. The suspension was stirred at r.t. and then 28 mL of NaOH 30% and 50 mL of water were added. Then the obtained suspension was stirred for 2 h then was filtered and the obtained solution was washed with 250 mL of water. The organic solution was concentrate to residual and the residue was diluted with 310 mL of Acetone. The solution was heated to 50° C. and a solution of citric acid monohydrate 41.5 gr in 500 mL of Acetone was added. At the end of addition the mixture was stirred for 2 h at 0° C. the obtained suspension was filtered and the solid was wash with 125 mL of Acetone.

97.07 gr of E-Clomiphene Citrate salt were obtained.

HPLC Analysis (A/A %): 99.88% E-Chlomiphene, 0.05% Z-Clomiphene.

Example 6c: Preparation of E-Clomiphene Citrate (1:1) from the Salt of Trans-Clomiphene with Racemic Binaphthyl-Phosphoric Acid of Formula (VI)

In a round bottom flask was charged 109 gr of E-Clomiphene BPA salt of formula (VI), 950 mL of Toluene and 50 mL of water. The suspension was stirred at r.t. and then 29 mL of NaOH 30% were added. Then the obtained suspension was stirred for 2 h then was filtered and the obtained solution was washed with 220 mL of water. The organic solution was concentrate to residual and the residue was diluted with 270 mL of Acetone. The solution was heated to 50° C. and a solution of citric acid monohydrate 36 gr in 430 mL of Acetone was added. At the end of addition the mixture was stirred for 2 h at 0° C. The obtained suspension was filtered and the solid was washed with 110 mL of acetone.

82.7 gr of E-Clomiphene Citrate salt were obtained.

HPLC Analysis (A/A %): 99.90% E-Chlomiphene, 0.04% Z-Clomiphene.

K.F.=2.0%.

This solid product is characterized in Example 12.

Example 7: Synthesis of the Trans-Clomiphene Monocitrate from Trans-Clomiphene Base

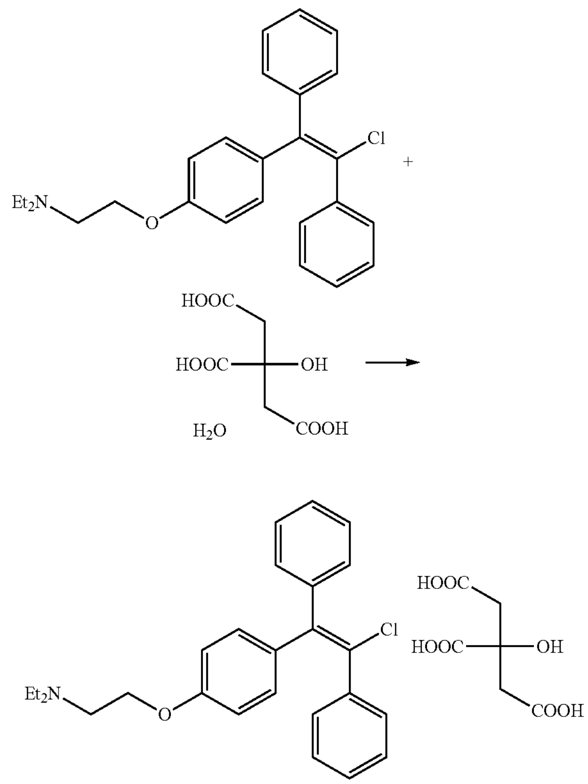

In a round bottom flask was charged 21.2 gr of E-Clomiphene free base (HPLC A/A %: 99.38% E-Clomiphene, 0.26% Z-Clomiphene) and 50 mL of acetone. The solution was heated to 50° C. and a solution of citric acid monohydrate 13.2 gr in 80 mL of Acetone was added. At the end of addition the mixture was stirred for 4-5 h at 0° C. the obtained suspension was filtered and the solid was wash with 20 mL of Acetone.

29.6 gr of E-Clomiphene monocitrate salt were obtained.

HPLC Analysis (A/A %): 99.62% E-Clomiphene, 0.38% Z-Clomiphene.

Example 8: Preparation and Characterization of the Salt of Anhydrous Trans-Clomiphene Monocitrate from Trans-Clomiphene Salt with Racemic Binaphthyl-Phosphoric Acid of Formula (VI)

In a round bottom flask was charged 155 gr of E-Clomiphene BPA salt of formula (VI), 1000 mL of Toluene and 150 mL of water. The suspension was stirred at r.t. and then 41 mL of NaOH 30% and 75 mL of MeOH were added. Then the obtained suspension was stirred then was filtered and the obtained solution was washed with 390 mL of water. The organic solution was concentrate to residual and the residue was diluted with 500 mL of Acetone. The solution was heated to 50° C. and a solution of anhydrous citric acid 40 gr in 500 mL of Acetone was added. At the end of addition the mixture was stirred for 2 h at 0° C. the obtained suspension was filtered and the solid was wash with 155 mL of Acetone. The solid was dried on vacuum at T=60° C. for 12 h.

104.8 gr of E-Clomiphene Citrate salt were obtained.

HPLC Analysis (A/A %): 99.86% E-Clomiphene, 0.07% Z-Clomiphene.

K.F.=0.9%.

Example 9: Synthesis of the Compound Des-Ethyl Clomiphene Oxalate from Clomiphene Citrate as Mixture of Cis and Trans Isomers

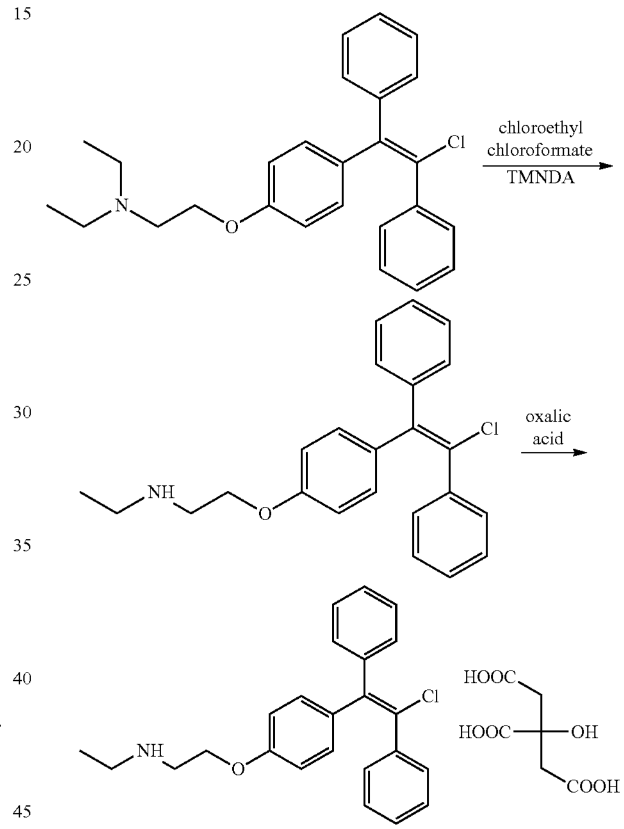

Step 1

A round bottomed flask with standard equipment was loaded with 14.7 g of clomiphene citrate, 50 mL of chlorobenzene and 50 mL of water. Into the flask, 8 mL of aqueous sodium hydroxide 30% w/w were dropped, up to pH 12. The reaction mixture was stirred, the layers were separated, the organic phase was washed with 3×20 mL of water and treated with sodium sulfate, obtaining a clear solution of Clomiphene in chlorobenzene.

Step 2

The clear solution of the previous step was treated with 8 g of tetramethylnaphtalendiamine and 5 mL of chloroethylchloroformate, then warmed to 80° C. The conversion was followed by HPLC. When the residual clomiphene was below 1%, the reaction mixture was cooled, treated slowly with 40 mL of methanol and heated to reflux for 2 hours. The methanol was then distilled off and the reaction mixture was treated with 20 mL of chlorobenzene, 30 mL of water and 8 mL of aqueous sodium hydroxide 30% w/w, up to pH 12. The layers were separated and the organic phase was dried with sodium sulfate and concentrated under vacuum to a residue, approx. 17 g. The crude product was purified by column chromatography using silica gel and eluent composed of 50 isopropyl acetate, 40 heptane, 5 dimethylethylamine. The order of elution is: Rf 0.9 tetramethylnaphthalendiamine; Rf 0.8 clomiphene; Rf 0.2 product.

The pure fractions were concentrated, obtaining 4.9 g of des-ethyl clomiphene as an oil.

Step 3

A round bottomed flask with standard equipment was loaded with 4.6 g of oil obtained in the previous step, with the addition of 13.8 mL of acetone and 0.46 g of decolorizing charcoal. After filtration, the clear solution was slowly dropped into another solution composed of 1.1 g of oxalic acid dissolved in 50.6 mL of acetone. The mixture was stirred 2 hours, filtered washing with 9.2 mL of acetone, the crude product taken up with 50.6 mL of acetone, stirred, filtered washing with 9.2 mL of acetone and dried at 50° C. under vacuum. The yield was 4.9 g of des-ethyl clomiphene oxalate.

Example 10: Analytical Method to Identify and Quantify the Impurity Des-Etil Clomiphene into Chlomiphene or Enclomiphene Chromatographic Conditions:

Column: Vydac 214TP C-4 250 mm/4.6 mm/5 μm

Temp. Column: 35° C.

Mobile Phase A: TFA 0.1% in water

Mobile Phase B: TFA 0.03% in ACN

| | Time (min) | % A | % B |
|---|---|---|---|
| Gradient: | 0 | 80 | 20 |
| | 24 | 40 | 60 |
| | 30 | 10 | 90 |
| | 31 | 80 | 20 |

Post run: 10 min.

Flow: 1.0 mL/min

Detector UV a 233 nm, bw 4 bn and 290 nm, bw 4 nm

Injection Volume: 5 μL (with needle-wash in ACN)

Run Time: 31 min

Sample diluent: $H_2O$/ACN (1:1)

Applying the conditions described above the expected retention times are as indicated below:

| Compound | RRT |
|---|---|
| Des-etil-Clomiphene - Isomer 1 | 0.93 |
| Des-etil-Clomiphene - Isomer 2 | 0.94 |
| Clomiphene or Enclomiphene | 1.00 |

Example 11: Analytical Method to Identify and Quantify Cis-Clomiphene and Trans-Clomiphene and to Determine the Purity and Ratio Thereof Chromatographic Conditions:

Dim. Column: 250 mm×4.6 mm, 5 μm

Stationaly phase: Butyl sylane (USP phase L26, Vydac 4C is suggested)

Temp. Column: room temperature

Mobile Phase: Methanol/water/triethylamine 55:45:0.3 v/v

Adjust at pH 2.5 with phosphoric acid

Flow: 1.0 mL/min

Detector UV a 233 nm,

Injection Volume: 10 μL

Sample diluent: mobile phase.

Applying the conditions described above the expected retention times are as indicated below:

| Compound | RRT |
|---|---|
| cis-Clomiphene | 1.00 |
| Trans-Clomiphene | 1.09 |

Figure 1:
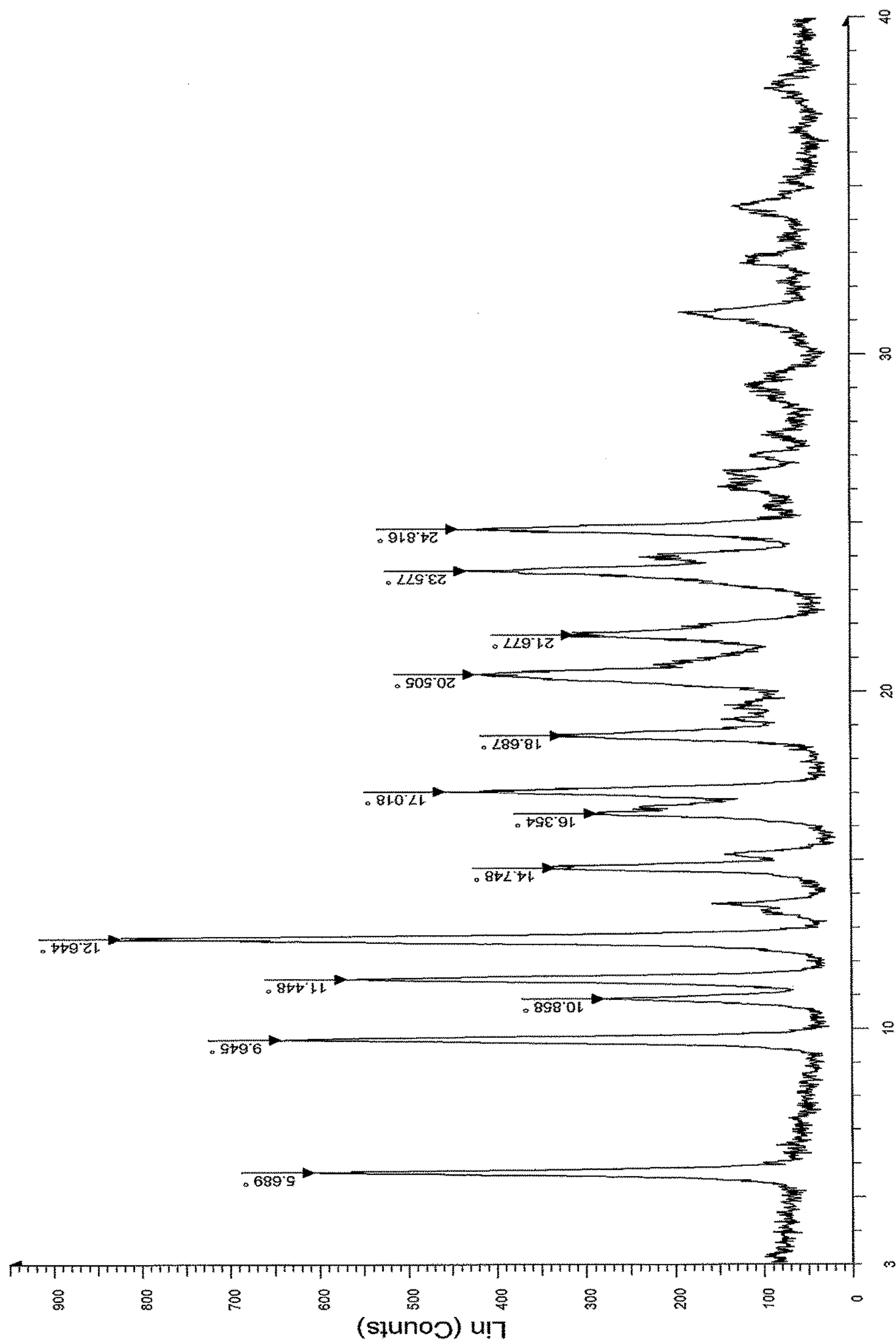
FIG. 1 shows the XPRD diffractogram of the solid form of trans-Clomiphene monocitrate, i.e. Enclomiphene citrate, crystallized from acetone.

Example 12: Characterization of the Solid Form of Trans-Clomiphene Monocitrate, i.e. Enclomiphene Citrate Having Non-Needle Crystal Habit, being Soft Polycrystalline Agglomerates, Prepared According to Example 6c XPRD Analysis XRPD analysis was performed using a PANalytical X'Pert diffractometer with Cu Kα radiation in Bragg-Brentano geometry. The system is equipped with a monodimensional, real time multiple strip detector. The diffractogram was recorded from 3° to 40° (2θ) at a scan rate of 17.6° per minute (see FIG. 1).

The solid form of trans-Clomiphene monocitrate exhibits a characteristic X-ray powder diffraction pattern with characteristic peaks expressed in 2-Theta values (2θ): 5.69 (s), 9.64 (s), 10.86 (m), 11.45 (s), 12.64 (vs), 14.75 (m), 16.35 (m), 17.02 (m), 18.69 (m), 20.51 (m), 21.68 (m), 23.58 (m), 24.82 (m), 31.2 (w); wherein (vs)=very strong intensity; (m)=medium intensity; (w)=weak intensity.

The solid form of trans-Clomiphene monocitrate exhibits a characteristic X-ray powder diffraction pattern with characteristic stronger peaks expressed in 2-Theta values (2θ): 5.69 (s), 9.64 (s), 11.45 (s), 12.64 (vs).

Crystal Habit

The solid form of trans-Clomiphene monocitrate has non-needle shaped crystal habit. Moreover, trans-Clomiphene monocitrate shows a crystalline habit as soft polycrystalline agglomerates.

Karl Fischer

Karl Fischer analyses were recorded with a Metrohm 787 KF Trinito. The product was dissolved in MeOH. Two samples were analyzed using the following reactants: Hydranal-Composite 5 (Riedel de Haën Ref. 34805), Hydranal Methanol Rapid (Riedel de Haën Ref. 37817) and Hydranal Water Standard 1.0 (Riedel de Haën Ref. 34828 used to calculate the factor).

K.F.=2.0%.

DSC

DSC analysis was recorded with a Mettler DSC822$^e$. A sample of 3.5000 mg was weighed into a 40 μL aluminium crucible with a pinhole lid and was heated, under nitrogen (50 mL/min), at 10° C./min from 30 to 300° C.

The solid form of Trans-Clomiphene citrate is characterized by an endothermic sharp peak corresponding to the melting point with an onset at 146.83° C. (fusion enthalpy −54.56 J/g), measured by DSC analysis (10° C./min). At 169.4° C. (onset) begin a broad endotermic peak.

Thus, trans-Clomiphene monocitrate shows a melting point of about 147° C. measuted by DSC (see FIG. 2).

TGA

Thermogravimetric analysis was recorded in a thermogravimetric analyzer Mettler TGA/SDTA851$^{e}$. A sample of 16.9805 mg was weighed into a 70 μL alumina crucible with a pinhole lid and was heated at 10° C./min from 30 to 280° C., under nitrogen (50 mL/min).

Figure 3:
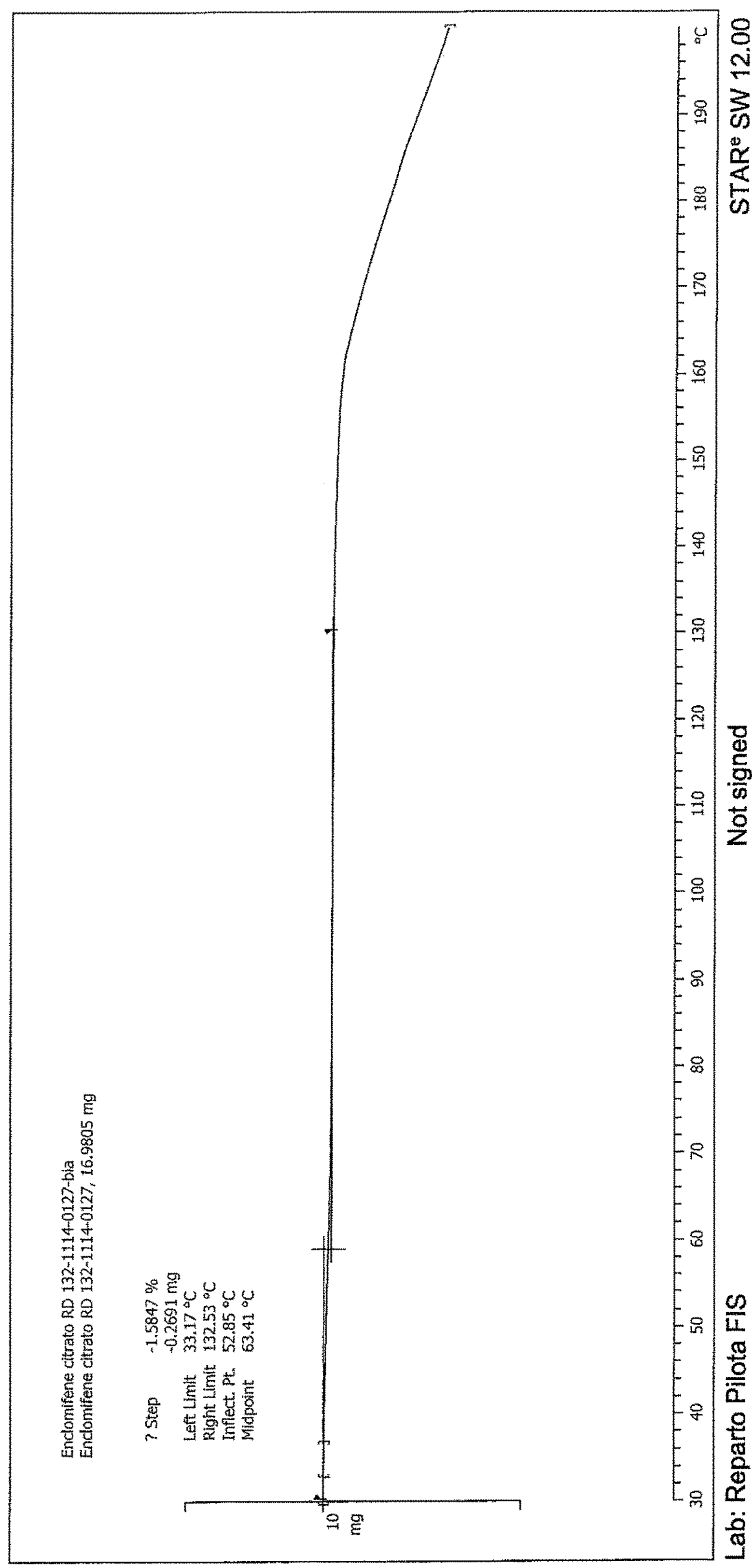
FIG. 3 shows the TGA curve of the solid form of trans-Clomiphene monocitrate crystallized from acetone.

The TG analysis of trans-Clomiphene monocitrate shows a 1.58% weight loss before the melting point well before the melting point and the boiling point of the water. This loss of weight could come from the elimination of acetone traces (see FIG. 3).

Example 13: Microscopy Analysis of Crystal Habits of Enclomiphene Citrate

The products were observed in a stereoscopic microscope Leica MZ16F and the pictures were obtained using a Leica DCF 300 FX camera. Reflected and transmitted light was used, if not specified images were taken with reflected light. For each image, the scale is specified in the picture itself.

1. Microscopy analysis of Enclomiphene citrate having non-needle crystal habit, having m.p. 147° C. (by DSC) (as prepared in example 6c).

Enclomiphene citrate crystallized from acetone with m.p. 147° C. (by DSC) (as prepared in example 6c) presents a crystal habit forming soft polycrystalline agglomerates (see FIG. 7). Fragments are plates or flakes. The solid is not transparent and does not present smooth sides. It is not possible to observe individual shape of crystals due to its small size.

2. Microscopy analysis of Enclomiphene citrate having needle shaped crystal habit, having m.p. 150° C. (by DSC) (as prepared in example 14).

Enclomiphene citrate having needle-shaped crystal habit, crystallized from ethanol with m.p. 150° C. (by DSC) (as prepared in example 14) presents a crystal habit of short needle crystal (see FIG. 8). Individual fragments are elongated, like short needles, some flattened (like straws). Needles are small but some of them are transparent, so they are monocrystalline.

3. Morphology and size comparison of Enclomiphene citrate having needle-shaped and having non-needle crystal habit.

The two products of Enclomiphene citrate present a polycrystalline structure when they were observed at microscope, in one case the small crystals were needles (crystals from ethanol) and in the other case (crystals from acetone) the crystal shape was not determined but the crystal shape of the two forms is different. Moreover, crystals form acetone seems to be formed by smaller crystals than crystals form ethanol.

In conclusions, microscopy analysis showed different crystal shapes for each crystal habit of Enclomiphene citrate:

- crystals from ethanol presents a polycrystalline structure formed by small needles,
- crystals from acetone presents a similar polycrystalline structure, but in this case the aggregation forms plates.

Example 14: Preparation of Enclomiphene Citrate Having Needle Shape Crystal Habit, by Crystallization from Ethanol A round bottom flask was charged 100 gr of E-Clomiphene BPA salt (prepared according to the same procedure as example 4a but in larger scale), 600 mL of Toluene, 77 mL of Methanol and 77 mL of water. The suspension was stirred at r.t. and then 28 mL of NaOH 30% were added. Then the obtained suspension was stirred for 1 h then was filtered. The obtained solution was splatted-off and was washed with 250 mL of water. The organic solution was concentrate to residual and the residue was diluted with 250 mL of Ethanol. The solution was heated to 40-45° C. and a solution of Citric Acid 28.6 gr in 400 mL of Ethanol was added. At the end of addition the mixture was stirred for 1 h at 0° C. the obtained suspension was filtered and the solid was wash with 100 mL of Ethanol. The product was dried under vacuum at 60° C. overnights.

71.9 gr of E-Clomiphene Citrate salt, as crystalline white salt, were obtained.

Example 15: Characterization of Enclomiphene Citrate Crystal Habits by XRPD Analysis XRPD analysis was performed using a PANalytical X'Pert diffractometer with Cu Kα radiation in Bragg-Brentano geometry. The system is equipped with a monodimensional, real time multiple strip detector. The diffractogram was recorded from 3° to 40° (2θ) at a scan rate of 0.0205° per second.

1. Enclomiphene citrate having non-needle crystal habit (as prepared in example 6c) is a white homogeneous white powder the XRPD diffractogram of the which is showed in FIG. 1

Figure 9:
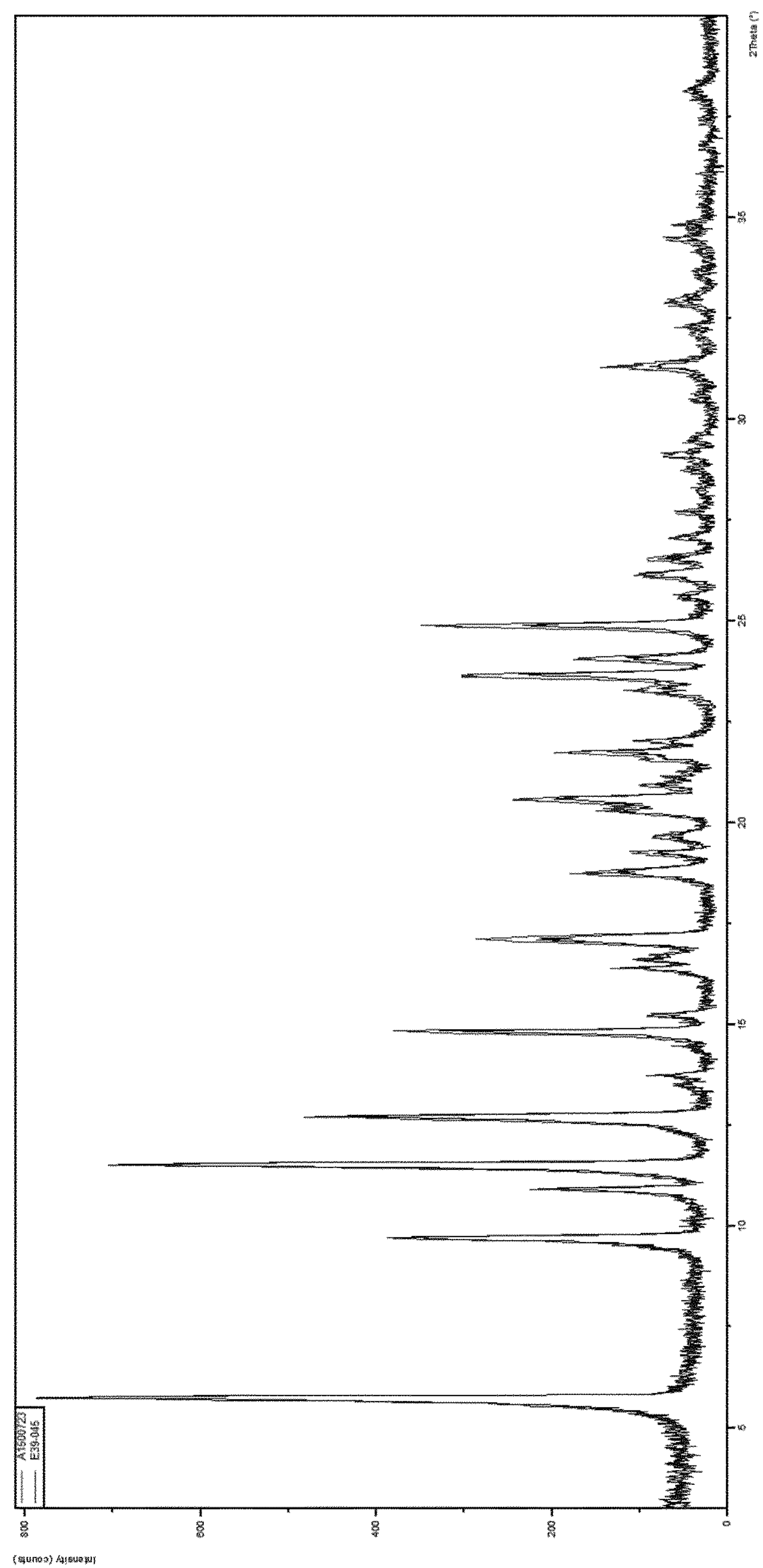
FIG. 9 shows the XPRD diffractogram of the solid form of Enclomiphene citrate having needle crystal habit, crystallized from ethanol (with or without a gentle milling treatment).
Figure 10:
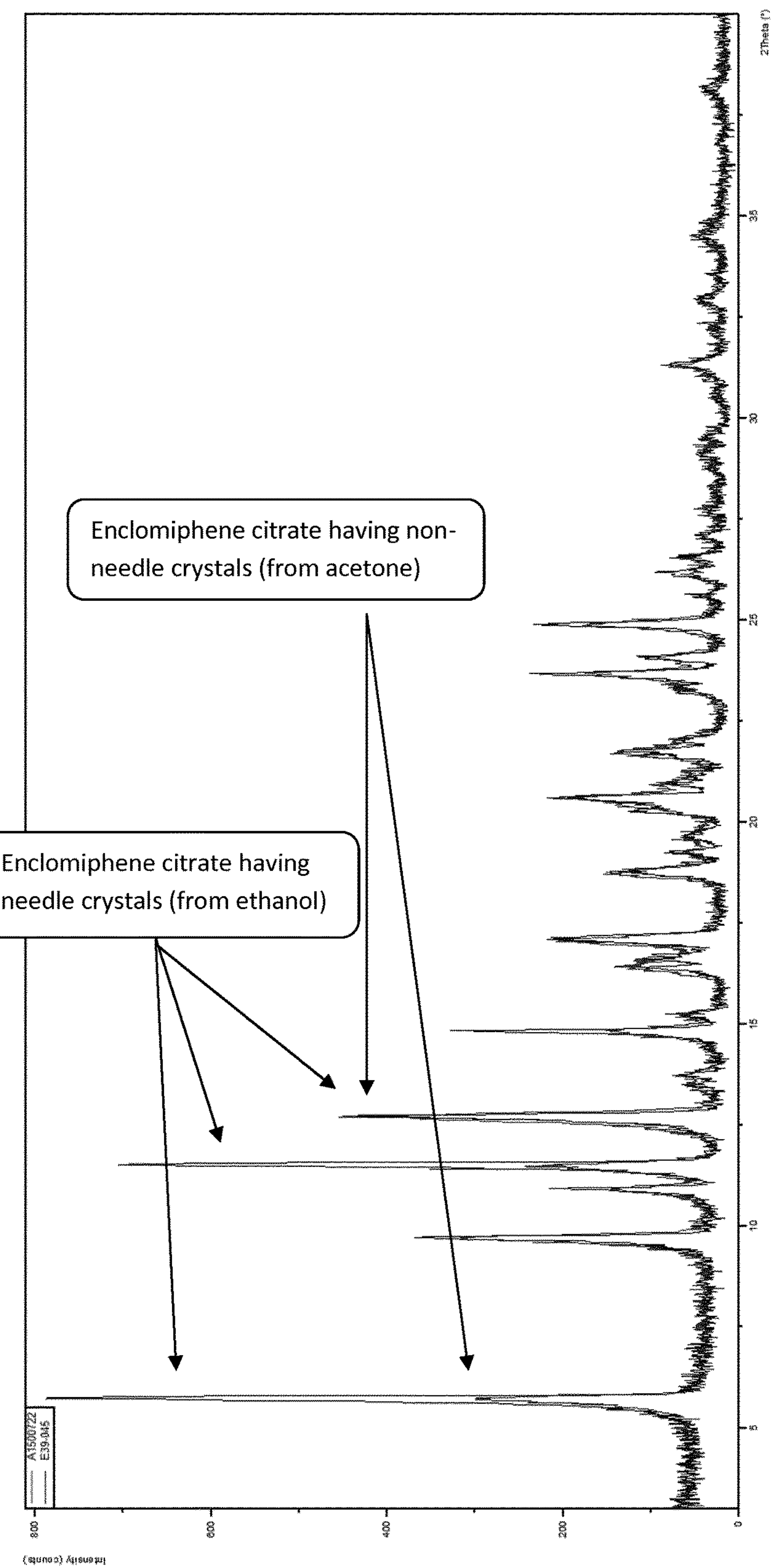
FIG. 10 shows a comparison of XRPD diffractograms of samples of Enclomiphene citrate having needle crystals and having non-needle crystals, as crystallized respectively from ethanol or from acetone.

2. Enclomiphene citrate having needle-crystal habit (as prepared in example 14) was analyzed and the XRPD diffractogram, aquired before and after a gentle milling treatment (in order to confirm that crystalline morphology was not affected by a gentle milling treatment, which is the case), is shown in FIG. 9.

3. Comparison of XRPD diffractograms of samples of Enclomifene citrate having non-needle crystals (obtained by crystallization from acetone) and milled Enclomifene citrate having needle crystal (obtained by crystallization from ethanol) indicated some differences of peak intensity, only, since the position of the peaks is the same for both the samples, as shown in comparative FIG. 10 and the following table:

| Peak Position [°2Th.] | Encl. citrate non-needle cryst. (prep. exp. 6c) Rel. Int. [%] | Encl. citrate needle cryst. (prep. exp. 14) Rel. Int. [%] |
|---|---|---|
| 5.8 | 61 | **100** |
| 9.7 | 61 | 39 |
| 10.9 | 22 | 25 |
| 11.5 | 44 | **86** |
| 12.7 | **100** | 61 |
| 13.5 | 11 | 3 |
| 13.8 | 7 | 7 |
| 14.9 | 26 | **47** |
| 15.3 | 8 | 10 |
| 16.4 | 26 | 14 |
| 16.7 | <1 | 9 |
| 17.1 | 40 | 25 |
| 18.7 | 23 | 18 |
| 19.3 | 13 | 11 |
| 19.6 | 6 | 8 |
| 20.3 | <1 | 15 |
| 20.6 | 40 | 25 |
| 21.0 | 20 | 9 |
| 21.6 | <1 | 9 |
| 21.8 | 26 | 22 |
| 22.1 | <1 | 11 |
| 23.3 | <1 | 11 |
| 23.6 | 45 | 38 |

-continued

| Peak Position [°2Th.] | Encl. citrate non-needle cryst. (prep. exp. 6c) Rel. Int. [%] | Encl. citrate needle cryst. (prep. exp. 14) Rel. Int. [%] |
|---|---|---|
| 23.7 | 32 | 36 |
| 24.1 | 16 | 22 |
| 24.9 | 33 | 44 |
| 25.7 | <1 | 3 |
| 26.2 | 5 | 9 |
| 26.6 | 7 | 9 |
| 27.1 | 4 | 5 |
| 27.7 | <1 | 4 |
| 28.8 | <1 | 3 |
| 29.1 | 4 | 6 |
| 29.5 | <1 | 3 |
| 30.6 | <1 | 2 |
| 31.3 | 11 | 16 |
| 32.4 | <1 | 3 |
| 32.9 | 4 | 6 |
| 33.6 | <1 | 2 |
| 34.5 | 7 | 6 |
| 34.9 | <1 | 4 |
| 36.8 | <1 | 2 |
| 38.1 | 3 | 4 |

Some peak intensities are highlighted in bold character since they are remarkably different in comparison to the other solid form of Enclomiphene citrate.

Different relative intensities for the two crystal forms of Enclomiphene citrate were observed due to the preferential orientation caused by the crystal morphology.

In particular, Enclomiphene citrate having needle crystals habit has a characteristic X-ray powder diffraction pattern with characteristic peaks expressed in 2-Theta values (2θ) at: 5.8 (vs), 11.5 (vs); wherein (vs)=very strong intensity.

More in particular, Enclomiphene citrate having needle crystals habit has a characteristic X-ray powder diffraction pattern with characteristic peaks expressed in 2-Theta values (2θ) at: 5.8 (vs), 11.5 (vs), 12.7 (s), 14.9 (s) and 24.9 (s); wherein (vs)=very strong intensity; (s)=strong intensity.

Again more particularly, Enclomiphene citrate having needle crystals habit has a characteristic X-ray powder diffraction pattern with characteristic peaks expressed in 2-Theta values (2θ) at: 5.8 (vs), 9.7 (m), 10.9 (m), 11.5 (vs), 12.7 (s), 14.9 (s), 17.1 (m), 20.6 (m), 21.8 (m), 23.6 (m), 23.7 (m) and 24.9 (s); wherein (vs)=very strong intensity, (s)=strong intensity, (m)=medium intensity.

The meaning given above for (vs)=very strong intensity, (s)=strong intensity, (m)=medium intensity refer to the following relative intensities percentages:

(vs)=very strong intensity means Rel. Int [%] in the range 81-100, (s)=strong intensity means Rel. Int [%] in the range 80-40, (m)=medium intensity means Rel. Int [%] in the range 39-20.

In particular, using the peak at 2-Theta value (2θ) 12.7° as peak intensity reference, it is clear that peaks at 5.8° and 11.5° (2θ) of the sample of Enclomifene citrate having needle shaped crystal habit have much more higher relative intensities than sample of Enclomifene citrate having non-needle shaped crystal habit, while the other peaks have similar intensity.

In Enclomifene citrate having needle shaped crystal habit (crystallized from ethanol), using the peak at 2-Theta value (2θ) 12.7° as peak intensity reference, such a peak having a relative intensity of 61%, the peaks at 5.8 and 11.5° (2θ) have higher relative intensities, in particular, have respectively relative intensity of 100% and 86%.

In the case of Enclomifene citrate having needle shaped crystal habit, this difference of intensity comes from the orientation preferential of the crystals caused by the needle shape.

Example 16: Preparation of Enclomiphene Citrate Having Needle Shape Crystal Habit, by Crystallization from Ethanol

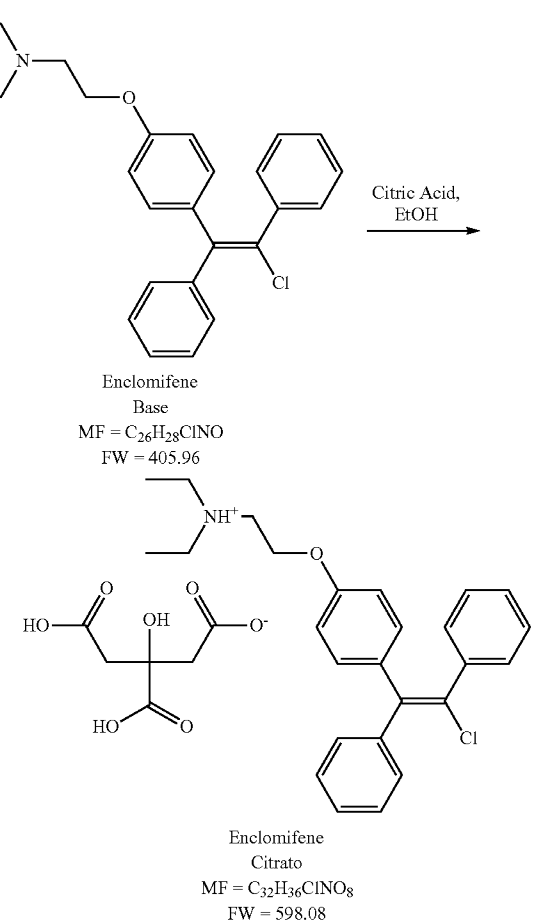

A round bottom flask, equipped with thermometer, reflux condenser, impeller and dropping funnel was filled with nitrogen and charged with: 2.0 g (1 equiv.) of Enclomiphene base having primastic shaped crystal habit (prepared in example 27) [HPLC profile of the starting material Enclomiphene base: Enclomiphene 99.83% A/A %, Cis-Clomiphene 0.03% A/A %, other impurities 0.14% A/A %] and 2.0 mL of absolute ethanol. the mixture was heated up to 50° C. in order to dissolve the crude, than a solution composed by 1.04 g (1.1 equiv) of anhydrous citric acid in 8.0 mL (8V) of absolute ethanol was added slowly and at the same temperature. The mixture was slowly cooled down to 0° C., and allowed to stir for 2 h. The suspension was filtered by suction filtration and the cake was washed with 2 mL (1V) of cold absolute ethanol. The thus obtained product was dried under vacuum at 50° C. for 8 h. This procedure afforded 2.80 g (95.0% yield) of Enclomifene citrate as white thin needles, i.e. Enclomiphene citrate having needle shaped crystal habit.

HPLC profile of Enclomiphene citrate: Enclomiphene 99.92 A/A %; Cis-Clomiphene 0.03% A/A %, other impurities 0.04% A/A %.

Example 17: Studies of Solubility of Enclomiphene Citrate Crystal Habits Forms

To determine the effect of the crystal size and morphology over the solubility of the different solid forms of Enclomiphene citrate, kinetic solubility studies were carried out in water and buffered aqueous solutions. Solubility was determined by HPLC analysis, by comparison of the area corresponding to Enclomiphene HPLC peak.

For each solubility study, the following parameters were monitored:

intensity of Enclomiphene peak for each replicate of the assay average value standard deviation.

Experimental Procedure

To carry out the solubility studies, 400 mg of each product (not grinded) was stirred in water (24 ml, 60 v) under the same conditions of stirring speed (magnetic stirring at 1000 rpm with a 2 cm "rugby shape" stir bar), flask used (round bottom flask of 50 ml of capacity with a 29/32 neck), etc. Alliquotes of ca 6 ml of suspension were filtered at different times: 15, 45, 90 and 180 min. After filtration, mother liquors were directly analyzed by HPLC (doing 2 replicates for each analysis) and its pH was determined. The filtered solid was analyzed by XRPD. The solubility analysis was repeated for each product and comparison of solubility was determined by the differences of HPLC area.

Below an HPLC method that allow to have a fast determination of Enclomiphene solubility:

| | |
|---|---|
| Column | C18 Zorbax Eclipse (XDB) 150 × 4.6 mm, 5□m |
| Mobile phase | (H2O—H3PO4 0.1%:ACN 95:5)/ACN (60:40)-6 min-(30:70)-3 min-(30:70); Post run 3 min |
| Temperature | 25° C. |
| Flow | 1.5 mL/min |
| Wavelength | 240 nm |
| Injection volumen | 25 □L of mother liquors |
| Stop time | 9 min (+3 min de post time) |
| Retention time | Rt (Enclomiphene) = 3.1 min<br>Rt (citric acid) = 0.9 min |

These HPLC conditions were used to perform solubility analysis.

Solubility Studies in Water

Initially the solubility of Enclomiphene citrate in water was carried out by duplicate. However as we observed a high standard variation for some HPLC analysis between both duplicates, these assays were done by triplicate. For each Enclomiphene citrate samples, the results are shown in the following tables: Table 1 for Enclomiphene citrate having non-needle crystals (m.p. 147° C., lot 722, and Table 2 for Enclomiphene citrate having needle crystals (m.p. 150° C.)), lot 723.

TABLE 1

Results of water solubility studies of Enclomiphene citrate having non-needle crystals:

| Time min | HPLC a/a | HPLC a/a | HPLC a/a | average HPLC a/a | SD |
|---|---|---|---|---|---|
| 0 | 0 | 0 | 0 | 0 | 0 |
| 15 | 1819 | 3483 | 3273 | 2858 | 906 |
| 45 | 3083 | 3370 | 3225 | 3226 | 144 |
| 90 | 3229 | 2099 | 2988 | 2772 | 595 |
| 180 | 2991 | 3597 | 3208 | 3265 | 307 |

TABLE 2

Results of water solubility studies of Enclomiphene citrate having needle crystals:

| Time min | HPLC a/a | HPLC a/a | HPLC a/a | average a/a | SD |
|---|---|---|---|---|---|
| 0 | 0 | 0 | 0 | 0 | 0 |
| 15 | 4099 | 6104 | 3273 | 5152 | 1006 |
| 45 | 5206 | 5457 | 3225 | 4962 | 652 |
| 90 | 5085 | 5426 | 2988 | 5334 | 218 |
| 180 | 4120 | 5327 | 3208 | 4126 | 1198 |

The HPLC a/a average values of solubility of the two solid forms of Enclomiphene citrate were plotted against time:

See FIG. 26

Solubility of Enclomiphene citrate having needle shaped crystal habit is higher than Enclomiphene citrate having non-needle shaped crystal habit over three hours, although this difference of solubility seems to decrease with time. Indeed the solubility of needle crystals seems to decrease with time and could be similar to the solubility of non-needle crystals after 3 hour taking into consideration the experimental error from the different replicates (SD). Therefore the crystal size and habit of Enclomiphene citrate with needle crystals seems to produce a higher kinetic solubility that decreases with time affording after three hour a solubility similar to of Enclomiphene citrate having non-needle crystals. However Enclomiphene citrate having needle shaped crystal habit is more soluble (almost two times) than Enclomiphene citrate having non-needle shaped crystal habit.

Solubility Studies at pH 4.5

Solubility at a slightly acid medium was determined at pH 4.5 buffer used was a mixture acetic acid/sodium acetate prepared according to USP specifications.

The solubility of Enclomiphene citrate having non-needle and needle crystals in 4.5 pH buffer was carried out by duplicate. In this case the reproducibility was better than in the analysis of citrates with water.

The results are shown in the following tables (Table 3 for Enclomiphene citrate having non-needle, lot 722, and Table 4 for Enclomiphene citrate having needle crystals, lot 723).

TABLE 3

Results of solubility study of Enclomiphene citrate having non-needle crystals at pH = 4.5.

| Time min | HPLC a/a | HPLC a/a | Average a/a | SD |
|---|---|---|---|---|
| 0 | 0 | 0 | 0 | 0 |
| 15 | 1294 | 1077 | 1185 | 154 |
| 45 | 907 | 941 | 924 | 24 |

TABLE 3-continued

| Results of solubility study of Enclomiphene citrate having non-needle crystals at pH = 4.5. | | | | |
|---|---|---|---|---|
| Time min | HPLC a/a | HPLC a/a | Average a/a | SD |
| 90 | 1279 | 912 | 1095 | 260 |
| 180 | 1008 | 1096 | 1052 | 62 |

TABLE 4

| Results of solubility study of Enclomiphene citrate having needle crystals at pH = 4.5. | | | | |
|---|---|---|---|---|
| Time min | HPLC a/a | HPLC a/a | Average a/a | SD |
| 0 | 0 | 0 | 0 | 0 |
| 15 | 3941 | 4330 | 4135 | 275 |
| 45 | 3978 | 4070 | 4024 | 65 |
| 90 | 4889 | 5329 | 5109 | 311 |
| 180 | 5098 | 5060 | 5079 | 27 |

The HPLC A/A average values of solubility of the two solid forms of Enclomiphene citrate were plotted against time:

See FIG. 27

From the plot above, it can be observed very different dissolution curves between the two Enclomiphene citrate crystal habit forms. The solubility of Enclomiphene citrate having needle crystals (lot 723) was about 4 to 5 times higher than solubility of Enclomiphene citrate having non-needle crystals (lot 722) and this difference of solubility seems to increase or maintain with time. Therefore in this case, the differences in the crystal size and habit play a crucial role in determining the solubility of Enclomiphene citrate.

Thus, Enclomiphene citrate having needle crystals of the present invention is much more soluble at pH 4.5 than Enclomiphene citrate having non-needle crystals, in particular about 4 to 5 times more soluble.

Therefore, either in water and at pH 4.5 Enclomiphene citrate having needle crystals of the present invention is more soluble than Enclomiphene citrate having non-needle crystals. However, the extent of this effect is much more evident in a pH 4.5 buffered solution than in pure water.

Example 18: Preparation of Enclomiphene Base Having Prismatic Shaped Crystal Habit, by Crystallization from Ethanol A round bottom flask was charged 100 gr of Clomiphene BPA salt (prepared according to the same procedure as example 4a but in larger scale), 600 mL of Toluene, 77 mL of Methanol and 77 mL of water. The suspension was stirred at r.t. and then 28 mL of NaOH 30% were added. Then the obtained suspension was stirred for 1 h then was filtered. The obtained solution was splatted-off and was washed with 250 mL of water. The organic solution was concentrate to residual and the residue was diluted with 250 mL of Ethanol. The mixture was stirred for 1 h at 0° C. The obtained suspension was filtered and the solid was wash with 100 mL of Ethanol.

The very crystalline solid, having the appearance of large and transparent crystals, macrocrystals, was dried under vacuum at 60° C. overnight.

36.4 gr of E-Clomiphene base, being very crystalline, were obtained. DSC analysis in FIG. 17.

Example 19: Preparation of Enclomiphene (Base) Having Non-Prismatic Shaped Crystal Habit In a round bottom flask was charged 60 gr of Clomiphene BPA salt (prepared according to the same procedure as example 4a but in larger scale), 360 mL of Toluene, 46 mL of Methanol and 46 mL of water. The suspension was stirred at r.t. and then 17 mL of NaOH 30% were added. Then the obtained suspension was stirred for 1 h then was filtered. The obtained solution was splatted-off and was washed with 150 mL of water. The organic solution was concentrate to residual and the residue was diluted with 90 mL of Ethanol denatured toluene. The mixture was stirred for 1 h at −10° C. the obtained suspension was filtered and the solid was wash with 30 mL of Ethanol denatured toluene.

The solid was dried under vacuum at 60° C. overnight.

25.4 gr of E-Clomiphene (base) were obtained. DSC analysis in FIG. 16.

Example 20: Microscopy Analysis of Crystal Habits of Enclomiphene (Base)

The product of examples 18 and 19 were observed in a stereoscopic microscope Leica MZ16F and the pictures were obtained using a Leica DCF 300 FX camera. Reflected and transmitted light was used, if not specified images were taken with reflected light. For each image, the scale is specified in the picture itself.

Enclomiphene (base) having prismatic shaped crystal habit (prepared according to example 18) (see FIG. 11 or 11-BIS) presents colorless transparent prisms, some are very short and other more elongated. They are relative large single crystals with well-defined sides and edges.

The name of the crystals in the image must be "prisms" or "short prisms", "long prisms" or "oblique prisms" and "short oblique prisms", "long oblique prisms" and so on, depending on their length. At most it can be stated that when the prisms are short some of them resemble a rhombohedron or are rhombohedral-like. Nevertheless, although the shortest prisms shown in the image remind the regular form called rhombohedron, said term cannot be used to described to crystals of the invention since said term implies a crystal symmetry that is obviously not the one of this crystalline structure.

Enclomiphene (base) having non-prismatic shaped crystal habit (prepared according to example 19) (see FIG. 12 or 12-BIS) presents a crystal habit forming soft polycrystalline agglomerates. Individual fragments are short needles, very small.

Microscopy analysis of the both Enclomiphene base having prismatic or non-prismatic shaped crystal habit indicated significant differences in crystal habit: Enclomiphene crystallized from ethanol (only) of example 18 presents bigger and well defined single crystals whereas Enclomiphene of example 19 presents polycrystalline aggregates formed by small needles. The different morphology of Enclomiphene crystals is well evident also by visual observation.

Microscopy analysis showed different crystal shapes for each batch, in particular:

Enclomiphene having non-prismatic shaped crystal habit (see example 19) shows polycrystalline aggregates of small needles (see FIGS. 12 and 12-BIS).

Enclomiphene having prismatic shaped crystal habit (see example 18) shows big transparent monocrystalline prisms (see FIGS. 11 and 11-BIS).

Example 21: Characterization of Enclomiphene (Base) Crystal Habits by XRPD Analysis XRPD analysis was performed using a PANalytical X'Pert diffractometer with Cu Kα radiation in Bragg-Brentano geometry. The system is equipped with a monodimensional, real time multiple strip detector. The diffractogram was recorded from 3° to 40° (2θ) at a scan rate of 0.0205° per second.

Figure 13:
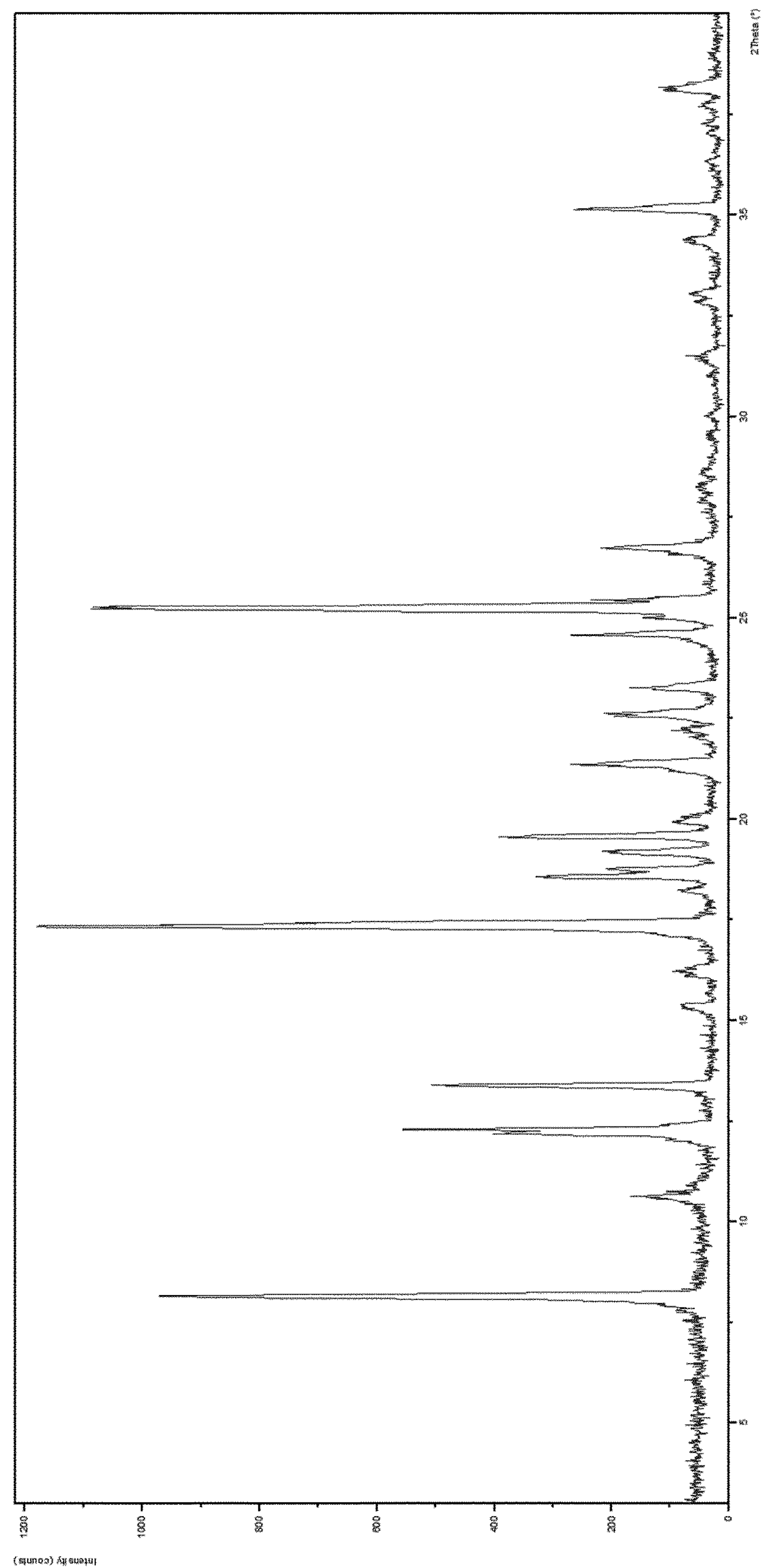
FIG. 13 shows the XPRD diffractogram of the solid form of Enclomiphene (base) having prismatic crystal habit.

1. Enclomiphene (base) having prismatic shaped crystal habit (crystallized from ethanol, as prepared in example 18) shows the XRPD diffractogram of FIG. 13.

Figure 14:
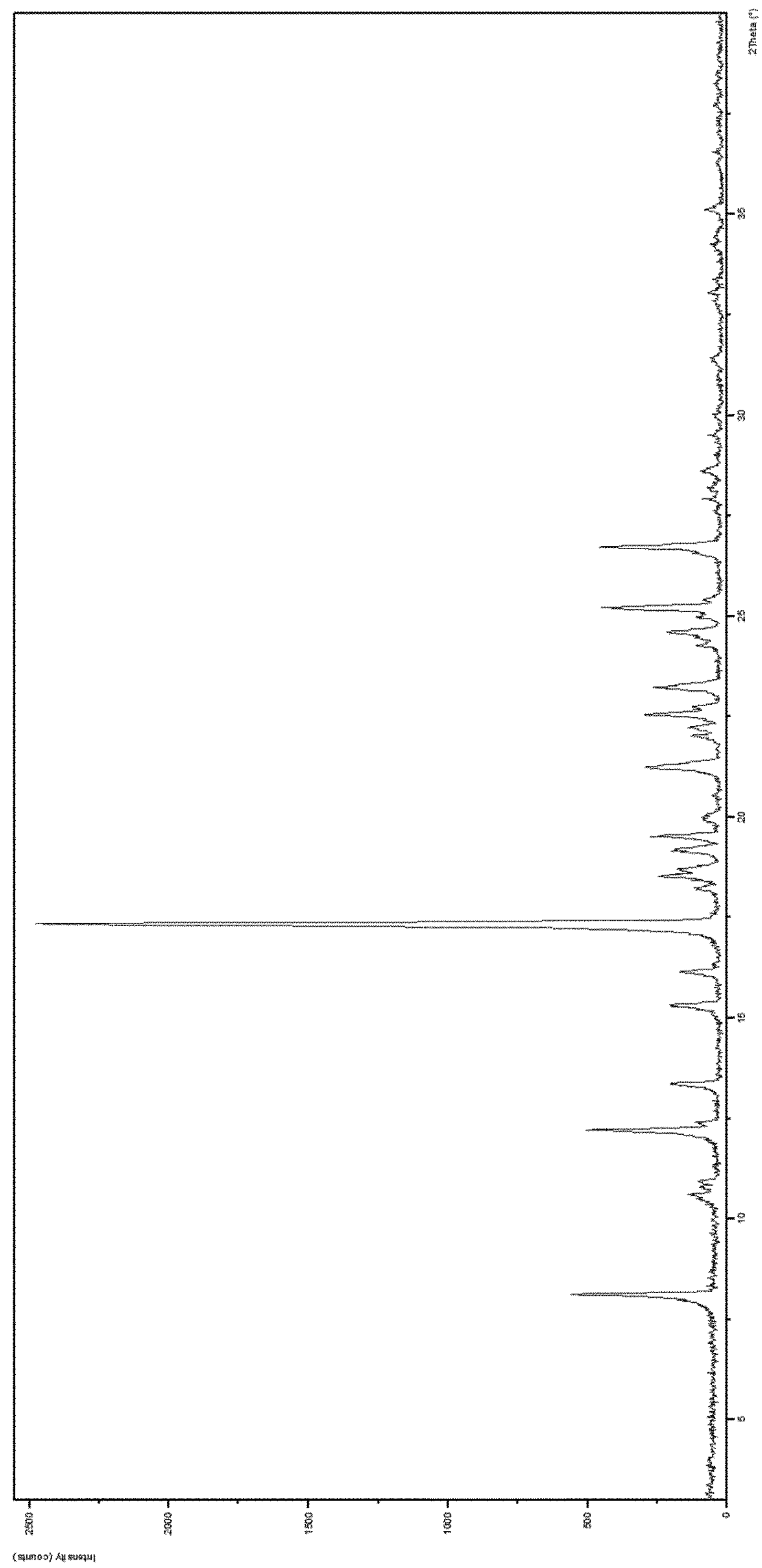
FIG. 14 shows the XPRD diffractogram of the solid form of Enclomiphene (base) having non-prismatic crystal habit.

2. Enclomiphene (base) having non-prismatic shaped crystal habit (crystallized from ethanol denatured toluene, as prepared in example 19) shows the XRPD diffractogram of FIG. 14.

3. The comparison of diffractograms of samples of Enclomiphene having prismatic or non-prismatic shaped crystal habit (see FIG. 15) indicated the same crystalline form with very different relative peak intensity for some of the peaks (such as at 2-theta values (2θ) of 8.15°, 12.33°, 13.41°, 21.38°, 25.23°, 35.17°, 38.10°). The intensity of these peaks is much lower in the case of Enclomiphene having non-prismatic shaped crystal habit, while other peaks have similar intensity (at 2-theta values (2θ) of 15.34°, 17.34°, 18.21° and 23.28°). The different crystal habit observed for both batches, big prisms for Enclomiphene having prismatic shaped crystal habit and very little needles for Enclomiphene having non-prismatic explains these differences.

The following table shows the comparison of relative XPRD spectrum intensities between Enclomiphene having prismatic crystals, as prepared by crystallization form ethanol, and Enclomiphene as prepared in example 19, not having prism crystal habit.

| peak position (of Enclomiphene of example 18) | Enclomiphene of example 18, i.e. Enclomiphene PRIMATIC crystals Rel. Int [%] | Enclomiphene of example 19, i.e. Enclomiphene non-PRIMATIC crystals Rel. Int. [%] |
|---|---|---|
| 8.1 | **80** | **19** |
| 10.6 | 9 | 4 |
| 10.9 | <1 | 3 |
| 12.2 | 27 | 19 |
| 12.3 | **45** | **<1** |
| 12.4 | <1 | 3 |
| 13.4 | **42** | **7** |
| 15.4 | 4 | 7 |
| 16.2 | 4 | 6 |
| 17.3 | 100 | 100 |
| 17.5 | **44** | **<1** |
| 18.2 | 4 | 2 |
| 18.5 | **23** | **8** |
| 18.7 | **15** | **4** |
| 19.2 | **15** | **6** |
| 19.5 | **30** | **8** |
| 19.9 | 6 | 2 |
| 21.2 | <1 | 11 |
| 21.3 | **18** | **<1** |
| 22.0 | 3 | 4 |
| 22.2 | 5 | 4 |
| 22.6 | 13 | 11 |
| 22.7 | <1 | 3 |
| 23.2 | 12 | 9 |
| 24.3 | <1 | 3 |
| 24.6 | **21** | **7** |
| 25.0 | <1 | 3 |
| 25.2 | **89** | **17** |
| 25.3 | **93** | **<1** |
| 25.4 | **17** | **<1** |
| 26.7 | **17** | 17 |
| 27.9 | 1 | <1 |
| 28.2 | <1 | 1 |
| 28.3 | 1 | <1 |
| 28.6 | 1 | 2 |
| 29.5 | 1 | 1 |
| 30.0 | 1 | <1 |
| 31.0 | 1 | <1 |
| 31.5 | 3 | 1 |
| 32.8 | 3 | <1 |
| 33.0 | 3 | 2 |
| 34.2 | <1 | 1 |
| 34.4 | 4 | <1 |

The most intense peak at 2-Theta value of 17.3 has been used as reference for calculating the relative intensities for both the crystal structures.

Example 22: Study of Flowability of Enclomiphene (Base) Crystal Habits by XRPD Analysis Flowability was determined by an in-house method using a glass funnel (diameter 80 mm—stem diameter 10 mm—stem length 75 mm) with approximately 5 g of product repeating the process three times (in the cases in which flowability was observed). Different parameters were observed:

Flow or not

Need of percussion

Time to pass through the funnel

Very different behaviors between both batches both batches of Enclomiphene base were observed:

Enclomiphene having prismatic shaped crystal habit (as prepared in example 18): although some percussions were needed, the product flowed through the funnel in a short time 10 s.

Enclomiphene having non-prismatic shaped crystal habit (as prepared in example 19): the solid the solid did not flow. However with constant percussion it passed through the funnel very slowly after 130 s.

| Batch number | Flow? Percussion needed? time | Flow? Percussion needed? time | Flow? Percussion needed? time |
|---|---|---|---|
| Enclomiphene base (example 18) | Yes<br>Yes<br>15 s | Yes<br>Yes<br>12 s | Yes<br>yes<br>14 s |

-continued

| Batch number | Flow? Percussion needed? time | Flow? Percussion needed? time | Flow? Percussion needed? time |
|---|---|---|---|
| Enclomiphene base (example 19) | No (static electricity) Yes (if constant) 130 s* | — | — |

*time necessary to made the solid pass through the funnel with constant percussion.

Very different behaviors between both batches both batches of Enclomiphene base were observed as results of the flowability studies.

The products that did not flow correspond to the solid that crystallize forming polycrystalline aggregates of sharp needles (Enclomiphene prepared in example 19). These crystal needles produce a bad flowability in comparison to the bigger monocrystalline prism (Enclomiphene having prismatic crystal habit, as prepared in example 18) that flowed in short times.

Example 23: Study of Density of Enclomiphene (Base) Crystal Habits

Density was determined by an in-house method measuring the filled space by a sample of 500 mg in a test tube before and after hitting the tube (bulk and tapped density, respectively):

| Batch number | bulk density | tapped density | Reduced space (bulk vs tapped) |
|---|---|---|---|
| Enclomiphene (example 18) | 8 mm | 8 mm | 0% |
| Enclomiphene (example 19) | 17 mm | 13 mm | 24% |

Table summarizing the density determination for the different batches of Enclomiphene base.

Different behaviors between both batches of Enclomiphene base were observed for the bulk density:

Enclomiphene base having prismatic crystal habit, prepared by crystallization from ethanol (of example 18) presents a higher bulk density than Enclomiphene having non-prismatic crystal habit (of example 19) (respectively 8 and 24 mm). After tube hitting, tapped density is higher than bulk density for Enclomiphene base having non-prismatic crystal habit, while it remains unchanged for Enclomiphene base having prismatic shaped crystal habit. However tapped density of Enclomiphene base having prismatic crystal habit remains higher than for Enclomiphene base having non-prismatic crystal habit (respectively 8 mm and 13 mm).

Enclomiphene base obtained by crystallization form ethanol, i.e. Enclomiphene having prismatic shaped crystal habit, affords the best bulk density. This is not the case of Enclomiphene base having non-prismatic shaped crystal habit (of example 19) where the sharp needles caused a worse packing with higher empty spaces, even if a hitting allowed to reduce this void.

The crystal habit thus also plays an important role in the density of Enclomiphene.

The compressibility index calculated from bulk and tapped densities can be used to estimate the flow characteristics of the powder. Following the rule described in the article Chem Eng 1965; 72:163-168, it can be considered that the flow character should be:

Excellent for Enclomiphene base having prismatic shaped crystal habit,

Passable for Enclomiphene base having non-prismatic shaped crystal habit (of example 19).

In conclusion, Enclomiphene having prismatic shaped crystal habit, i.e. Enclomiphene composed by large single crystals of prism shape, provide much better flowability, bulk density, tapped density and excellent compressibility index, in comparison to Enclomiphene being polycrystalline aggregates of short needles, i.e. Enclomiphene having non-prismatic shaped crystal habit as prepared in example 19.

The solid form being Enclomiphene having prismatic shaped crystal habit thus allows to save space in the warehouse and in the containers for transportation. Moreover, this form provides evident advantages in the processing for preparing Enclomiphene citrate (e.g. charging into the reactors) or for preparing pharmaceutical composition of Enclomiphene because of his improved flowability.

Finally, it has been also found that the solubility of Enclomiphene base is much higher than Enclomiphene citrate in a buffered solution at pH 4.5 of acetic acid/sodium acetate, due to the formation of the Enclomiphene acetate salt in solution.

Example 24: Study Hygroscopicity of Enclomiphene Citrate Crystal Habits

The hygroscopicity of the different batches of Enclomiphene citrate was determined by DVS (Dynamic Vapour Sorption) with a Q5000 TA instrument. This is a gravimetric technique that measures how much water is absorbed or desorbed by a sample at different relative humidity (RH). At each RH, the sample mass must be allowed to reach gravimetric equilibrium (or surpassed time limit) before progressing to the next humidity level. Sorption and desorption isotherms will be performed at 25° C. over a range of 0-95% RH. The type of sorption isotherm is determined by the pore size and surface character of the material.

DVS was performed with 12.2509 mg of Enclomiphene citrate batch 722 and 13.5772 mg of Enclomiphene citrate batch 723 with the following conditions:

Gravimetric equilibration at 25° C. —0% RH

Increase to the next RH % level when gravimetric variation is inferior to 0.01% after 20 min or when the equilibration time surpasses the time limit of 300 min.

Batch 722—Enclomiphene citrate having non-needle crystal habit.

DVS analysis of batch 722 indicates significant moisture sorption between 0% and 65% RH (+2% weight). The water uptake then increases more drastically to reach 6% weight at 95% RH. The adsorption and desorption profiles are essentially overlapped indicating that the moisture "picked-up" at higher humidities should be adsorbed onto the surface of the material and does not affect its internal structure.

The sorption has a sigmoidal shape characteristic of Type II isotherms. The amount of vapor adsorbed increases rapidly at lower relative pressures, showing a profile concave with respect to the x-axis. At higher relative pressures, the curve assumes a shape convex with respect to the x-axis. The turning point of the curve is usually considered as the completion of the monomolecular layer and the beginning of the formation of multi-molecular layers of adsorbate on the surface.

Batch 723—Enclomiphene citrate having needle crystal habit.

DVS analysis of batch 723 indicates significant moisture sorption between 0% and 95% RH (+2.33% weight). The sorption and desorption profiles are overlapped indicating that the moisture "picked-up" at higher humidities should be adsorbed onto the surface of the material and does not affect its internal structure.

As for Enclomiphene citrate batch 722, the sorption has a sigmoidal shape characteristic of Type II isotherms.

Comparison batches 722 and 723.

The hygroscopicity of Enclomiphene citrate batches 722 and 723 is identical between 0 and 65% RH. Then the hygroscopicity increases strongly in the case of batch 722, i.e. for Enclomiphene citrate having non-needle crystal habit, up to 6% at 95% RH, while it increases moderately in the case of batch 723, i.e. for Enclomiphene citrate having needle crystal habit achieving 2.3% at 95% RH (See FIG. 18).

Thus, Enclomiphene citrate having needle shaped crystal habit, shows much better hygroscopicity behavior in comparison to Enclomiphene citrate having non-needle shaped crystal habit, especially at relative humidity higher than 65%.

Example 25: Morphology Analysis

The following pictures were acquired using a Zeiss AXIOSCOPE Optical Microscope, equipped with 4×, 10×, 50× lens and polarization tint plate:

- FIG. 7-BIS: Enclomiphene citrate having non-needle shaped crystal habit.
- FIG. 8-BIS: Enclomiphene citrate having needle shaped crystal habit.
- FIG. 11-BIS: Enclomiphene base having prismatic shaped crystal habit.
- FIG. 12-BIS: Enclomiphene base having non-prismatic shaped crystal habit.

Example 26: Stability Study of Enclomiphene (Base) Having Prismatic Shaped Crystal Habit Microscopy analysis of Enclomiphene base having prismatic shaped crystal habit exposed to three stability conditions for 30 days indicated the same colorless transparent prism as the starting product. See FIG. 19. Therefore the crystal habit of Enclomiphene having prismatic shaped crystals remains stable at least one month under the three stability conditions.

Example 27: Particle Size Distribution (PSD) Study of Enclomiphene (Base) Having Prismatic Shaped Crystal Habit Particle size of samples of batches 724 and 725 of Enclomiphene base was analyzed. These two sample of Enclomiphene base present very different morphologies:

Batch 724 is Enclomiphene having prismatic shaped crystal habit which is composed by monocrystalline prisms that not aggregate Batch 725 is Enclomiphene having non-prismatic shaped crystal habit which is composed by soft polycrystalline aggregates whose fragments are short needles.

Different techniques can be used in order to determine the population size distribution (Microscopy image analysis, sieving, sedimentation . . . ). However laser diffraction particle size analyzer using light scattering is one of the most widely used. It is worth noting that each technique is liable to generate a different mean diameter as well as measuring different properties of the particle. Therefore it is very important to indicate the used technique when a result of mean size is given.

Particle size analysis by laser diffraction analyzer can be performed in wet or dry dispersion. However wet dispersion was selected because:

- it allows to use only a small amount of sample,
- it is recommended for fragile particles such as organic crystals.

1.1 Experimental Method

Particle size distribution was analyzed in a Beckman Coulter LS13320 apparatus equipped with an Universal Liquid Module.

The particles have to be insoluble in the liquid used for the wet dispersion to avoid dissolution during the measurement. Therefore water was selected as liquid dispersant because it was observed in the last study that Enclomiphene base is highly insoluble in water.

40 mg of the sample were stirred in 25 ml of water and 3 drops of Triton X100 (to improve the wettability of the crystals and to avoid agglomeration during the analysis). If necessary, ultrasonic irradiation (bath 30 kHz and 200 W) was used for short time in order to break up any agglomerates or aggregates.

1.2 Analysis of Batch 724

In the case of batch 724, a satisfactory dispersion was observed in water containing surfactant (Triton X100) and sonication was not necessary.

Figure 20:
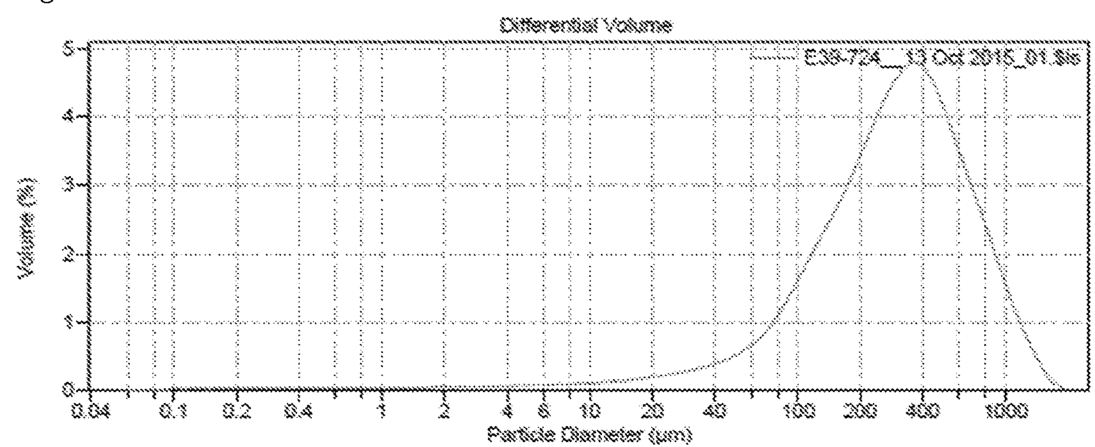
FIG. 20 shows PSD analysis of Enclomiphene base having prismatic crystal habit.

Particle size distribution of batch 724, i.e. Enclomiphene having prismatic shaped crystal habit shows a gaussian distribution with the mean value at 374.3 μm and the median at 306.54 μm (see FIG. 20 and the following table after). In this case we observe a distribution of particles with a relatively big size (80-770 μm) which matches with the microscopy observations.

PSD values batch 724

| PSD | Sample 724 |
|---|---|
| Mean | 374.3 μm |
| Median (D50) | 306.4 μm |
| Mode | 356.1 μm |
| D10 | 81.89 μm |
| D90 | 770 μm |

1.3 Analysis of Batch 725

In the case of batch 725, i.e. Enclomiphene having non-prismatic shaped crystal habit, aggregates were observed after the dispersion in water of the sample in presence of surfactants. Other solvents were tested to improve the dispersion without success because dissolution of the particles was observed.

Therefore two analyses were carried out, the first one without sonication and the second one with a short sonication in order to break the aggregates. However sonication could also break the crystals, so the measurements after sonication could yield lower values of particle size.

Without Sonication:

The particle size distribution follows a bimodal distribution (with a maximum at ca. 30 μm and a shoulder at ca. 100 μm), with different values for the mean (36.79 μm) and the median (24.96 μm) (see FIG. 21 and table below after). However as aggregates were observed during the analysis, the measured particle size is bigger than real particle size.

PSD values batch 725 without sonication

| PSD | Sample 725 (without sonication) |
|---|---|
| Mean | 36.79 μm |
| Median (D50) | 24.96 μm |
| Mode | 26.14 μm |
| D10 | 5.819 μm |
| D90 | 90.47 μm |

Figure 22:
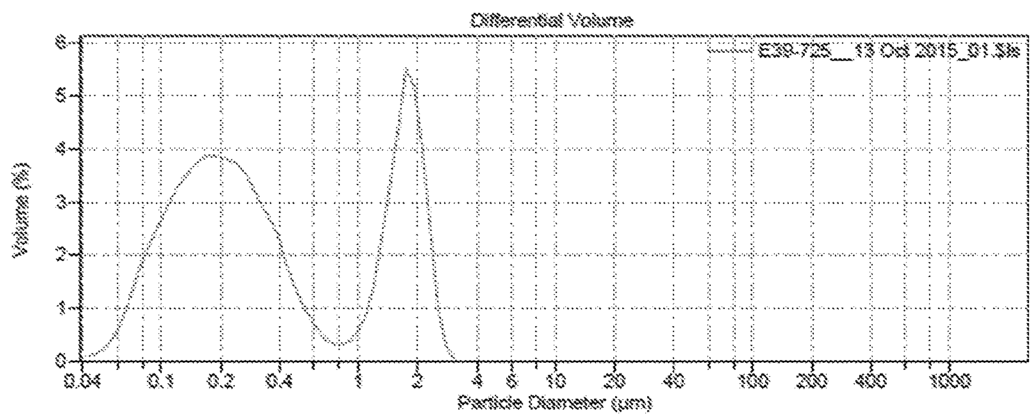
FIG. 22 shows PSD analysis of Enclomiphene base having non-prismatic crystal habit, after sonication.

With Sonication:

In order to break the aggregates observed in this first analysis, a short sonication was performed (10 s). In this case, a bimodal distribution was also obtained but the particle size decreased drastically: the mean and median values after sonication are below 1 μm, 0.715 μm and 0.284 μm respectively (see FIG. 22 and table below after). However a microscopy analysis of the solid in suspension seems to indicate that sonication broke the crystals in smaller ones. Therefore the particle size obtained from this analysis is also not real.

PSD values batch 725 with sonication.

| PSD | Sample 725 (10 sec sonication) |
|---|---|
| Mean | 0.715 μm |
| Median (D50) | 0.284 μm |
| Mode | 1.748 μm |
| D10 | 0.100 μm |
| D90 | 1.942 μm |

Thus according to said results in terms of PSD, a process for preparing micronized Enclomiphene base comprises the treatment of Enclomiphene base with sonication. Micronized Enclomiphene base thus prepared shows a PSD as described in the table above and in FIG. 22.

In particular, micronized Enclomiphene shows a mean value of particle size distribution (PSD) comprised in the range of 0.2 μm to 1.5 μm, preferably between 0.5 and 1.0 μm.

In particular, micronized Enclomiphene shows median (D50) value of particle size distribution (PSD) comprised in the range of 0.1 μm to 0.5 μm, preferably between 0.2 and 0.4 μm.

Example 28: Preparation of Enclomiphene Having Primastic Shaped Crystal Habit

Scheme of Synthesis:

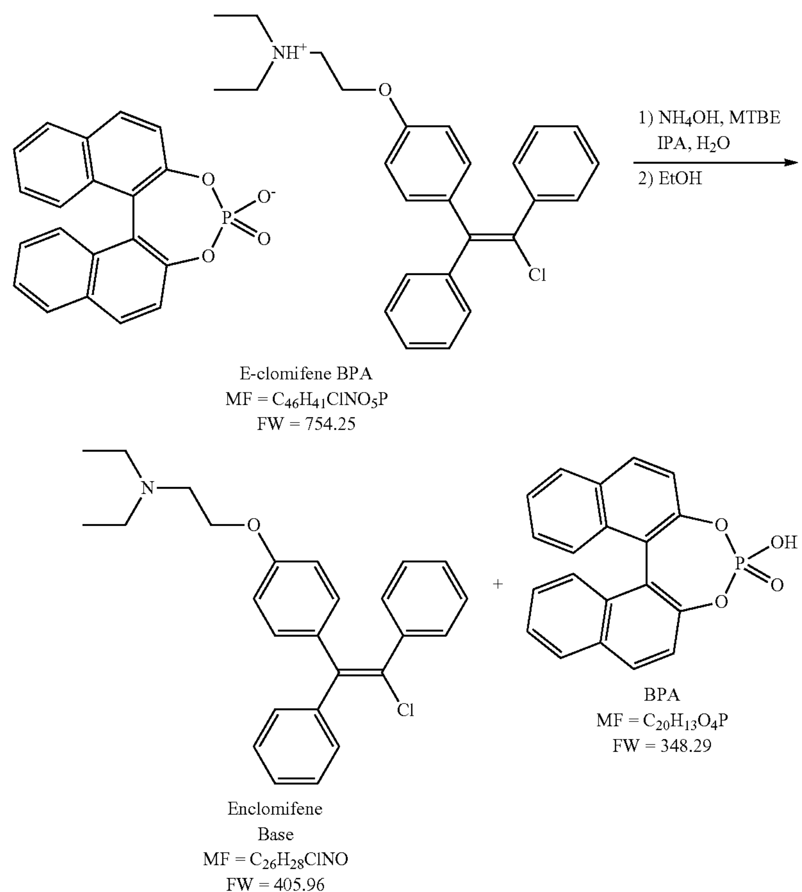

A round bottom flask, equipped with thermometer, reflux condenser, impeller and dropping funnel was filled with nitrogen and charged with: 10 g (1 equiv.) of Enclomiphene-BPA salt [HPLC profile of starting material Enclomiphene-BPA salt: Enclomiphene 99.39 A/A %, Cis-Clomiphene 0.14% A/A %; other impurities 0.47% A/A %], 50 mL (5 V) of Methyl Tert-butyl ether (MTBE); 5 mL (0.5 V) of Isopropanol; 50 mL (5 V) of Purified Water. The suspension was stirred and then 12 mL (1.2 V) of ammonia solution 30% wt/wt. were added. The resulting mixture was stirred for 15 minutes. At this stage pH is >10. (If not, pH could be correct by dropping of Ammonia solution 30% wt/wt). The organic phase was separated and washed with a solution of 3 mL (0.3 V) ammonia solution 30% wt/wt and 15 mL of purified water. The resulting mixture was stirred for 15 minutes, then the organic phase was collected and evaporated under vacuum, with a rotatory evaporator operating at Tmax=50° C. The crude was dissolved with 10 mL (1V) of toluene and then evaporated under vacuum, with a rotatory evaporator operating at Tmax=50° C. Subsequently, the crude was re-dissolved with 25 mL (2.5V) of absolute ethanol and the mixture was heated up to 50° C. in order to better dissolve the crude. Finally, the mixture was slowly cooled down to 0° C. and allowed to stir for 2 h. The suspension was filtered by suction filtration and the cake was washed with 5 mL (0.5V) of cold absolute ethanol. The thus obtained product was dried under vacuum at 50° C. for 8 h. This procedure afforded 3.90 g (72.4% yield) of Enclomiphene base as white prismatic crystalline solid, i.e. Enclomiphene having primastic shaped crystal habit.

HPLC profile of produced Enclomiphene base: Enclomiphene 99.83% A/A %, Cis-Clomiphene 0.03% A/A %, other impurities 0.14% A/A %.

Example 29: Preparation of Enclomiphene Citrate Having Needle Shaped Crystal Habit, Via Intermediate Enclomiphene Base Having Prismatic Shaped Crystal Habit

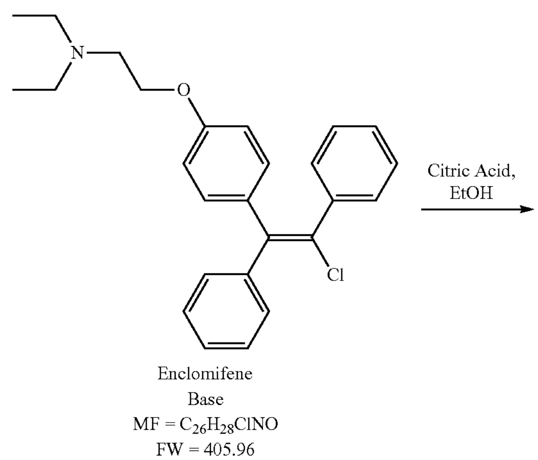

-continued

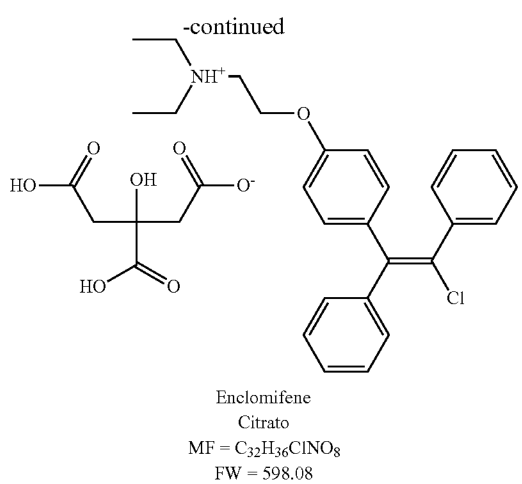

A round bottom flask, equipped with thermometer, reflux condenser, impeller and dropping funnel was filled with nitrogen and charged with: 2.0 g (1 equiv.) of Enclomiphene base having primastic shaped crystal habit (prepared in example 28) and 2.0 mL of absolute ethanol. the mixture was heated up to 50° C. in order to dissolve the crude, than a solution composed by 1.04 g (1.1 equiv) of anhydrous citric acid in 8.0 mL (8V) of absolute ethanol was added slowly and at the same temperature. The mixture was slowly cooled down to 0° C., and allowed to stir for 2 h. The suspension was filtered by suction filtration and the cake was washed with 2 mL (1V) of cold absolute ethanol. The thus obtained product was dried under vacuum at 50° C. for 8 h. This procedure afforded 2.80 g (95.0% yield) of Enclomifene citrate as white thin needles, i.e. Enclomiphene citrate having needle shaped crystal habit.

FIG. 25, in particular the pictures identified from FIG. 25-A to FIG. 25-D clearly shows the needle shaped crystal habit of this Enclomiphene citrate.

HPLC profile of Enclomiphene citrate: Enclomiphene 99.92 A/A %; Cis-Clomiphene 0.03% A/A %, other impurities 0.04% A/A %.

It can be appreciated how, passing through the preparation of Enclomiphene base having prismatic shaped crystal habit, it is possible to prepare Enclomiphene citrate with very high chemical purity (by experiment 28 plus experiment 29). Indeed, as shown in experiment 28, the isolation of Enclomiphene base having prismatic shaped crystal habit allows a remarkable reduction of the amount of the impurities, in particular cis-Enclomiphene impurity, which is instead not removed or decreased in the later preparation of Enclomiphene citrate, in particular, Enclomiphene citrate having needle shaped crystal habit.

Example 30: Preparation of Enclomiphene Acetate

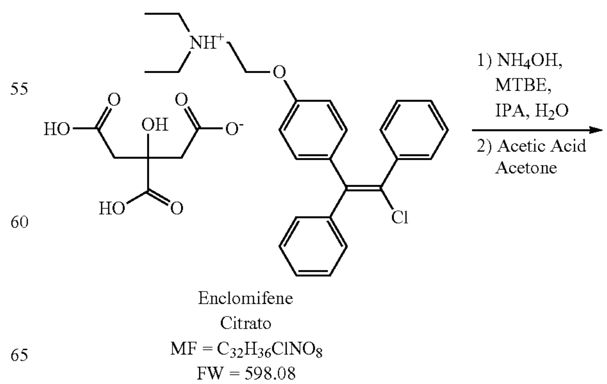

-continued

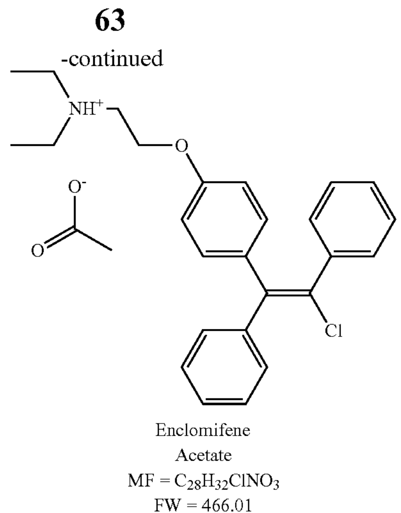

Enclomifene Acetate
MF = $C_{28}H_{32}ClNO_3$
FW = 466.01

A round bottom flask, equipped with thermometer, reflux condenser, impeller and dropping funnel was filled with nitrogen and charged with: 9 g (1 equiv.) of Enclomifene citrate, 45 mL (5 V) of methyl tert-butyl ether (MTBE); 4.5 mL (0.5 V) of Isopropanol; 45 mL (5 V) of purified water. The suspension was stirred and then 11 mL (1.2 V) of Ammonia solution 30% wt/wt. were added. The resulting mixture was stirred for 15 minutes. At this stage pH is >10. (If not, pH could be correct by dropping of Ammonia solution 30% wt/wt). The organic phase was separated and washed with a solution of 2.7 mL (0.3 V) Ammonia solution 30% wt/wt and 13.5 (1.5V) mL of purified water. The resulting mixture was stirred for 15 minutes, then the organic phase was collected and evaporated under vacuum, with a rotatory evaporator operating at Tmax=50° C. The crude was dissolved with 9 mL (1V) of toluene and then evaporated under vacuum, with a rotatory evaporator operating at Tmax=50° C. Subsequently, the crude was re-dissolved with 9 mL (1V) of acetone and the mixture was heated up to 40° C. in order to better dissolve the crude, finally 3.44 mL (4 equiv.) of acetic acid were added. The mixture cooled to room temperature and stirred for 2 hours, then the solvents were evaporated with a rotatory evaporator operating at Tmax=60° C. This procedure afforded 6.73 g (96% yield) of Enclomiphene Acetate as colourless oil.

HPLC profile of Enclomiphene acetate: Enclomiphene: 99.83 A/A %, Cis-Clomiphene 0.08% A/A %; other impurities 0.09% A/A %.

Figure 23:
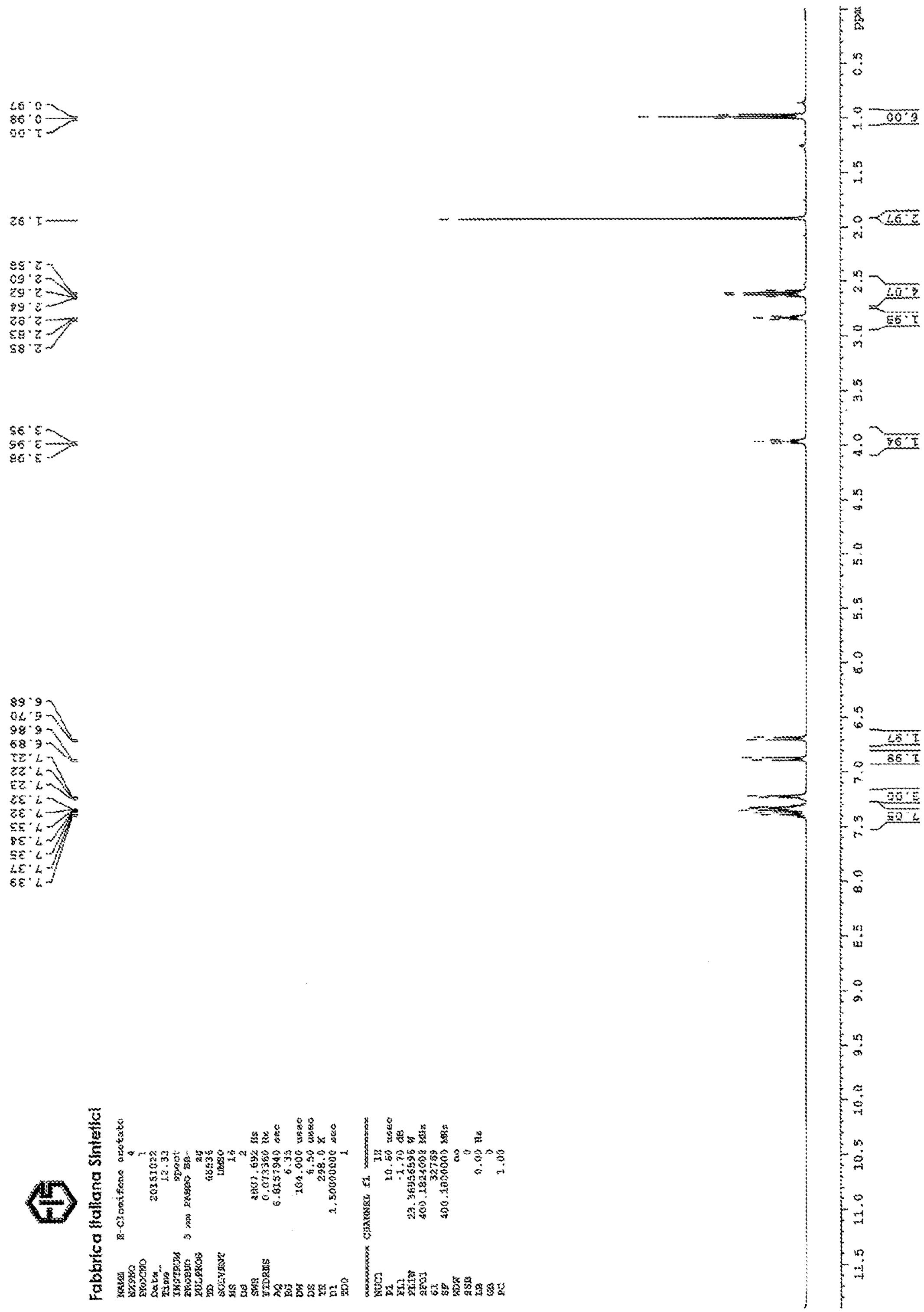
FIG. 23 shows $^{1}$H-NMR spectrum of Enclomiphene citrate.

$^{1}$H-NMR (400 MHz, DMSO-$d_6$): δ=7.45-7.37 (m, 2H), 7.36-7.29 (m, 5H), 7.28-7.21 (m, 3H), 6.86 (dt, J=9.1; 3 Hz, 2H), 6.71 (dt, J=9.1; 3 Hz, 2H), 3.95 (t, J=5.8 Hz, 2H), 2.79 (t, J=5.8 Hz, 2H), 2.59 (q, J=7.5 Hz, 4H), 1.92 (s, 3H), 0.97 (t, J=7.5 Hz, 6H) (See FIG. 23).

Figure 24:
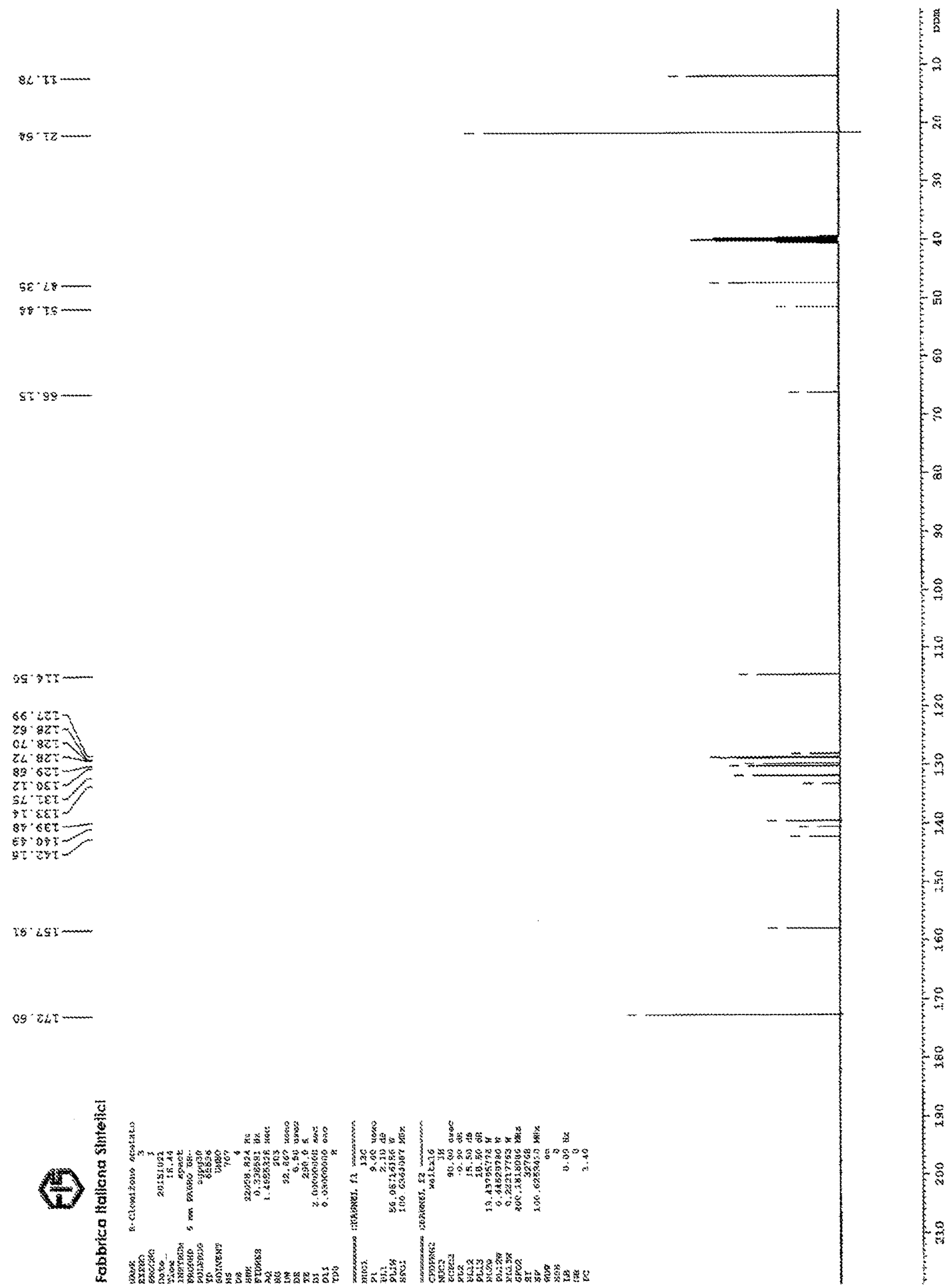
FIG. 24 shows $^{13}$C-NMR spectrum of Enclomiphene citrate.

$^{13}$C-NMR (100 MHz, DMSO-$d_6$): 172.6, 157.9, 142.2, 140.4, 139.3, 133.1, 131.7, 130.1, 129.7, 128.7, 128.69, 128.61, 127.9, 114.5, 66.1, 51.4, 47.3, 21.6, 11.8 (See FIG. 24).

The oil was further dried under vacuum at 50° C. overnight, then it was suspended in heptane and concentrated several time. In order to trigger the precipitation of Enclomiphene acetate, the oil was scratched with a glass rod. The product was finally kept under nitrogen at room temperature and it became a solid (slithery waxy) after two days. Said solid shows a large peak at DSC analysis with onset at 60° C. and peak at 68° C. (acquired with the same method previously described).

Example 31: Solubility Study of Enclomiphene Citrate

Solubility of Enclomiphene citrate was performed by duplicated at pH 4.5 buffered. For each Enclomiphene citrate samples, the results are shown in the following table:

| Time | Encl. Citr. 1 | Encl. Citr. 2 | Encl. Citr. average | Encl. Citr. SD |
|---|---|---|---|---|
| 0 min | 0 | 0 | 0 | 0 |
| 15 min | 14226 | 13911 | 14069 | 223 |
| 45 min | 13689 | 13852 | 13771 | 115 |
| 90 min | 12557 | 14860 | 13708 | 1628 |
| 180 min | 13058 | 13333 | 13196 | 195 |

The HPLC area average values of Enclomiphene citrate batches were plotted against time:

See FIG. 28

According to the above plot, it can be appreciated that the solubility of Enclomiphene citrate is much higher than the solubility of Enclomiphene citrate in the 4.5 pH buffered solution, whatever is the solid form of Enclomiphe citrate (respectively 12000-14000 HPLC area versus 1000-5000 HPLC area, only).

The invention claimed is:

1. Enclomiphene citrate of formula (III):

(III)

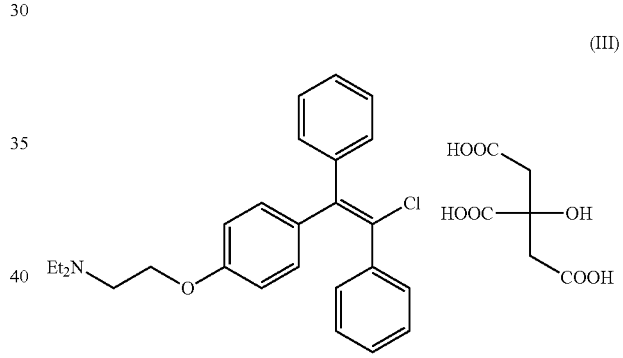

having needle shaped crystal habit, and having a melting point of 150° C. as measured by DSC (onset), or a characteristic X-ray powder diffraction pattern with characteristic peaks expressed in 2-Theta values (2θ) at: 5.8, 11.5.

2. Enclomiphene citrate according to claim 1 having a melting point of 150° C. as measured by DSC (onset) and a characteristic X-ray powder diffraction pattern with characteristic peaks expressed in 2-Theta values (2θ) at: 5.8, 11.5.

3. Enclomiphene citrate according to claim 1, having a characteristic X-ray powder diffraction pattern with characteristic peaks expressed in 2-Theta values (2θ) at: 5.8 (vs), 11.5 (vs); wherein (vs)=very strong intensity.

4. Enclomiphene citrate according to claim 1, having a characteristic X-ray powder diffraction pattern with characteristic peaks expressed in 2-Theta values (2θ) at: 5.8 (vs), 11.5 (vs), 12.7 (s), 14.9 (s) and 24.9 (s); wherein (vs)=very strong intensity; (s)=strong intensity.

5. Enclomiphene citrate according to claim 1, having a characteristic X-ray powder diffraction pattern with characteristic peaks expressed in 2-Theta values (2θ) at: 5.8 (vs), 9.7 (m), 10.9 (m), 11.5 (vs), 12.7 (s), 14.9 (s), 17.1 (m), 20.6 (m), 21.8 (m), 23.6 (m), 23.7 (m) and 24.9 (s); wherein (vs)=very strong intensity; (s)=strong intensity, (m)=medium intensity.

6. Pharmaceutical compositions comprising Enclomiphene citrate according to claim 1 and one or more pharmaceutical acceptable excipients.

7. Pharmaceutical compositions according to the claim 6 which are fast-release pharmaceutical compositions.

* * * * *